US011877782B2

United States Patent
Wang et al.

(10) Patent No.: US 11,877,782 B2
(45) Date of Patent: Jan. 23, 2024

(54) ELECTRICAL CONTROL SYSTEM FOR MINIMALLY INVASIVE TUMOR THERAPIES

(71) Applicant: HYGEA MEDICAL TECHNOLOGY CO., LTD., Beijing (CN)

(72) Inventors: Shi Wang, Beijing (CN); Fei Xiong, Beijing (CN); Jian Xiao, Beijing (CN); Jingjing Yang, Beijing (CN); Qianfu Huang, Beijing (CN)

(73) Assignee: HYGEA MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/008,665

(22) PCT Filed: Jul. 21, 2022

(86) PCT No.: PCT/CN2022/106945
§ 371 (c)(1),
(2) Date: Dec. 6, 2022

(87) PCT Pub. No.: WO2023/001215
PCT Pub. Date: Jan. 26, 2023

(65) Prior Publication Data
US 2023/0190355 A1 Jun. 22, 2023

(30) Foreign Application Priority Data
Jul. 22, 2021 (CN) .......................... 202110832038.5

(51) Int. Cl.
*A61B 18/02* (2006.01)
*A61B 18/04* (2006.01)
*A61B 18/00* (2006.01)

(52) U.S. Cl.
CPC ............. *A61B 18/02* (2013.01); *A61B 18/04* (2013.01); *A61B 2018/00577* (2013.01);
(Continued)

(58) Field of Classification Search
CPC .......... A61B 18/02; A61B 2018/00577; A61B 2018/00815; A61B 2018/00821; A61B 2018/0212; A61B 2018/0268
See application file for complete search history.

(56) References Cited

U.S. PATENT DOCUMENTS

| 2004/0078033 A1* | 4/2004 | Levin ..................... A61B 18/02 606/20 |
| 2005/0137659 A1 | 6/2005 | Garabedian et al. |

(Continued)

FOREIGN PATENT DOCUMENTS

| CN | 108897348 A | 11/2018 |
| CN | 110882051 A | 3/2020 |

(Continued)

OTHER PUBLICATIONS

1st Office Action of counterpart Chinese Patent Application No. 202110832038.5 dated Jun. 15, 2022.

(Continued)

*Primary Examiner* — Daniel W Fowler

(57) ABSTRACT

Disclosed is an electrical control system for minimally invasive tumor therapies. The electrical control system for minimally invasive tumor therapies includes a control module, a perfusion module and a power box. The perfusion module includes a working medium storage tank, a tank liquid level meter, a tank pressure sensor, a tank deflation valve, a liquid charging valve and an external working medium container. The power box is configured to supply power to the control module and the perfusion module. The control module is configured to receive working medium parameters sent by the tank liquid level meter and the tank pressure sensor, and to control, when the work medium parameters meet a perfusion condition, the tank deflation valve and the liquid charging valve to open or close respec- (Continued)

tively so as to input working medium from the external working medium container into the working medium storage tank.

12 Claims, 16 Drawing Sheets

(52) U.S. Cl.
CPC ............... *A61B 2018/00672* (2013.01); *A61B 2018/00678* (2013.01); *A61B 2018/00714* (2013.01); *A61B 2018/00744* (2013.01); *A61B 2018/00791* (2013.01); *A61B 2018/00898* (2013.01); *A61B 2018/00952* (2013.01); *A61B 2018/00994* (2013.01); *A61B 2018/0212* (2013.01); *A61B 2018/0262* (2013.01); *A61B 2018/046* (2013.01)

(56) References Cited

U.S. PATENT DOCUMENTS

| | | | | |
|---|---|---|---|---|
| 2005/0177148 | A1* | 8/2005 | van der Walt | A61B 18/02 606/21 |
| 2009/0292279 | A1* | 11/2009 | Bliweis | A61B 18/02 606/21 |
| 2010/0057067 | A1* | 3/2010 | Baust | F17C 9/00 62/51.1 |
| 2011/0087206 | A1* | 4/2011 | Geiselhart | A61B 18/02 607/104 |
| 2013/0103020 | A1* | 4/2013 | Levin | A61B 18/02 606/26 |
| 2014/0163538 | A1* | 6/2014 | Ryba | A61F 7/0085 606/21 |
| 2014/0343639 | A1* | 11/2014 | Hopper | A61F 7/0085 607/104 |
| 2015/0300569 | A1* | 10/2015 | Baust | A61B 18/02 62/50.1 |

FOREIGN PATENT DOCUMENTS

| | | |
|---|---|---|
| CN | 110926073 A | 3/2020 |
| CN | 110934635 A | 3/2020 |
| CN | 210662293 U | 6/2020 |

OTHER PUBLICATIONS

Notice of Allowance of counterpart Chinese Patent Application No. 202110832038.5 dated Aug. 1, 2022.

* cited by examiner

ELECTRICAL CONTROL SYSTEM FOR MINIMALLY INVASIVE TUMOR THERAPIES

CROSS-REFERENCE TO RELATED APPLICATION

The present application claims the priority of Chinese patent application No. 202110832038.5 filed on Jul. 22, 2021 and entitled "Electrical Control System for Minimally Invasive tumor therapies", the entirety of which is incorporated herein by reference.

FIELD OF THE INVENTION

The present disclosure relates to the technical field of medical instruments, in particular to an electrical control system for minimally invasive tumor therapies.

BACKGROUND OF THE INVENTION

With the rapid development of medical technology and scientific technology, a variety of intelligent medical devices have emerged. It is shown from clinical data that a single freezing or heating therapy can kill tumor tissue. However, if freezing is not thorough enough, there is a risk that the cancer cell tissue will not be completely destroyed. During the heating therapy, the human body feels slightly stronger pain and a high temperature can stimulate blood circulation, which could promote the spread of cancer cells along blood vessels to a certain extent. Based on this, a combined cryoablation & hyperthermia tumor treatment device combines the advantages of cryoablation and thermal ablation, and avoids the defects of a single function device, which can achieve a wide treatment temperature range and ablate tumors more thoroughly with the combination of cold and heat therapies, and can play a better role in the field of cancer therapies. For a combined cryoablation & hyperthermia tumor ablation device, one problem to be solved by those skilled in the art is how to make it more accurate to control a high-temperature working medium and a low-temperature working medium to complete a safe and effective ablation probe therapy on lesion tissue.

SUMMARY OF THE INVENTION

To overcome the defects in the prior art, embodiments of the disclosure provide an electrical control system for minimally invasive tumor therapies.

An embodiment of the disclosure provides an electrical control system for minimally invasive tumor therapies. The system includes a control module, a perfusion module and a power box. The perfusion module includes a working medium storage tank, a tank liquid level meter, a tank pressure sensor, a tank deflation valve, a liquid charging valve and an external working medium container. The power box is configured to supply power to the control module and the perfusion module. The control module is configured to receive working medium parameters sent by the tank liquid level meter and the tank pressure sensor, and to control, when the work medium parameters meet a perfusion condition, the tank deflation valve and the liquid charging valve to open or close respectively, so as to input working medium from the external working medium container into the working medium storage tank.

DETAILED DESCRIPTION OF THE EMBODIMENTS

Figure 1:
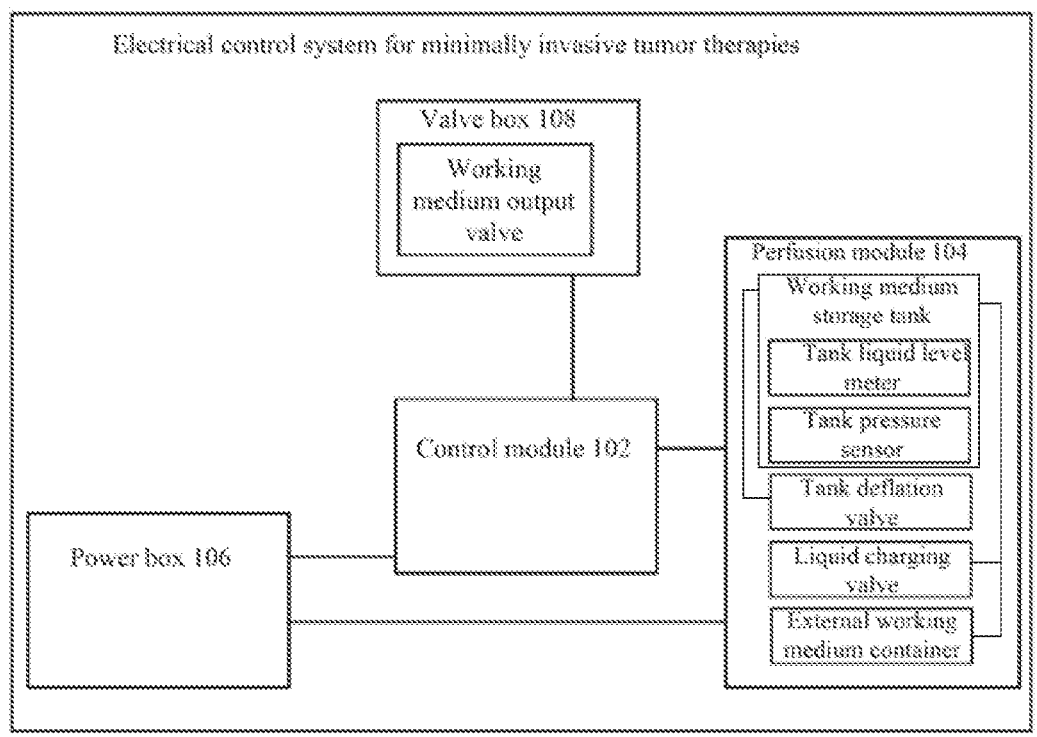
FIG. 1 is a structural block diagram of an electrical control system for minimally invasive tumor therapies provided by an embodiment of the disclosure.

Many specific details are set forth in the following description to facilitate a full understanding of the disclosure. However, the disclosure can be implemented in many other ways than those described herein, and those skilled in the art can make similar promotions without departing from the contents of the description. Therefore, the disclosure is not limited by any embodiment disclosed below.

The terms used in one or more embodiments of the description are merely intended for illustration of a particular embodiment, but not for limitation of the one or more embodiments of the description. The singular forms of "a/an", "said" and "the" used in one or more embodiments of the description and in the appended claims are also intended to include plural forms, unless explicitly stated otherwise. It is also to be understood that the term "and/or" used in one or more embodiments of the description refers to and encompasses any or all possible combinations of one or more of the associated listed items.

It should be understood that although the terms of first, second, etc. can be employed to describe various information in one or more embodiments of the description, such information should not be limited to these terms. These terms are used merely to distinguish the same type of information from each other. For example, without departing from the scope of one or more embodiments of the description, "first" can also be referred to as the second, and similarly, "second" can also be referred to as the first. Depending on the context, the word "if" used herein could be interpreted as "in a case that . . . " or "when . . . " or "in response to a determining that . . . ".

A high-and-low-temperature multi-mode system for minimally invasive tumor therapies is a minimally invasive device for treating a tumor using a physical therapy. It is shown from clinical data that a single freezing or heating therapy can kill tumor tissue. However, if freezing is not thorough enough, the cancer cells may not be completely destroyed. During the heating therapy, the human body feels slightly stronger pain and the high temperature can stimulate blood circulation, which could promote the spread of the cancer cells along blood vessels to a certain extent. Therefore, a combined cryoablation & hyperthermia tumor treatment device can function better in the field of cancer therapies.

At present, the developed high-and-low-temperature cryosurgery system lacks the function of automatically filling refrigeration and heating working medium, and thus requiring an operator to add them manually, resulting in the risk of improperly adding working medium. The device is difficult to push on an uphill road surface in a narrow space, and there is a risk of accidentally hitting people and devices. In addition, it is suggested that functions such as auxiliary temperature measurement should be also added during a surgery.

Therefore, the disclosure devises an electrical control system for minimally invasive tumor therapies. A control module, a perfusion module and a power box are provided in the system. Adding of refrigeration and heating working medium is automatically controlled by the control module, thereby avoiding improper addition of the working medium and improving the timeliness, accuracy and efficiency of adding the working medium.

In the disclosure, provided is an electrical control system for minimally invasive tumor therapies, which will be described in detail in the embodiments below.

FIG. 1 shows a structural block diagram of an electrical control system for minimally invasive tumor therapies provided by an embodiment of the disclosure. The system includes a control module 102, a perfusion module 104 and a power box 106. The perfusion module 104 includes a working medium storage tank, a tank liquid level meter, a tank pressure sensor, a tank deflation valve, a liquid charging valve and an external working medium container.

The power box 106 is configured to supply power to the control module 102 and the perfusion module 104.

The control module 102 is configured to receive working medium parameters sent by the tank liquid level meter and the tank pressure sensor, and to control, when the work medium parameters meet a perfusion condition, the tank deflation valve and the liquid charging valve to open or close respectively so as to input a working medium from the external working medium container into the working medium storage tank.

In an implementation, the control module is configured to real-timely receive various working medium parameters detected by the perfusion module, and automatically control the perfusion module to perform related operations based on the real-time working medium parameters, so as to control the perfusion module to automatically complete a perfusion operation of a working medium. The working medium is a therapeutic medium that needs to be output by means of a therapeutic device during a therapeutic surgery, i.e., a therapeutic medium that needs to be stored in a working medium storage tank of the electrical control system for minimally invasive tumor therapies. The working medium may include a refrigeration working medium, such as liquid nitrogen, and may also include a heating working medium, such as alcohol.

In practical application, the working medium storage tank is configured to receive and store a working medium from the external working medium container, and then output it by means of an ablation probe connected thereto for a tumor therapy. The tank liquid level meter and the tank pressure sensor located inside the working medium storage tank are configured to detect and send working medium parameters of the working medium storage tank to the control module in real time.

The tank deflation valve is configured to control a pressure intensity inside the working medium storage tank, and for example, the pressure intensity inside the working medium storage tank can be reduced by opening the tank deflation valve. The liquid charging valve located on a conveying pipeline between the working medium storage tank and the external working medium container is configured to control the external working medium container to perfuse the working medium storage tank with a working medium. For example, when the liquid charging valve is opened, the working medium storage tank can be perfused with the working medium from the external working medium container, and when the liquid charging valve is closed, the working medium storage tank cannot be perfused with the working medium from the external working medium container.

The working medium parameters of the tank liquid level meter and the tank pressure sensor can represent the situation of the working medium stored inside the working medium storage tank. Therefore, the control module may analyze the working medium parameters when receiving them to determine whether they meet a perfusion condition. If the working medium parameters meet the perfusion condition, it means that the working medium stored inside the working medium storage tank may be insufficient. In this case, the control module can automatically control the tank deflation valve and the liquid charging valve to open or close respectively, so as to automatically control inputting the working medium from the external working medium container into the working medium storage tank.

The perfusion condition may be a preset condition of starting the perfusion of the working medium, which is used to indicate a condition that needs to be met for controlling the tank deflation valve and the liquid charging valve to open or close respectively, so as to input the working medium from the external working medium container into the working medium storage tank.

In one implementation of the embodiment, the working parameter sent by the tank liquid level meter is a liquid level of the working medium inside the working medium storage tank, and the working parameter sent by the tank pressure sensor is a tank pressure intensity of the working medium storage tank. The control module 102 in an implementation is configured to: determine, when the received liquid level is lower than a first liquid level threshold value, whether the received tank pressure intensity is less than a first pressure intensity threshold value; open, if the received tank pressure intensity is not less than the first pressure intensity threshold value, the tank deflation valve, so as to reduce the internal pressure intensity of the working medium storage tank; and continue to determine whether the received tank pressure intensity is less than the first pressure intensity threshold value, until it is determined that the received tank pressure intensity is less than the first pressure intensity threshold value, keep the tank deflation valve in an open state, and open the liquid charging valve, so as to input the working medium from the external working medium container into the working medium storage tank.

In an implementation, the first liquid level threshold value may be a preset numerical value, which is used to judge whether the working medium stored in the working medium storage tank is sufficient. For example, the first liquid level threshold value may be 95%, 90%, etc. The first pressure intensity threshold value may also be a preset numerical value, which is used to judge whether the pressure intensity of the working medium storage tank is too high. For example, the first pressure intensity threshold value may be 300 KPa.

In one implementation of the embodiment, the liquid charging valve is located on a conveying pipeline between the working medium storage tank and the external working medium container. The liquid charging valve is arranged close to the working medium storage tank. When the liquid charging valve is in an open state, the working medium storage tank can be perfused with the working medium from the external working medium container via the conveying pipeline.

After receiving a liquid level sent by the tank liquid level meter, the control module may determine whether the received liquid level is lower than the first liquid level threshold value. If the received liquid level is not lower than the first liquid level threshold value, it represents that the working medium stored in the working medium storage tank is relatively sufficient and no perfusion is required. If the received liquid level is lower than the first liquid level threshold value, it represents that the working medium stored in the working medium storage tank is insufficient and perfusion is required.

The working medium storage tank is configured to receive and store the working medium, and if the internal pressure intensity of the working medium storage tank is too high, it may be dangerous to start perfusion directly. Accordingly, when it is determined by the control module that the received liquid level is lower than the first liquid level threshold value, the control module in one implementation also needs to judge whether the tank pressure intensity sent by the tank pressure sensor is less than the first pressure intensity threshold value. If the tank pressure intensity is not less than the first pressure intensity threshold value, it means that the internal pressure intensity of the working medium storage tank is relatively high, and it may be dangerous to start perfusion directly. Thus, the control module may now control the tank deflation valve to open, so as to reduce the pressure intensity of the working medium storage tank, and the perfusion of a working medium is not allowed at this moment. After opening the tank deflation valve for deflating to reduce the internal pressure intensity of the working medium storage tank, it may continue to real-timely determine whether the received tank pressure intensity is less than the first pressure intensity threshold value, until it is determined that the received tank pressure intensity is less than the first pressure intensity threshold value. It means that the working medium storage tank now has relatively low internal pressure intensity and can be perfused with a working medium. In this case, the liquid charging valve may be opened, so as to input the working medium from the external working medium container into the working medium storage tank. In addition, in the perfusion process of a working medium, the internal pressure intensity of the working medium storage tank may be increased, which may cause danger. Thus, in the process of opening the liquid charging valve to perfuse it with the working medium, the tank deflation valve can now be kept in an open state for deflating, so as to control the internal pressure intensity of the working medium storage tank not to be too high.

If the tank pressure intensity sent by the tank pressure sensor is less than the first pressure intensity threshold value, it means that the internal pressure intensity of the working medium storage tank is relatively low, and perfusion is relatively safe. In this case, the control module can directly control the liquid charging valve to open, so as to input the working medium from the external working medium container into the working medium storage tank, and in the process of inputting the working medium, real-timely determine whether the received tank pressure intensity is less than the first pressure intensity threshold value. If the received pressure intensity is not less than the first pressure intensity threshold value, the tank deflation valve is controlled to open, so as to reduce the internal pressure intensity of the working medium storage tank and avoid an increase of gas pressure in the process of perfusion as well as the resultant danger.

In practical application, the control module may control various valves to open and close by means of high and low electrical levels. That is, each of the valves involved in the disclosure may be an electric valve, which is opened when receiving a high electrical level and closed when receiving a low electrical level, or which is opened when receiving a low electrical level and closed when receiving a high electrical level. For example, when the control module needs to control the tank deflation valve to close, it may send a high-electrical-level signal to the tank deflation valve, which may then be automatically closed when receiving the high-electrical-level signal. When the control module needs to control the tank deflation valve to open, it may send a low-electrical-level signal to the tank deflation valve, which may then be automatically opened when receiving the low-electrical-level signal. In addition, the approach for controlling the liquid charging valve to open and close may also be similar to the above control approach with respect to the tank deflation valve, that is, the opening and closing of the liquid charging valve are controlled by means of high and low electrical levels.

Each of the valves in the disclosure may be controlled referring to the above approach for control by means of high and low electrical levels. Of course, other approaches capable of controlling the valves to open and close are also possible, such as installing relays in the valves. The control module may control the relays to pull in and bounce off through control signals, so as to control the valves to open and close, which is not limited in the disclosure.

In one implementation of the embodiment, as shown in FIG. 1, the system may also include a valve box 108. The valve box 108 includes a working medium output valve. The control module 102 in an implementation is configured to close the working medium output valve when opening the liquid charging valve.

In an implementation, the valve box may be provided with a plurality of valves to control multiple functions. The working medium output valve is configured to control the working medium stored in the working medium storage tank to be output to an ablation probe during a surgery, so as to treat a tumor.

When the liquid charging valve is opened, it means that the working medium stored in the working medium storage tank is insufficient and perfusion is required. In the process of inputting the working medium from the external working medium container into the working medium storage tank, i.e., in the perfusion process of the working medium, the working medium cannot be output at the same time in case of danger. Therefore, it is necessary to control the working medium output valve to close when the liquid charging valve is opened, so as to control the working medium to make it unable to be output, thus avoiding the danger caused by simultaneous perfusion and output of the working medium, which will improve safety.

Figure 2:
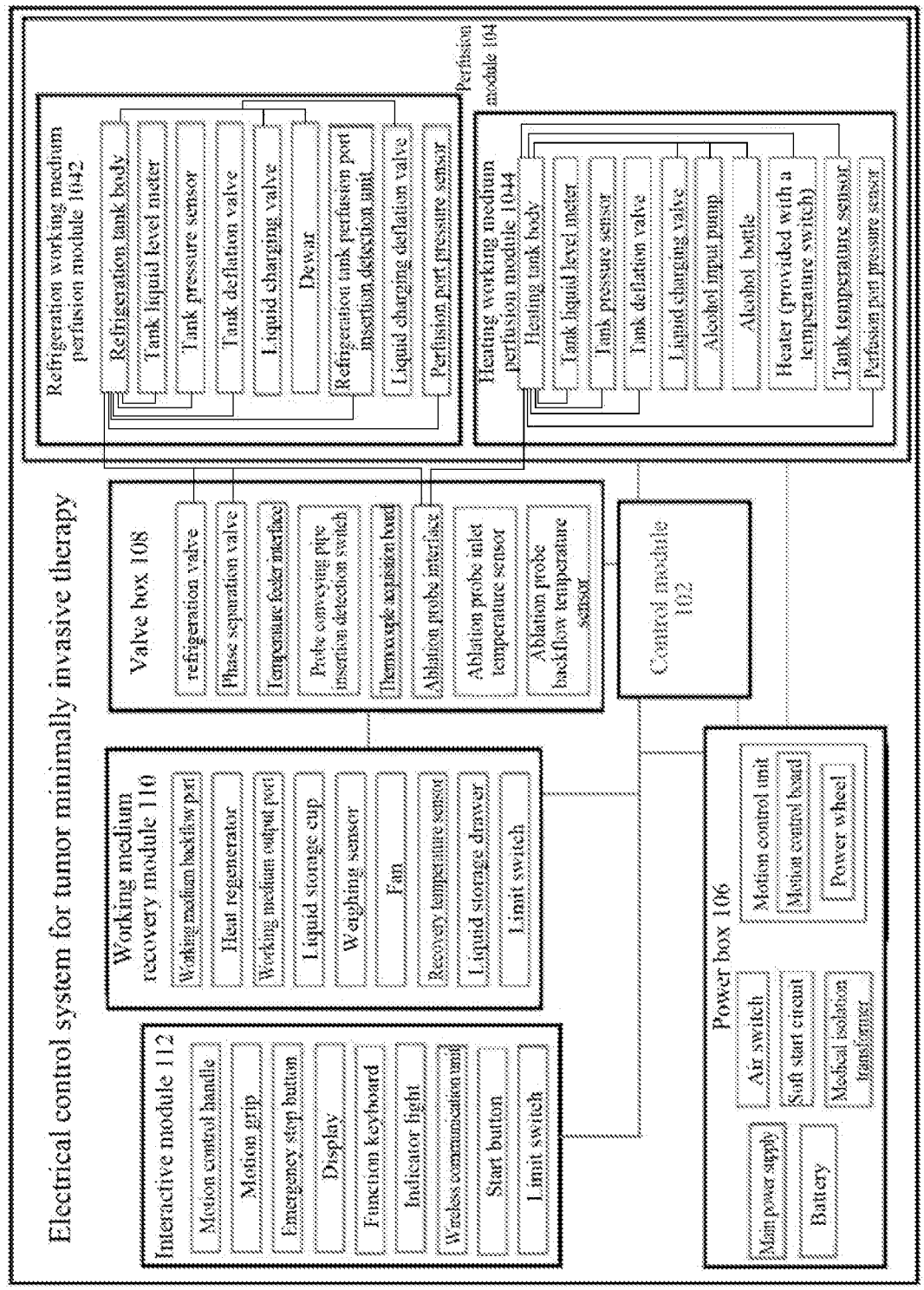
FIG. 2 is a structural block diagram of another electrical control system for minimally invasive tumor therapies provided by an embodiment of the disclosure.

In one implementation of the embodiment, FIG. 2 shows a structural block diagram of another electrical control system for minimally invasive tumor therapies. As shown in FIG. 2, the perfusion module 104 may include a refrigeration working medium perfusion module 1042. The working medium storage tank is a refrigeration tank body. The external working medium container is a Dewar vessel, which is connected with the refrigeration tank body through a Dewar conveying pipeline. The refrigeration working medium perfusion module 1042 also includes a refrigeration tank perfusion port insertion detection unit. The control module 102 in an implementation is configured to: detect, when a received liquid level is lower than a first liquid level threshold value, whether the Dewar conveying pipeline is connected with the refrigeration tank body according to an insertion message sent by the refrigeration tank perfusion port insertion detection unit; and perform, when the Dewar conveying pipeline is connected with the refrigeration tank body, an operation step of determining whether a received tank pressure intensity is less than a first pressure intensity threshold value.

As shown in FIG. 2, in the electrical control system for minimally invasive tumor therapies provided in the disclosure, automatic perfusion of a refrigeration working medium may be carried out, that is, the perfusion module may include a refrigeration working medium perfusion module, in which case the working medium storage tank is a refrigeration tank body. A tank liquid level meter is configured to measure and send the liquid level of a refrigeration working medium inside the refrigeration tank body to the control module for analytical processing. A tank pressure sensor is configured to measure and send the internal pressure intensity of the refrigeration tank body to the control module for analytical processing; and a tank deflation valve is configured to control the internal pressure intensity of the refrigeration tank body. A liquid charging valve is configured to control the automatic perfusion of the refrigeration working medium. The working medium output valve is a refrigeration valve which is configured to control the refrigeration working medium to be output to an ablation probe. The external working medium container is a Dewar vessel, which refers to an external apparatus that contains liquid nitrogen, and the refrigeration tank body, upon connecting to the Dewar vessel, can be added with the refrigeration working medium.

In practical application, the liquid charging valve is located on the Dewar conveying pipeline and arranged close to the refrigeration tank body. When the liquid charging valve is in an open state, the refrigeration tank body can be perfused with the refrigeration working medium from the Dewar vessel via the Dewar conveying pipeline.

During automatic perfusion of the refrigeration working medium, the Dewar vessel needs to be externally connected, and the Dewar vessel and the refrigeration tank body are connected through the Dewar conveying pipeline, so as to perfuse the refrigeration tank body with the liquid nitrogen stored in the Dewar vessel. Therefore, it is necessary to detect whether the Dewar conveying pipeline is connected before the perfusion of the refrigeration working medium, and after it is detected by the control module that the Dewar conveying pipeline is normally connected, the control module detects whether the refrigeration tank body needs to deflate for pressure reduction before the perfusion of the refrigeration working medium. That is, when it is determined by the control module that the received liquid level is lower than the first liquid level threshold value and before it determines whether the internal pressure intensity of the refrigeration tank body is relatively low, the control module may also detect whether the Dewar conveying pipeline is connected with the refrigeration tank body according to an insertion message sent by the refrigeration tank perfusion port insertion detection unit, and then perform, when the Dewar conveying pipeline is normally connected, the operation step of determining whether the received tank pressure intensity is less than the first pressure intensity threshold value, so as to carry out the subsequent process of automatic perfusion of the refrigeration working medium.

In practical application, the refrigeration tank perfusion port insertion detection unit, which may be located at a tank port of the refrigeration tank body, is configured to detect whether the Dewar conveying pipeline is connected in place. After the Dewar conveying pipeline is connected in place, the refrigeration tank perfusion port insertion detection unit may send a successful connection signal to the control module. After receiving the signal, the control module determines that the Dewar conveying pipeline is successfully connected, and the subsequent process automatic perfusion of the refrigeration working medium may be continued.

In an implementation, the Dewar conveying pipeline connected to the Dewar vessel has a magnetic ring at its front end, and the refrigeration tank perfusion port insertion detection unit arranged at the tank port of the refrigeration tank body is a magnetic ring detector. After the Dewar conveying pipeline is connected in place, the magnetic ring detector may detect the magnetic ring, generate a successful connection signal, and transmit it to the control module, in which case it is detected by the control module that the Dewar conveying pipeline is normally connected with the refrigeration tank body.

In one implementation of the embodiment, as shown in FIG. 2, the refrigeration working medium perfusion module 1042 may also include a liquid charging deflation valve. The liquid charging deflation valve is located on the Dewar conveying pipeline and arranged close to the Dewar vessel. The valve box 108 is also provided with a phase separation valve. The control module 102 in an implementation is configured to open the phase separation valve and close the liquid charging deflation valve when opening the liquid charging valve.

In the process of automatic perfusion of the refrigeration working medium, when the refrigeration working medium inside the refrigeration tank body has been sufficient, it is necessary to stop perfusion and close the liquid charging valve. At this moment, if the Dewar vessel is not closed in time, it will still output the refrigeration working medium to the Dewar conveying pipeline, however, the liquid charging valve has been closed, thus the refrigeration working medium through the conveying pipeline cannot be conveyed into the refrigeration tank body and may be gasified into a large amount of gas, which would be accumulated in the Dewar conveying pipeline, resulting in an excessive pressure intensity in the Dewar conveying pipeline and causing danger. Therefore, it is also possible to provide a liquid charging deflation valve on the Dewar conveying pipeline and arrange the liquid charging deflation valve close to the Dewar vessel. When the liquid charging valve is closed, the refrigeration working medium from the Dewar vessel will be gasified into gas when passing through the liquid charging deflation valve and discharged via the liquid charging deflation valve, thus the gas inside the Dewar conveying pipeline can be released, thereby reducing the pressure intensity and improving safety.

In addition, when the liquid charging valve is opened, it means that it is necessary to input the refrigeration working medium (liquid nitrogen) from the Dewar vessel into the refrigeration tank body. At this moment, if the liquid charging deflation valve is in an open state, the refrigeration working medium in the Dewar vessel, after entering the Dewar conveying pipeline, may be gasified into gas at the liquid charging deflation valve and discharged from the liquid charging deflation valve, as a result, perfusion of the refrigeration working medium cannot be achieved. Therefore, when the liquid charging valve is opened, the liquid charging deflation valve needs to be closed, so as to avoid the refrigeration working medium from being gasified and discharged at the liquid charging deflation valve after flowing out from the Dewar vessel, and ensure perfusion efficiency.

In practical application, in the process of outputting the refrigeration working medium, the refrigerating capacity will be lost along the way, causing part of the refrigeration working medium to turn into gas, and thus, the box valve may also be provided with the phase separation valve. The phase separation valve is used to discharge gaseous nitrogen to make the pipeline filled with flowing liquid nitrogen, which is convenient for the refrigeration working medium to enter the inside of the refrigeration tank body, thus reducing the pressure intensity inside the refrigeration tank body as much as possible. Therefore, when the liquid charging valve is opened for the perfusion of the refrigeration working medium, the phase separation valve may also be opened simultaneously. That is, during the perfusion of the refrigeration working medium, in addition to opening the liquid charging valve and closing the refrigeration valve, it is also necessary to open the phase separation valve and meanwhile close the liquid charging deflation valve.

In addition, as for the automatic perfusion of the refrigeration working medium, the refrigeration tank body needs to be perfused with the liquid nitrogen in the Dewar vessel. If the tank deflation valve and the liquid charging deflation valve are closed as receiving low electrical levels when the whole system is powered down, it may cause an excessive pressure intensity in the refrigeration tank body or the Dewar conveying pipeline, resulting in danger. Therefore, as for the refrigeration working medium perfusion module, the tank deflation valve arranged in the refrigeration tank body and the liquid charging deflation valve provided on the Dewar conveying pipeline should be opened when receiving low electrical levels and closed when receiving high electrical levels, thereby avoiding the refrigeration tank deflation valve and the liquid charging deflation valve from automatically close due to the powering down of the system, so as to ensure safety of the system.

In an implementation, the control module may send a low electrical level signal to the tank deflation valve inside the refrigeration tank body when the tank deflation valve inside the refrigeration tank body needs to be opened, and the tank deflation valve inside the refrigeration tank body may be automatically opened when receiving the low electrical level signal. The control module may send a high electrical level signal to the tank deflation valve inside the refrigeration tank body when the tank deflation valve inside the refrigeration tank body needs to be closed, and the tank deflation valve inside the refrigeration tank body is automatically closed when receiving the high electrical level signal.

All the valves involved in the disclosure may be normal electric valves, i.e., opened at high electrical levels and closed at low electrical levels, except for the tank deflation valve arranged in the refrigeration tank body and the liquid charging deflation valve provided on Dewar conveying pipeline which are closed at high electrical levels and opened at low electrical levels.

In one implementation of the embodiment, as shown in FIG. 2, the refrigeration working medium perfusion module 1042 also include a perfusion port pressure sensor. The perfusion port pressure sensor is configured to detect and send the perfusion port pressure intensity of the refrigeration tank body to the control module. The control module 102 in an implementation is configured to: determine, during a first preset duration after opening the liquid charging valve, whether a received liquid level is lower than a first liquid level threshold value; determine, if the received liquid level is lower than the first liquid level threshold value, whether the perfusion port pressure intensity is greater than a second pressure intensity threshold value; and feed back, if the perfusion port pressure intensity is not greater than the second pressure intensity threshold value, a prompt message for opening the Dewar vessel, or continue to determine, if the perfusion port pressure intensity is greater than the second pressure intensity threshold value, whether the received liquid level is lower than the first liquid level threshold value, until the received liquid level is not lower than the first liquid level threshold value.

In an implementation, the perfusion port pressure sensor, which is arranged at the perfusion port of the Dewar vessel, is configured to detect the perfusion port pressure intensity of the Dewar vessel. The Dewar vessel has a self-pressurization function and may be self-pressurized after being opened, thus the pressure intensity at the perfusion port of the Dewar vessel may be detected by the perfusion port pressure sensor, so as to determine whether the Dewar vessel is opened. In addition, the first preset duration is a preset time period. The preset duration may be set based on the duration that is required for the perfusion of the refrigeration working medium into the refrigeration tank body, such as 2 minutes, 5 minutes, 7 minutes, etc. That is, after the first preset duration of perfusion, the liquid level inside the refrigeration tank body should exceed the first liquid level threshold value. The second pressure intensity threshold value may be a preset pressure intensity numerical value, which is used to judge whether the pressure intensity at the perfusion port of the Dewar vessel is relatively high, so as to determine whether the Dewar vessel is opened. For example, the second pressure intensity threshold value may be 5 KPa.

In practical application, during the first preset duration after opening the liquid charging valve, whether the received liquid level is lower than the first liquid level threshold value may be determined, and if the received liquid level is still lower than the first liquid level threshold value, it means that the Dewar vessel may not be opened. Therefore, although the liquid charging valve is opened, there is no refrigeration working medium output from the Dewar vessel, and thus the refrigeration working medium may not be successfully perfused. In this case, whether the perfusion port pressure intensity is greater than a second perfusion port pressure intensity may therefore be determined. If the perfusion port pressure intensity is less than the second pressure intensity threshold value, it means that the Dewar vessel is not opened, in which case the prompt message for opening the Dewar vessel may be fed back to remind an operator to open the Dewar vessel. If the perfusion port pressure intensity is not less than the second pressure intensity threshold value, it means that the Dewar vessel is opened, in which case perfusion of the refrigeration working medium is being carried out, and the control module only needs to continue to wait, that is; continue to determine whether the real-timely received liquid level is lower than the first liquid level threshold value, until the received liquid level is not lower than the first liquid level threshold value, which means that the perfusion of the refrigeration working medium is completed.

In one implementation of the embodiment, the control module 102 in an implementation is configured to: close, when it is determined that a received liquid level is not lower than the first liquid level threshold value, the tank deflation valve, the liquid charging valve and the phase separation valve, and keep the working medium output valve in a closed state and open the liquid charging deflation valve; determine whether the perfusion port pressure intensity is less than a third pressure intensity threshold value; and feed back, if the perfusion port pressure intensity is less than the third pressure intensity threshold value, a prompt message for pulling out the Dewar conveying pipeline, or keep, if the perfusion port pressure intensity is not less than the third pressure intensity threshold value, the respective open/close states of the tank deflation valve, the liquid charging valve, the working medium output valve, the phase separation valve and the liquid charging deflation valve unchanged, until a received perfusion port pressure intensity is less than the third pressure intensity threshold value.

In an implementation, the third pressure intensity threshold value may be a preset pressure intensity numerical value, which is used to judge whether the Dewar conveying pipeline may be safely pulled out. For example, the third pressure intensity threshold value may be 10 KPa.

In practical application, if it is determined that the received liquid level is not lower than the first liquid level threshold value, it means that the refrigeration working medium inside the refrigeration tank body has been sufficient, and the perfusion of the refrigeration working medium may be stopped. In this case, the control module may control the tank deflation valve, the liquid charging valve and the phase separation valve which are opened for the perfusion of the refrigeration working medium to close. At this moment, since the Dewar conveying pipeline has not been pulled out, the process of outputting the refrigeration working medium to the ablation probe still cannot be carried out, and it is necessary to continue to keep the working medium output valve in a closed state and open the liquid charging deflation valve, so as to enable the refrigeration working medium output from the Dewar vessel to be gasified into gas and discharged when passing through the liquid charging deflation valve, thereby reducing the pressure intensity at the perfusion port of the Dewar vessel.

If it is determined that the perfusion port pressure intensity is less than the third pressure intensity threshold value, it means that the perfusion port pressure intensity is relatively low, and perfusion is relatively safe. In this case, the prompt message for pulling out the Dewar conveying pipeline may be fed back, such that the operator may safely pull out the Dewar vessel.

If it is determined that the perfusion port pressure intensity is not less than the third pressure intensity threshold value, it means that the pressure intensity at the perfusion port of the Dewar vessel is relatively high, in which case it may be dangerous to pull out the Dewar conveying pipeline. Thus, it may continue to keep the respective open/close states of the tank deflation valve, the liquid charging valve, the working medium output valve, the phase separation valve and the liquid charging deflation valve unchanged, until the received perfusion port pressure intensity is less than the third pressure intensity threshold value, and then feed back the prompt message for pulling out the Dewar conveying pipeline.

Each of the tank deflation valve, the liquid charging valve, the phase separation valve, the working medium output valve, the liquid charging deflation valve and the like may be a solenoid valve, which needs to meet a voltage of 24 V and a current of 1 A or below. The tank pressure sensor and the perfusion port pressure sensor in the refrigeration working medium perfusion module are powered at 24 V, output current signals of 4 to 20 mA, and perform measurement in a range of 0 to 1 MPa. In addition, the tank liquid level meter in the refrigeration working medium perfusion module needs to meet a power supply of 24 V, outputs a current signal of 4 to 20 mA and performs measurement in a range determined depending on the height inside the refrigeration tank (i.e., based on customization), and since the temperature inside the refrigeration tank is in a range of 20° C. to minus 196° C., it is necessary to select a liquid level meter resistant to a low temperature.

In addition, a pressurization valve may also be provided on the refrigeration tank body in the refrigeration working medium perfusion module to increase the pressure intensity inside the refrigeration tank body when it needs to output the refrigeration working medium, such that the refrigeration working medium is output through a pressure intensity difference during a therapeutic surgery. As such, by adding the pressurization valve in the system, the work pressure can be increased within the original work pressure range, such that finer ablation probes can be put into use, thereby providing more series of ablation probes for the operator to use cooperatively.

Figure 3A:
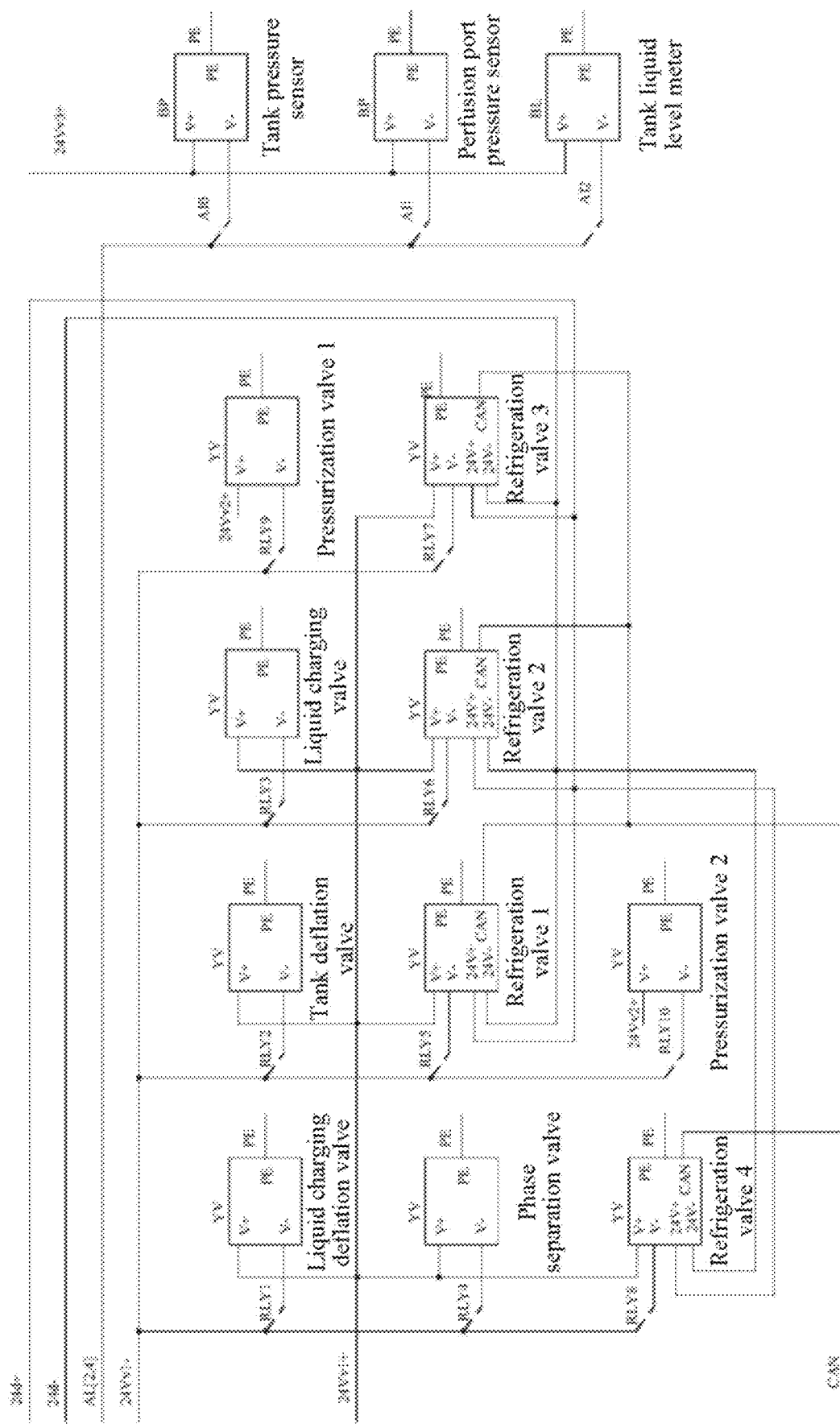
FIG. 3a is an electrical schematic diagram of a refrigeration working medium perfusion module provided by an embodiment of the disclosure.

In an implementation, FIG. 3a is an electrical schematic diagram of a refrigeration working medium perfusion module provided by an embodiment of the disclosure. As shown in FIG. 3a, the refrigeration working medium perfusion module includes a liquid charging deflation valve, a tank deflation valve, a liquid charging valve, two pressurization valves, a tank pressure sensor, a perfusion port pressure sensor and a tank liquid level meter. Correspondingly, a valve box includes a phase separation valve and four refrigeration valves (i.e., working medium output valves corresponding to the refrigeration working medium perfusion module). In the drawing, YV represents solenoid valves, BP represents pressure sensors, BL represents a liquid level meter, PE represents grounding pins, RLY1-10 represents relays for the input of digital value control signals, AI0-2 represents the input of analog value signals, AL[2,4] represents total analog value input signals, and 24Vv1, 24Vv2 and 24Vv3 respectively represents 24V input currents of different channels. As shown in FIG. 3A, the liquid charging deflation valve, the tank deflation valve, the liquid charging valve, the phase separation valve and four refrigeration valves serve as one channel of 24V input current (24Vv1). Two pressurization valves serve as one channel of input current (24Vv2). The tank pressure sensor, the perfusion port pressure sensor and the tank liquid level meter serve as one channel of current (24Vv3). In addition, d+ and d− also represent input currents and connect four refrigeration valves, and CAN represents a bus.

That is, the 24V input current may be divided into multiple channels, and the valves and sensors with different functions may be controlled through different channels of currents, such that the valves and sensors with different functions may be separately controlled so as to achieve corresponding functions.

The disclosed control module can, when it is determined that the liquid level inside the refrigeration tank body is insufficient, open the tank deflation valve, the liquid charging valve and the phase separation valve and close the working medium output valve and the liquid charging deflation valve to automatically perform the process of adding a refrigeration working medium, and can, after completing adding of the refrigeration working medium, automatically close the tank deflation valve, the liquid charging valve and the phase separation valve, keep the working medium output valve also in a close state and open the liquid charging deflation valve to stop the process of adding the refrigeration working medium. As such, the control module may automatically detect whether the liquid level inside the refrigeration tank body is sufficient, and when the liquid level is insufficient, automatically control the adding of the refrigeration working medium without manual operation by the operator. In this way, the working medium is automatically added, the process of adding the working medium is simplified, labor and time costs are saved, and it is ensured that working medium may be automatically and accurately added, thereby significantly improving the timeliness, accuracy and efficiency of adding the working medium.

In an implementation, the meteorological space of gas is relatively large after the liquid level decreases and the speed of heat exchange with the outside is decreased after the volume of the gas, such as nitrogen from liquid nitrogen gasification, is increased, thus, as the liquid level decreases, the pressurization time of the refrigeration tank body will become continuously longer. In the process of a practical therapeutic surgery, if, when the liquid level inside the refrigeration tank body is lower than 40%, pressurization is continued by opening the pressurization valve provided on the refrigeration tank body in a self-pressurization manner, it may cause a relatively slow pressurization of the refrigeration tank body. Therefore, in order to reduce the pressurization time of the refrigeration tank body when the liquid level is relatively low and to ensure that the therapeutic surgery may be carried out within a normal pressure range, the original pressurization manner may be changed. For example, a vacuum tank with a volume of about 3 L may be placed around the refrigeration tank body. The vacuum tank is connected with a refrigeration tank and an air compressor and respectively connected with a vacuum tank liquid charging valve and an auxiliary pressurization valve on a pipeline. The function of rapid pressurization may be achieved by using the vacuum tank and the air compressor to be connected with the refrigeration tank, i.e., according to a flashing principle. That is, the vacuum tank at a relatively low pressure is filled with the liquid nitrogen, such that the liquid nitrogen rapidly boils and is gasified into nitrogen, so as to achieve the purpose of rapid pressurization.

Figure 3B:
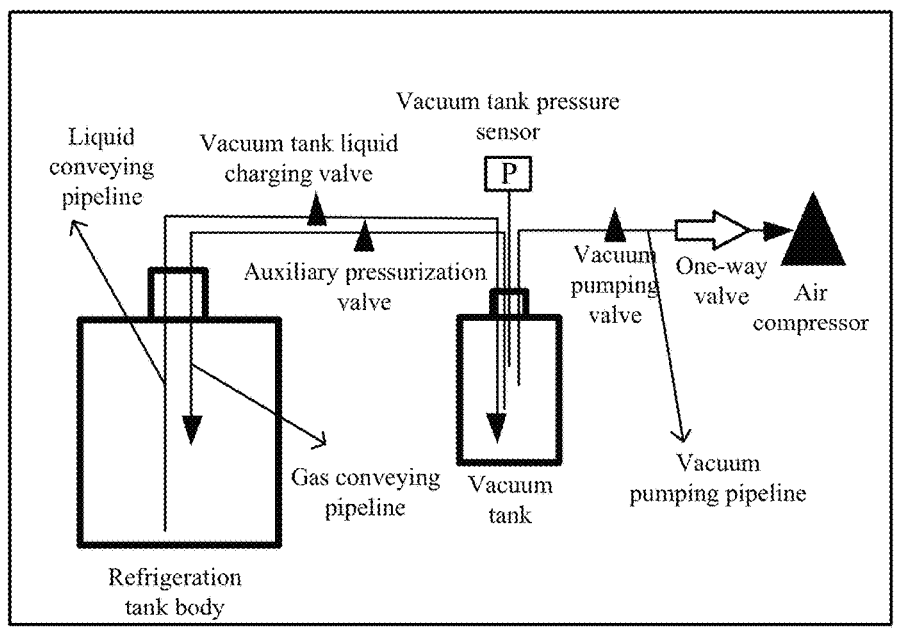
FIG. 3b is a schematic diagram of a pressurization structure provided by an embodiment of the disclosure.

FIG. 3b is a schematic diagram of a pressurization structure provided by an embodiment of the disclosure. As shown in FIG. 3b, an electrical control system for minimally invasive tumor therapies may also include a vacuum tank and an air compressor. The vacuum tank is provided with a vacuum tank pressure sensor P. A vacuum pumping pipeline is arranged between the vacuum tank and the air compressor. A vacuum pumping valve and a one-way valve are provided on the vacuum pumping pipeline. A liquid conveying pipeline and a gas conveying pipeline are arranged between the refrigeration tank body and the vacuum tank. A vacuum tank liquid charging valve is provided on the liquid conveying pipeline. An auxiliary pressurization valve is provided on the gas conveying pipeline.

After the vacuum pumping valve is opened, the air compressor may pump air from the vacuum tank, so as to reduce the pressure intensity inside the vacuum tank. Herein, the vacuum tank refers to a tank with a vacuum layer that is pumped into a negative pressure environment. Since after the air compressor is turned off, the vacuum pumping valve may not be closed instantly (there being a control command delay under normal circumstances), the one-way valve may also be provided on the vacuum pumping pipeline in order to avoid the air from flowing back to the vacuum tank. The one-way valve is a mechanical valve, which ensures that gas may only circulate in one direction, that is, gas may only be conveyed from the vacuum tank to the vacuum pumping pipeline, but not from the vacuum pumping pipeline to the vacuum tank, so as to maintain the current pressure intensity state of the vacuum tank.

In one implementation of the embodiment, the control module is further configured to: determine, after controlling the pressurization valve to open, whether a tank body pressure intensity of the refrigeration tank body reaches a fourth pressure intensity threshold value within a second preset duration; control, if the fourth pressure intensity threshold value is not reached, the vacuum tank liquid charging valve to open, so as to press a refrigeration working medium inside the refrigeration tank body into the vacuum tank through the liquid conveying pipeline; determine whether a vacuum tank pressure intensity sent by the vacuum tank pressure sensor is greater than a fifth pressure intensity threshold value, and control, if the vacuum tank pressure intensity is higher than the fifth pressure intensity threshold value, the vacuum tank liquid charging valve to close and the auxiliary pressurization valve to open, so as to increase a pressure intensity inside the refrigeration tank body; and determine whether a tank body pressure intensity inside the refrigeration tank body is greater than a sixth pressure intensity threshold value, and control, if the tank body pressure intensity is greater than the sixth pressure intensity threshold value, the auxiliary pressurization valve to close.

In an implementation, the second preset duration may refer to a preset time period, and for example, the second preset duration may be 1 minute. The fourth pressure intensity threshold value may refer to a preset pressure intensity numerical value, and for example, the fourth pressure intensity threshold value may be 50 KPa. The second preset duration and the fourth pressure intensity threshold value are used to judge whether the pressurization speed of the refrigeration tank body is normal, for example, whether the pressure intensity increases to 50 KPa or above within 1 minute. In addition, the fifth pressure intensity threshold value and the sixth pressure intensity threshold value each may refer to a preset pressure intensity numerical value. The fifth pressure intensity threshold value is used to judge whether the vacuum tank pressure intensity is high enough to assist the refrigeration tank body in pressurization, and for example, the fifth pressure intensity threshold value may be 1000 KPa. The sixth pressure intensity threshold value is used to judge whether the tank body pressure intensity inside the refrigeration tank body has increased to be high enough, and for example, the sixth pressure intensity threshold value may be 900 KPa.

After controlling the pressurization valve to open, the control module may real-timely monitor the tank body pressure intensity inside the refrigeration tank body to determine whether the tank body pressure intensity of the refrigeration tank body reaches the fourth pressure intensity threshold value within the second preset duration. If the fourth pressure intensity threshold value is not reached, it may be considered that a relatively slow pressurization may be caused by a relatively low liquid level inside the refrigeration tank body, or blocking of a pressurization pipeline, or poor heat exchange of the refrigeration tank body with the outside, or the like. In this case, auxiliary pressurization may be carried out depending upon the vacuum tank, therefore the vacuum tank liquid charging valve may be controlled to open. After the vacuum tank liquid charging valve is opened, the tank body pressure intensity inside the refrigeration tank body is greater than the vacuum tank pressure intensity, and thus the refrigeration working medium, such as liquid nitrogen, inside the refrigeration tank body may be pressed into the vacuum tank. The boiling point of the refrigeration working medium inside the vacuum tank may also decrease at a relatively low pressure intensity, in which case the refrigeration working medium is rapidly gasified into gas, thereby increasing the pressure intensity inside the vacuum tank.

Then, the control module may keep monitoring the vacuum tank pressure intensity sent by the vacuum tank pressure sensor to determine whether the vacuum tank pressure intensity is greater than the fifth pressure intensity threshold value. If it is monitored that the pressure intensity is higher than the fifth pressure intensity threshold value, it means that the vacuum tank pressure intensity has been high enough to assist the refrigeration tank body in pressurization. In this case, the control module may therefore control the vacuum tank liquid charging valve to close and the auxiliary pressurization valve to open, such that the gas in the vacuum tank may now enter the refrigeration tank body via the gas conveying pipeline, so as to increase the tank body pressure intensity inside the refrigeration tank body. Then, the control module may monitor the tank body pressure intensity of the refrigeration tank body to determine whether the tank body pressure intensity is greater than the sixth pressure intensity threshold value, and if the tank body pressure intensity is greater than the sixth pressure intensity threshold value, it means that the tank body pressure intensity of the refrigeration tank body has increased to be high enough. In this case, the control module may control the auxiliary pressurization valve to close, that is, stopping the process of auxiliary pressurization.

In addition, after the auxiliary pressurization valve and the vacuum tank liquid charging valve are closed, auxiliary pressurization is carried out on the refrigeration tank body by means of the vacuum tank, the vacuum tank pressure intensity increases and cannot meet the demand for the next auxiliary pressurization. In this case, the control module may therefore also control the vacuum pumping valve to be opened and the air compressor to be turned on, so as to pump air in the vacuum tank, until the vacuum tank pressure intensity decreases to a pressure intensity that meets the pressurization need, for example, the vacuum tank pressure intensity being determined less than 10 Pa for more than 1 minute. Then, the vacuum pumping valve may be closed and the air compressor may be turn off to wait for the next pressurization instruction.

In one implementation of the embodiment, only when the vacuum tank pressure intensity is low enough, can the refrigeration working medium inside the refrigeration tank body subsequently be pressed into the vacuum tank by means of a pressure difference, and can the refrigeration working medium be promoted to be rapidly gasified to increase the pressure intensity after entering the vacuum tank, and thus before it is determined that the tank body pressure intensity of the refrigeration tank body does not reach the fourth pressure intensity threshold value within the second preset duration, that is, the pressurization speed of the refrigeration tank body is relatively low and auxiliary pressurization is required, whether the vacuum tank pressure intensity is low enough may also be judged. That is, the control module in an implementation is configured to: determine whether the vacuum tank pressure intensity is less than a seventh pressure intensity threshold value for a third preset duration; and control, if the vacuum tank pressure intensity is not less than the seventh pressure intensity threshold value for the third preset duration, the air compressor to be turned on and the vacuum pumping valve to open, and return to perform an operation steps of determining whether the vacuum tank pressure intensity is less than the seventh pressure intensity threshold value for the third preset duration; and control, if the vacuum tank pressure intensity is less than the seventh pressure intensity threshold value for the third preset duration, the air compressor to be turned off and the vacuum pumping valve to close, and perform the operation step of controlling the vacuum tank liquid charging valve to open.

In an implementation, the third preset duration may be a preset time period, and for example, the third preset duration may also be 1 minute. The seventh pressure intensity threshold value may refer to a preset pressure intensity numerical value, and for example, the seventh pressure intensity threshold value may be 10 KPa. The third preset duration and the seventh pressure intensity threshold value are used to judge whether the vacuum tank pressure intensity is less than a certain pressure intensity for a certain time, for example, whether the vacuum tank pressure intensity is less than 10 KPa for more than 1 minute.

The control module may monitor whether the vacuum tank pressure intensity is less than the seventh pressure intensity threshold value for the third preset duration, and if the vacuum tank pressure intensity is not less than the seventh pressure intensity threshold value for third preset duration, it means that the vacuum tank pressure intensity is still not low enough to meet the condition and meet the subsequent auxiliary pressurization demand. In this case, the control module may therefore control the air compressor to be turned on and the vacuum pumping valve to open to pump air inside the vacuum tank by means of the air compressor, so as to decrease the vacuum tank pressure intensity, and continue to monitor whether the vacuum tank pressure intensity is less than the seventh pressure intensity threshold value for the third preset duration, that is, continue to monitor whether the vacuum tank pressure intensity needs the subsequent pressurization demand. If it is monitored that the vacuum tank pressure intensity is less than the seventh pressure intensity threshold value for the third preset duration, it means that the vacuum tank pressure intensity meets the subsequent pressurization demand. In this case, the control module may control the air compressor to be turned off and the vacuum pumping valve to close, and the vacuum tank liquid charging valve to open, so as to carry out the process of auxiliary pressurization.

It may cause a relatively slow pressurization of the refrigeration tank body due to a relatively low liquid level, or blocking of a pressurization pipeline, or poor heat exchange of the refrigeration tank body with the outside, or the like. Thus, in the disclosure, the vacuum tank is arranged in the system in order to ensure the tank body pressure intensity of the refrigeration tank body. The vacuum tank pressure intensity changes to assist the refrigeration tank body in pressurization, which will reduce the pressurization time of the refrigeration tank body and ensure that the therapeutic surgery can be carried out within a normal pressure range.

In one implementation of the embodiment, as shown in FIG. 2, the perfusion module 104 may also include a heating working medium perfusion module 1044. The working medium storage tank is a heating tank body. The external working medium container is an alcohol bottle. The heating working medium perfusion module 1044 may also include an alcohol input pump, which is located on a conveying pipeline between the heating tank body and the alcohol bottle and arranged close the alcohol bottle. The control module 102 in an implementation is configured to: turn on, when the liquid charging valve is opened, the alcohol input pump, so as to input a heating working medium from the alcohol bottle into the heating tank body; determine whether a received liquid level has changed after a fourth preset duration; and feed back, if the received liquid level has not changed, a prompt message for replacing the alcohol bottle; or continue to determine, if the received liquid level has changed, whether the received liquid level is lower than a first liquid level threshold value, until the received liquid level is not lower than the first liquid level threshold value, and close the tank deflation valve, the liquid charging valve and the alcohol input pump.

In the disclosed electrical control system for minimally invasive tumor therapies, automatic perfusion of a heating working medium can be carried out, that is, the perfusion module may include a heating working medium perfusion module, in which case the working medium storage tank is a heating tank body. A tank liquid level meter is configured to measure and send the liquid level of the heating working medium inside the heating tank body to the control module for analytical processing. The tank pressure sensor is configured to measure and send the internal pressure intensity of the heating tank body to the control module for analytical processing. The tank deflation valve is configured to control the internal pressure intensity of the refrigeration tank body. The liquid charging valve is configured to control the automatic perfusion of the heating working medium. The working medium output valve is a heating valve for controlling the heating working medium to be output to an ablation probe. The external working medium container is an alcohol bottle, an alcohol input pump is also arranged on a conveying pipeline between the heating tank body and the alcohol bottle, and alcohol in the alcohol bottle may be input into the heating tank body through the alcohol input pump.

In practical application, the liquid charging valve is located on the conveying pipeline between the heating tank body and the alcohol bottle and arranged close to the heating tank body. When the liquid charging valve and the alcohol input pump are in an open state, the heating tank body can be perfused with the heating working medium in the alcohol bottle through the alcohol input pump via the conveying pipeline.

During automatic perfusion of the heating working medium, in addition to opening the liquid charging valve, it is necessary to open the alcohol input pump to input the heating working medium from the alcohol bottle into the heating tank body, and it is also necessary to close the working medium output valve (i.e., a heating valve, which is a valve for controlling the heating working medium to be output to an ablation probe). In addition, the fourth preset duration is a preset time period. The fourth preset duration may be set based on the duration that is required for the perfusion of the refrigeration tank body with the heating working medium, such as 2 minutes, 5 minutes, 7 minutes, etc. That is, after the fourth preset duration of perfusion, the liquid level inside the heating tank body should changes. Additionally, the fourth preset duration may be the same as the first preset duration, or may be different from it.

In practical application, when the liquid charging valve is opened for the fourth preset duration, it may determine whether a received liquid level has changed. If the received liquid level has not changed, it means that alcohol in the alcohol bottle may be exhausted. As a result, although the liquid charging valve is opened and the alcohol input pump is turned on, there is no heating working medium output, therefore after a period of time, the liquid level inside the heating tank body has not changed, in which case a prompt message for replacing the alcohol bottle may be fed back to remind the operator to replace the alcohol bottle. If the liquid level inside the heating tank body has changed, it means that the alcohol in the alcohol bottle is being output to the heating tank body, that is, the perfusion of the heating working medium is being carried out, the control module only needs to continue to wait, that is, continue to determine whether the received liquid level is lower than the first liquid level threshold value, until the received liquid level is not lower than the first liquid level threshold value, which means that the perfusion of the heating working medium is completed, in which case the tank deflation valve and the liquid charging valve may be closed and the alcohol input pump may be turned off.

In an implementation, the alcohol input pump is a power source for the automatic adding process, which should meet electrical specifications of a control voltage of 24 V and the maximum current of 3 A or below. As for the liquid charging valve, the tank deflation valve and the working medium output valve in the heating working medium perfusion module, these solenoid valves should meet a control voltage of 24 V and a current of 1 A or below. The tank liquid level meter in the heating working medium perfusion module needs to meet a power supply of 24 V, outputs a current signal of 4 to 20 mA and performs measurement in a span (measurement range) which needs to be determined depending on the height of the heating tank (i.e., based on customization). Since the temperature inside the heating tank is in a range of 20° C. to 150° C., it is necessary to select a liquid level meter resistant to a high temperature.

The disclosed control module can, when it is determined that the liquid level inside the heating tank body is insufficient, open the tank deflation valve and the liquid charging valve, turn on the alcohol input pump and close the working medium output valve to automatically perform the process of adding a heating working medium, and can, after completing adding of the heating working medium, automatically control the tank deflation valve and the liquid charging valve to close, keep the working medium output valve also in a close state and stop the process of adding the heating working medium. As such, the control module may automatically detect whether the liquid level inside the heating tank body is sufficient, and when the liquid level is insufficient, automatically control adding of the heating working medium without manual operation by the operator. In this way, the working medium is automatically added, the process of adding the working medium is simplified, labor and time costs are saved, and it is ensured that working medium can be automatically and accurately added, thereby significantly improving the timeliness, accuracy and efficiency of adding the working medium.

In one implementation of the embodiment, as shown in FIG. 2, the power box 106 includes a main power supply and a battery. The heating working medium perfusion module 1044 also includes a heater and a tank temperature sensor. The control module 102 in an implementation is configured to: determine, when a received liquid level is higher than a second liquid level threshold valve, whether the heater is powered by the main power supply; determine, if the heater is powered by the main power supply, whether a received heating tank body temperature sent by the tank temperature sensor reaches a first temperature threshold value; and control, if the received heating tank body temperature does not reach the first temperature threshold value, the heater to start heating; or control, if the received heating tank body temperature reaches the first temperature threshold value, the heater to stop heating.

In an implementation, the power box includes a main power supply and a battery. The main power supply may be a 220 V power supply from a wall socket. The battery as a standby power supply may output a voltage of 24 V. For example, the battery includes but is not limited to a lithium battery. The second liquid level threshold value may be a preset numerical value, which is used to judge whether the heating working medium in the heating tank body may be heated to avoid dry burning. For example, the second liquid level threshold value may be 5%, 10%, etc. The first temperature threshold value may be a preset numerical value, which is used to determine whether the temperature inside the heating tank body reaches a desired temperature value. For example, the first temperature threshold value may be 119° C.

In practical application, firstly, the tank liquid level meter detects a current liquid level of the heating tank body, and sends the liquid level to the control module. If it is determined by the control module that the received liquid level is lower than the second liquid level threshold value, the control module controls the heater to stop heating (so as to prevent dry burning due to the low liquid level); or if the liquid level is higher than the second liquid level threshold value, the control module may continue to judge whether the heater is powered by the main power supply, that is, whether the power supply comes from the wall socket (220 V). If it is detected by the control module that the power supply comes from the battery (a standby power supply), the control module may control the heater to stop heating (so as to prevent the battery from running out quickly due to excessive output power). If it is detected that the heater is powered by the main power supply, the control module may continue to detect whether the temperature inside the heating tank body reaches the first temperature threshold value. If the temperature reaches the first temperature threshold value, the control module may control the heater to stop heating; or if the temperature does not reach the first temperature threshold value, the control module may control the heater to start heating, until the heating tank body temperature reaches the first temperature threshold value, the control module controls the heater to stop heating, and for example, the first temperature threshold value may be 119° C.

In one implementation of the embodiment, the control module 102 is further configured to: determine, in the process of controlling the heater to perform heating, whether a received tank body pressure intensity exceeds an eighth pressure intensity threshold value; and open, when the received tank body pressure intensity exceeds the eighth pressure intensity threshold value, the tank deflation valve, and continue to determine whether the received tank body pressure intensity exceeds the eighth pressure intensity threshold value, until the received tank body pressure intensity does not exceed the eighth pressure intensity threshold value, and close the tank deflation valve.

In an implementation, the eighth pressure intensity threshold value may refer to a preset pressure intensity numerical value, which is used to judge whether the pressure intensity inside the heating tank body is too high in the heating process, such that when the pressure intensity is too high, it is convenient to open the tank deflation valve, so as to reduce the pressure intensity inside the heating tank body to prevent the excessive pressure intensity and resultant danger. For example, the eighth pressure intensity threshold value may be 410 KPa.

In practical application, alcohol may turn into alcohol steam in the heating process, which increases the pressure intensity inside the heating tank body, and therefore in the process of controlling the heater to heat the heating tank body, the pressure intensity inside the heating tank body may also be monitored in real time depending upon a tank pressure intensity sensor. In an implementation, the control module may detect the pressure intensity situation inside the heating tank body in real time. If the tank body pressure intensity exceeds the eighth pressure intensity threshold value, the control module may control the tank deflation valve to open so as to reduce the internal pressure intensity of the heating tank body, until the tank body pressure intensity is reduced below the eighth pressure intensity threshold value, in which case the control module may control the tank deflation valve to close and stop deflating, and the control module continues to detect the temperature inside the heating tank body.

In addition, in addition to the above closing the tank deflation valve when it is determined that the received tank body pressure intensity does not exceed the eighth pressure intensity threshold value, after the tank deflation valve is opened, it is also possible to continue to determine whether the received tank body pressure intensity is less than a fifth pressure intensity threshold value, until the received pressure intensity threshold value is less than the fifth pressure intensity threshold value, and the tank deflation valve is closed. The fifth pressure intensity threshold value may refer to a preset pressure intensity numerical value, which is used to judge whether the pressure intensity inside the heating tank body is safe. For example, the first pressure intensity threshold value may be 390 KPa.

In one implementation of the embodiment, as shown in FIG. 2, a temperature switch is arranged inside the heater. The control module 102 in an implementation is configured to: determine whether a received heating tank body temperature exceeds a second temperature threshold value; and control, if the received heating tank body temperature exceeds the second temperature threshold value, the temperature switch to be disconnected, and feed back a temperature alarm message.

In an implementation, the temperature switch is configured to stop heating forcibly when the heater is abnormal and cannot be turned off normally. The second temperature threshold value may be a preset numerical value, which is used to determine whether the temperature inside the heating tank body is an abnormal temperature value. The second temperature threshold value is set higher than the first temperature threshold value, e.g. 121° C.

If it is detected by the control module that the heating tank body temperature exceeds the second temperature threshold value, it means that the temperature inside the heating tank body is abnormally high. In this case, the control module may control the temperature switch to be disconnected and feed back the temperature alarm message, such that the operator can learn that the heater in the heating tank body may malfunction and has been turned off forcibly, thereby enabling the operator to take corresponding measures to deal with it in time, improving safety.

In practical application, the heater selects a heating rod which adopts 220 VAC power supply and has a power of 1 KW or above. Placed inside the heater is a temperature switch, which has a disconnection temperature of the second temperature threshold value, e.g. 121° C., and a recovery temperature of the first temperature threshold value, e.g. 119° C., for avoiding the temperature of the heating tank body from being too high. The tank temperature sensor may be a PT100 temperature sensor, which is configured to measure the temperature inside the heating tank body, the measurement range being 0° C. to 150° C. The tank pressure sensor may be powered at 24 V, outputs a current signal of 4 to 20 mA, and performs measurement in a range of 0 to 0.4 MPa.

In addition, the heating tank body may have a heating control strategy in that the control module sends a heating command to the heater, and if the heater does not receive the heating command sent by the control module within 5 seconds, the heater may actively stop heating.

Figure 4:
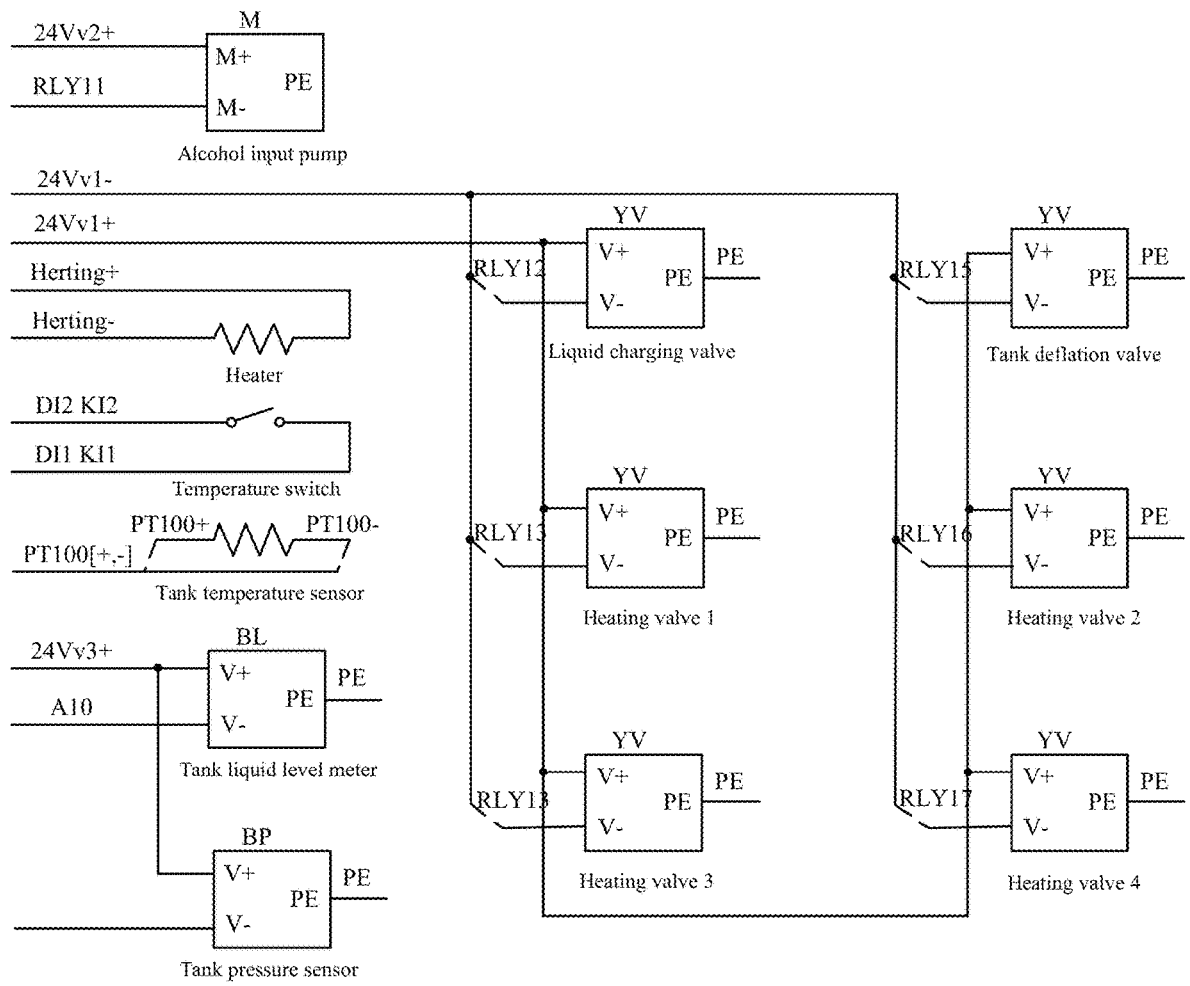
FIG. 4 is an electrical schematic diagram of a heating working medium perfusion module provided by an embodiment of the disclosure.

In an implementation, FIG. 4 is an electrical schematic diagram of a heating working medium perfusion module provided by an embodiment of the disclosure. As shown in FIG. 4, the heating working medium perfusion module includes an alcohol input pump, a heater, a temperature switch, a tank temperature sensor, a tank liquid level meter, a tank pressure sensor, a liquid charging valve and a tank deflation valve. Correspondingly, a valve box includes four heating valves (i.e., working medium output valves corresponding to the heating working medium perfusion module). In the drawing, M represents a motor, YV represents solenoid valves, BP represents a pressure sensor, BL represents a liquid level meter, PE represents grounding pins, RLY11-17 represent relays for the input of digital control signals, AIO-1 represent the input of analog value signals, Herting+ represents a positive pole of an input alternating current, Herting− represents a negative pole of the input alternating current, DI1 KI1 and DI2 KI2 represent input digital value control signals, PT100 represents a temperature sensor, and PT100+ and PT100− respectively represent a positive power supply and a negative power supply of the tank temperature sensor. In addition, 24Vv1, 24Vv2 and 24Vv3 respectively represent 24V input currents of different channels. As shown in FIG. 4, the liquid charging valve, the tank deflation valve and four heating valves serve as one channel of 24V input current (24Vv1), the alcohol input pump serves as one channel of input current (24Vv2), and the tank pressure sensor and the tank liquid level meter serve as one channel of current (24Vv3).

In one implementation of the embodiment, as shown in FIG. 2, the valve box 108 also includes a temperature feeler interface and a thermocouple acquisition board. The temperature feeler interface is configured to be connected with a temperature feeler, which is internally provided with thermocouple temperature measurement points. The thermocouple acquisition board is connected with the temperature feeler to acquire and send a temperature measured by the thermocouple temperature measurement points to the control module.

The valve box is mainly used to control the output of refrigeration and heating working medium. The valve box may be configured to be connected with the temperature feeler. The temperature feeler may assist in measuring the temperature distribution around an ice ball during a surgery and provide feedback, such that the operator can more conveniently observe the temperature distribution and variation around a tumor, so as to help the operator better manipulate his/her device to comprehensively kill cancer cells.

As for the ice ball, in the normal operation process of the device, the refrigeration working medium (liquid nitrogen) carries out heat exchange on target tissue to form an "ice ball", so as to kill the cancer cells. The temperature feeler may be inserted into the tissue in the same direction as the ablation probe or at a certain inclination angle. One to four temperature measurement points are laid out on the surface of the temperature feeler, which may detect and feed back a temperature around the ice ball or the tissue to the thermocouple acquisition board in the valve box, and the thermocouple acquisition board may feed the temperature back to the control module, depending upon which it can be fed back to an interactive module for display, thereby facilitating observation by the operator.

Figure 5:
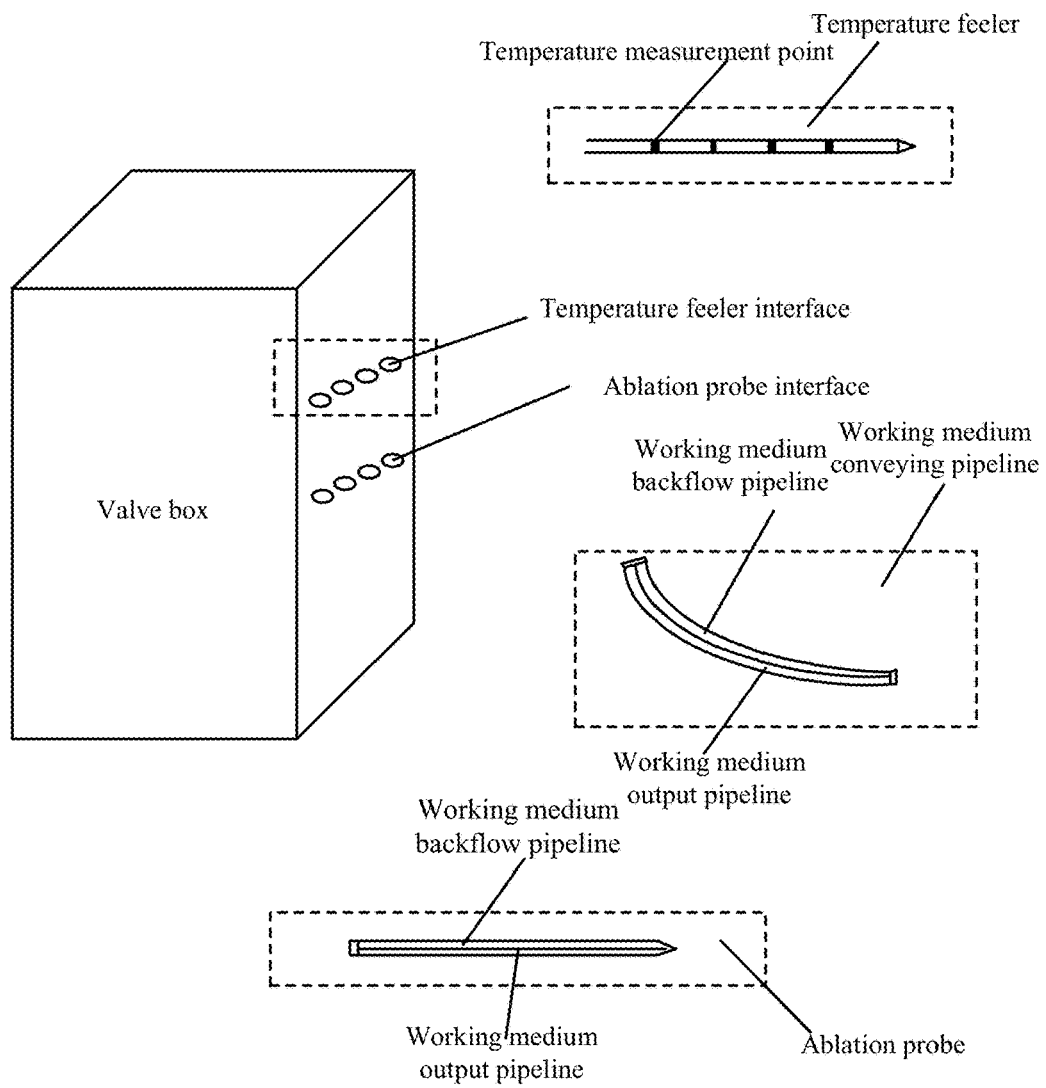
FIG. 5 is a schematic structural diagram of a valve box provided by an embodiment of the disclosure.

In an implementation, FIG. 5 is a schematic structural diagram of a valve box provided by an embodiment of the disclosure. As shown in FIG. 5, four temperature feeler interfaces are arranged on the valve box. The four temperature feeler interfaces may be configured to be connected with four temperature feelers, each of which is provided with one to four temperature measurement points (taking four as an example in FIG. 5).

In one implementation of the embodiment, as shown in FIG. 2, the valve box 108 also includes an ablation probe interface, an ablation probe inlet temperature sensor, an ablation probe backflow temperature sensor and a probe conveying pipe insertion detection switch. The ablation probe interface is configured to be connected with a working medium conveying pipeline, which is configured to be connected with an ablation probe, and the working medium conveying pipeline and the ablation probe each include a working medium output pipeline and a working medium backflow pipeline. The probe conveying pipe insertion detection switch is configured to detect whether the working medium conveying pipeline is interfaced with the ablation probe interface, and feed back, when it is detected the working medium conveying pipeline is not interfaced with the ablation probe interface, a prompt message for interfacing by means of the control module. The ablation probe inlet temperature sensor is configured to detect and send an output temperature of the working medium conveying pipeline to the control module. The ablation probe backflow temperature sensor is configured to detect and send a backflow temperature of the working medium backflow pipeline to the control module.

Refrigeration and heating working medium stored in the working medium storage tanks in the working medium perfusion modules may be output into the ablation probe, and the operator may operate the ablation probe to treat the tumor, so as to achieve a therapeutic purpose. The ablation probe may be connected to the ablation probe interface of the valve box via the working medium conveying pipeline. There are two pipelines divided in each of the working medium conveying pipeline and the ablation probe, where one of the two pipelines is the working medium output pipeline, the other one of the two pipelines is the working medium backflow pipeline. After the working medium conveying pipeline and the ablation probe are connected, the working medium output pipeline of the working medium conveying pipeline communicates with the working medium output pipeline of the ablation probe, and the working medium backflow pipeline of the working medium conveying pipeline communicates with the working medium backflow pipeline of the ablation probe. The working medium output from the working medium storage tanks flow to the working medium output pipeline in the ablation probe via the working medium output pipeline of the working medium conveying pipeline, and after flowing to a probe tip of the ablation probe via the working medium output pipeline, they flow back to the working medium backflow pipeline of the working medium conveying pipeline via the working medium backflow pipeline of the ablation probe, so as to flow back to the device for recycling.

In practical application, the probe conveying pipe insertion detection switch may be located at the ablation probe interface to detect whether the working medium conveying pipeline is connected in place. After the working medium conveying pipeline is connected in place, the probe conveying pipe insertion detection switch may send a successful connection signal to the control module. After receiving the signal, the control module determines that the working medium conveying pipeline is successfully interfaced with the ablation probe interface, and the subsequent therapeutic process may be continued.

In an implementation, a magnetic ring may be arranged at the front end of the working medium conveying pipeline, and the probe conveying pipe insertion detection switch arranged at the ablation probe interface may be a magnetic ring detector. After the working medium conveying pipeline is interfaced with the ablation probe interface, the magnetic ring detector may detect the magnetic ring, generate a successful connection signal, and transmit it to the control module, in which case it is detected by the control module that the working medium conveying pipeline is normally interfaced with the ablation probe interface.

In an implementation, as shown in FIG. 5, the valve box may also be provided with four ablation probe interfaces. The four ablation probe interfaces may be used to be connected with four working medium conveying pipelines, which may be used to be connected with four ablation probes. Each of the working medium conveying pipelines or each of the ablation probes includes a working medium output pipeline and a working medium backflow pipeline.

In an implementation, an electrical control system for minimally invasive tumor therapies may be connected with a plurality of ablation probes, and in the actual process of a therapeutic surgery, there is a difference in sizes of ice balls output from the multiple ablation probes. Especially when there are only two ablation probes, the problem is very obvious. In order to solve this problem, the disclosure realizes that the sizes of the output ice balls are controllable by transforming the working medium output valves (i.e., refrigeration valves) included in the valve box into proportioning valves.

In one implementation of the embodiment, the working medium output valves are proportioning valves. The control module in an implementation is configured to: determine, in the case of connecting two ablation probes, whether backflow temperatures of the two ablation probes fall within a first temperature interval simultaneously, and control, if the backflow temperatures of the two ablation probes fall within the first temperature interval simultaneously, the proportioning valves corresponding to the two ablation probes to open to a preset proportion; determine, if the backflow temperatures of the two ablation probes do not fall within the first temperature interval simultaneously, whether the backflow temperatures of the two ablation probes fall within a second temperature interval simultaneously, and adjust, if the backflow temperatures of the two ablation probes fall within the second temperature interval simultaneously, the proportioning valve corresponding a ablation probe with a lower backflow temperature in the two ablation probes according to a temperature difference between the backflow temperatures of the two ablation probes; and determine, if the backflow temperatures of the two ablation probes do not fall within the second temperature interval simultaneously, whether the backflow temperatures of the two ablation probes fall within a third temperature interval simultaneously, and adjust, if the backflow temperatures of the two ablation probes fall within the third temperature interval simultaneously, the proportioning valve corresponding to the ablation probe with the lower backflow temperature in the two ablation probes according to a temperature difference between the backflow temperatures of the two ablation probes.

In an implementation, the first temperature interval, the second temperature interval and the third temperature interval may refer to preset temperature ranges. Any temperature value in the temperature range of the first temperature interval is greater than that of the second temperature interval, and any temperature value in the temperature range of the second temperature interval is greater than that of the third temperature interval. For example, the first temperature interval may be greater than minus 100° C., the second temperature interval may be minus 140° C. to minus 100° C., and the third temperature interval may be minus 196° C. to minus 140° C.

In the case of connecting two ablation probes, it may determine whether the backflow temperatures of the two ablation probes fall within the first temperature interval simultaneously. If the backflow temperatures of the two ablation probes fall within the first temperature interval simultaneously, it means that the backflow temperatures of the two ablation probes are relatively high, and even if there is a temperature difference between the backflow temperatures of the two ablation probes, the sizes of the output ice balls will not be significantly different. In this case, the proportioning valves corresponding to the two ablation probes can therefore be directly controlled to open to a preset proportion, rather than adjusting the proportioning valves, where the preset proportion may refer to a proportion that is set in advance, e.g. 100%.

Additionally, in an implementation, if the backflow temperatures of the two ablation probes do not fall within the first temperature interval simultaneously, it may determine whether the backflow temperatures of the two ablation probes fall within the second temperature interval simultaneously. If the backflow temperatures of the two ablation probes fall within the second temperature interval simultaneously, it means that the backflow temperatures of the two ablation probes are relatively low. If there is a relatively large temperature difference between the backflow temperatures of the two ablation probes, it means that the output ice balls may be significantly different, in which case the proportioning valve corresponding to one ablation probe with a lower backflow temperature in the two ablation probes may be adjusted according to the temperature difference between the backflow temperatures of the two ablation probes, so as to adjust the sizes of the output ice balls.

Furthermore, in an implementation, if the backflow temperatures of the two ablation probes do not fall within the second temperature interval simultaneously, it may determine whether the backflow temperatures of the two ablation probes fall within the third temperature interval simultaneously. If the backflow temperatures of the two ablation probes fall within the third temperature interval simultaneously, it means that the backflow temperatures of the two ablation probes are relatively low. If there is a relatively large temperature difference between the backflow temperatures of the two ablation probes, it means that the output ice balls can be significantly different, in which case the proportioning valve corresponding to one ablation probe with a lower backflow temperature in the two ablation probes may be adjusted according to the temperature difference between the backflow temperatures of the two ablation probes, so as to adjust the sizes of the output ice balls.

In an implementation, in the case of connecting a number of ablation probes other than two, the proportioning valves corresponding to the ablation probes can then be directly controlled to open to a preset proportion without adjustment.

In one implementation of the embodiment, the control module is further configured to: determine whether the first temperature difference between the backflow temperatures of the two ablation probes is greater than or equal to a first difference threshold value; control, if the first temperature difference between the backflow temperatures of the two ablation probes is greater than or equal to the first difference threshold value, the proportioning valve corresponding to one ablation probe with a lower backflow temperature in the two ablation probes to reduce its opening by a numerical value corresponding to the first temperature difference; or control, if the first temperature difference between the backflow temperatures of the two ablation probes is not greater than or equal to the first difference threshold value, the proportioning valve corresponding to the ablation probe with the lower backflow temperature in the two ablation probes to reduce its opening by a numerical value corresponding to the first difference threshold value.

In an implementation, the first difference threshold value may refer to a preset temperature threshold value, which is used to judge whether the first temperature difference between the backflow temperatures of the two ablation probes is too large, and for example, the first difference threshold value may be 20° C.

In practical application, if the backflow temperatures of the two ablation probes fall within the second temperature interval simultaneously, it may determine whether the first temperature difference between the backflow temperatures of the two ablation probes is greater than or equal to the first difference threshold value before adjusting the proportioning valve corresponding to one ablation probe with a lower backflow temperature in the two ablation probes according to the temperature difference between the backflow temperatures of the two ablation probes. If the first temperature difference between the backflow temperatures of the two ablation probes is greater than or equal to the first difference threshold value, it means that there is a relatively large difference between the backflow temperatures of the two ablation probes, in which case the proportioning valve corresponding to the ablation probe with the lower backflow temperature in the two ablation probes may be controlled to reduce its opening by a numerical value corresponding to the first temperature difference. The numerical value corresponding to the first temperature difference may be pre-stored, and for example, the numerical value corresponding to the first temperature difference 22° C. may be preset to 22%. That is, the proportioning valve corresponding to the ablation probe with a lower backflow temperature may be controlled to reduce its opening by 22%.

If the first temperature difference between the backflow temperatures of the two ablation probes is not greater than or equal to the first difference threshold value, it means that there is no large difference between the backflow temperatures of the two ablation probes, in which case the proportioning valve corresponding to one ablation probe with a lower backflow temperature in the two ablation probes may be directly controlled to reduce its opening by a numerical value corresponding to the first difference threshold value. The numerical value corresponding to the first difference threshold value may be pre-stored, and for example, the numerical value corresponding to the first difference threshold value 20° C. may be preset to 20%. That is, if the first temperature difference between the backflow temperatures of the two ablation probes is 15° C., the proportioning valve corresponding to the ablation probe with a lower backflow temperature may be controlled to reduce its opening by 20%.

In addition, if the backflow temperatures of the two ablation probes fall within the third temperature interval simultaneously, according to the temperature difference between the backflow temperatures of the two ablation probes, the proportioning valve corresponding to one ablation probe with a lower backflow temperature in the two ablation probes is adjusted in a manner that is similar to the adjusting manner adopted when the backflow temperatures of the two ablation probes fall within the second temperature interval simultaneously, which will not be described herein.

The backflow temperatures of the ablation probes may indicate the sizes of the ice balls, and thus the corresponding proportioning valves may be adjusted based on the backflow temperatures of the ablation probes, so as to adjust the sizes of the output ice balls, thereby avoiding the sizes of the ice balls output from different ablation probes from being significantly different. Therefore, after the proportional output valves are adjusted, the backflow temperatures of the ablation probes may continue to be monitored, so as to determine whether the proportioning valves need to continue to be adjusted.

In one implementation of the embodiment, as shown in FIG. 2, the system also includes a working medium recovery module 110. The working medium recovery module 110 includes a working medium backflow port, a heat regenerator and a working medium output port. A liquid storage cup is arranged below the working medium output port, and a weighing sensor is arranged below the liquid storage cup. The working medium backflow port and the working medium output port are located at different ports of the heat regenerator, and working medium flowing back from a working medium backflow pipeline in an ablation probe enter the heat regenerator via the working medium backflow port, and are output from the working medium output port. The liquid storage cup is configured to store liquid output from the working medium output port. The weighing sensor is configured to measure and feed back the weight of stored liquid in the liquid storage cup to the control module. The control module in an implementation is configured to receive the weight of the stored liquid fed back by the weighing sensor, and feed back a stored liquid alarm message when the weight of the stored liquid is greater than a weight threshold value.

The heating working medium may enter the heat regenerator via the working medium backflow pipeline through the working medium backflow port arranged on the heat regenerator to turn from a gas state into a liquid state in the heat regenerator, and therefore a liquid storage cup needs to be arranged below the working medium output port. A weighing sensor is arranged at the lower end of the liquid storage cup and may detect and feed back the weight of the stored liquid, such that the control module may feed back a stored liquid alarm message when the weight of the stored liquid is greater than the weight threshold value, so as to remind the operator to clear the liquid storage cup. The refrigeration working medium may also enter the heat regenerator via the working medium backflow pipeline through the working medium backflow port arranged on the heat regenerator to turn from the liquid state into the gas state after performing heat exchange in the heat regenerator, and then is directly discharged from the working medium output port.

In an implementation, when the weight of the stored liquid is greater than the weight threshold value, the control module may feed back the stored liquid alarm message in a manner that the alarm message is displayed on a display of an interactive module, or in a manner of controlling a light strip on the interactive module to flash.

In one implementation of the embodiment, as shown in FIG. 2, the working medium recovery module 110 also includes a fan. The fan is arranged close to the heat regenerator. A recovery temperature sensor is arranged at the working medium backflow port. The recovery temperature sensor is configured to measure the working medium recovery temperature of the working medium backflow port, and feed it to the control module. The control module in an implementation is configured to receive the working medium recovery temperature, and control the fan to start to work when the working medium recovery temperature is higher than a third temperature threshold value or lower than a fourth temperature threshold value.

The fan may be controlled by means of feedback of the recovery temperature sensor. The recovery temperature sensor may be arranged at the working medium backflow port to measure the working medium recovery temperature of the working medium backflow port. When the working medium recovery temperature is higher than the third temperature threshold value or lower than the fourth temperature threshold value, the control module may control the fan to be turned on to blow against fins of the heat regenerator, so as to prevent the temperature of the heat regenerator from being too low or too high, and in one implementation, to prevent alcohol steam from being discharged into air due to the excessively high temperature of the heat regenerator.

In one implementation of the embodiment, as shown in FIG. 2, the working medium recovery module 110 also includes a liquid storage drawer and a limit switch. The liquid storage drawer is configured to place the liquid storage cup. The limit switch is configured to detect whether placement of the liquid storage cup is completed, and when it is detected that the placement of the liquid storage cup is completed, feed back a prompt of meeting surgical conditions depending upon the control module.

The liquid storage cup is an apparatus only for containing the heating working medium. The liquid storage cup may be placed on the liquid storage drawer. When the liquid storage drawer does not hit the limit switch, the control module considers that the surgical conditions are not met, and the state will be displayed on the display of the interactive module by popping up to remind the operator to place the liquid storage cup in place. When the liquid storage drawer hits the limit switch, the control module considers that the surgical conditions are now met, and the prompt of meeting the surgical condition will be displayed on the display of the interactive module by popping up to remind the operator to carry out a surgery.

Figure 6:
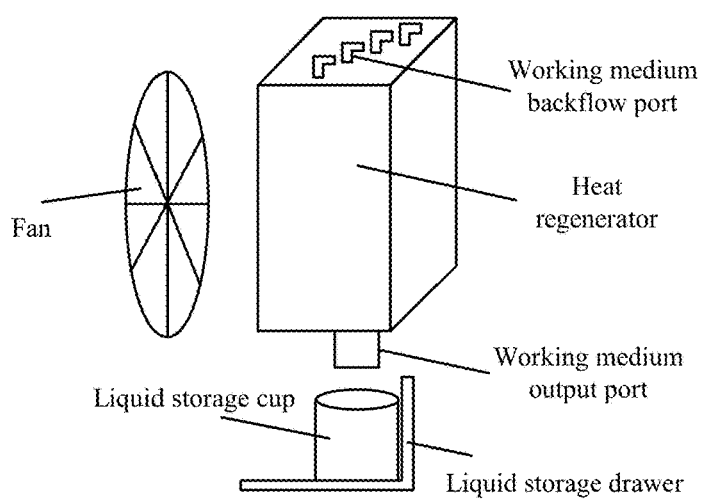
FIG. 6 is a schematic structural diagram of a working medium recovery module provided by an embodiment of the disclosure.

In an implementation, FIG. 6 is a schematic structural diagram of a working medium recovery module provided by an embodiment of the disclosure. As shown in FIG. 6, four working medium backflow ports are arranged at the upper end of a heat regenerator. The working medium backflow ports are connected with four ablation probe interfaces to recover working medium flowing back from the ablation probes. A working medium output port is arranged at the lower end of the heat regenerator. The liquid storage cup is arranged below the working medium output port. The liquid storage cup is arranged on the liquid storage drawer. A fan is arranged close to the heat regenerator to blow against the heat regenerator.

In one implementation of the embodiment, as shown in FIG. 2, the system also includes an interactive module 112. The interactive module 112 includes a motion control handle and a motion grip. The power box also includes a battery and a motion control unit, and the motion control unit includes a motion control board and a power wheel. The battery is configured to supply power to the motion control unit. The motion control board is configured to detect the gear state of the motion grip and the position state of the motion control handle, and control the motion state of the power wheel according to the gear state and the position state.

The battery may output a 24 V current as a power supply for the motion control unit (mainly for device movement assistance and electronic braking) to supply power to the motion control unit. The motion control unit as a core control component drives the power wheel by receiving a movement control command for the interactive module including the motion control handle and the motion grip, so as to complete a corresponding motion instruction.

In practical application, the motion control handle includes two position states of pressing down and lifting up. The motion grip includes three gear states of forward, neutral and reverse. Different position states and different gear states may be used to control the power wheel to be in different motion states.

In one implementation of the embodiment, the motion control board is further configured to: control the motion state of the power wheel to be a neutral state when it is detected that the gear state is the neutral state; control the motion state of the power wheel to be a stopping state when it is detected that the position state is a lifting-up state, and in the stopping state, control the motion state of the power wheel to be a rising state when it is detected that a position signal of the power wheel is at a high electrical level; control the motion state of the power wheel to be a descending state when it is detected that the gear state is a non-neutral state and the position state is a pressing-down state, and set the position signal of the power wheel into a high electrical level when it is detected that descending of the power wheel is completed; and control the motion state of the power wheel to be a lower-position brake state when it is detected that the gear state is the non-neutral state, the position state is the pressing-down state, and the position signal is at the high electrical level, control the motion state of the power wheel to be an advance state if it is detected that the gear state is an advance gear, and control the motion state of the power wheel to be a reverse state if it is detected that the gear state is an reverse gear.

In practical application, the power wheel may be in a retracting state and an extending state. When the power wheel is in the retracting state, the device is immovably fixed at the current position. When the power wheel is in the extending state, the device can be moved forward, backward, etc. by means of the power wheel.

Figure 7:
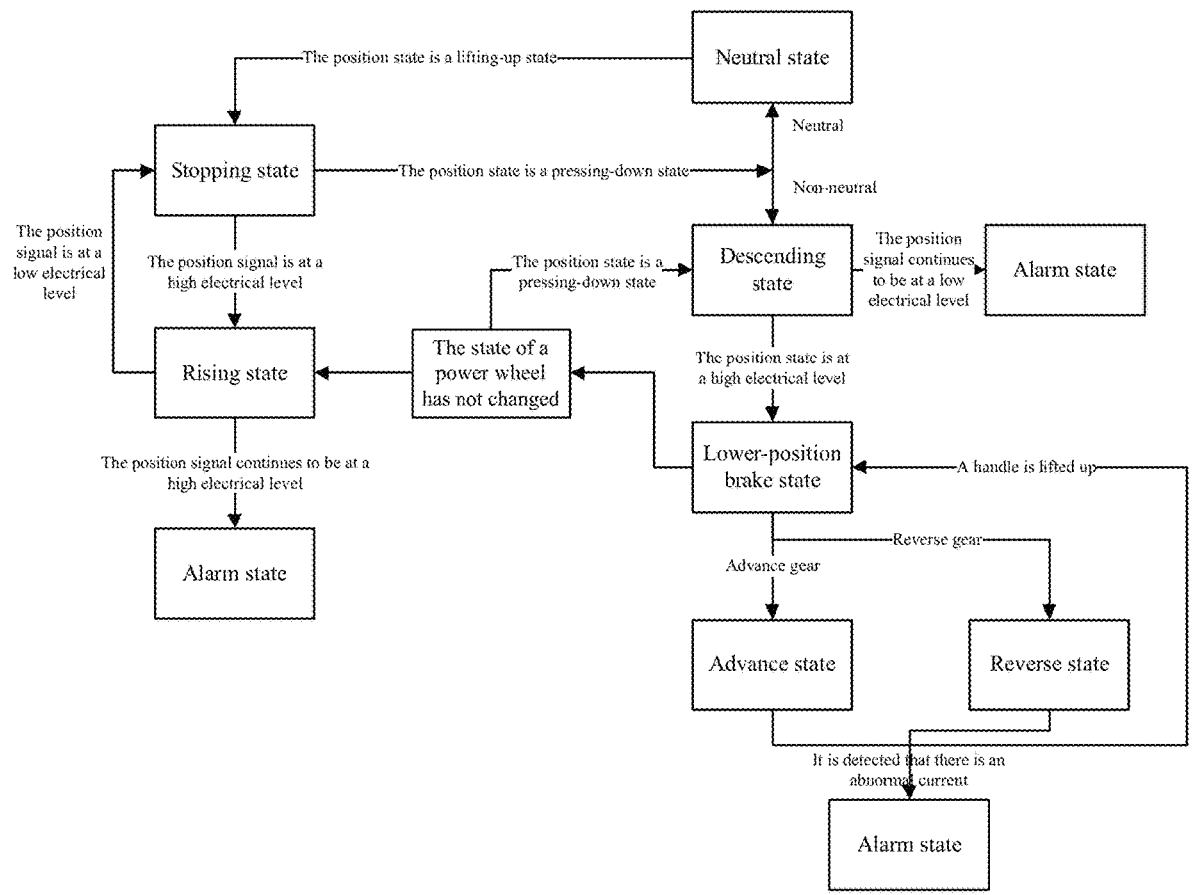
FIG. 7 is a schematic diagram of switching of motion states of a power wheel provided by an embodiment of the disclosure.

FIG. 7 is a schematic diagram of switching of motion states of a power wheel provided by an embodiment of the disclosure. As shown in FIG. 7, when it is detected that the gear state is a neutral state, the motion state of the power wheel may be controlled to be the neutral state. In this case, the power wheel is in a retracting state, the power wheel is universal, and the power wheel keeps in the retracting state and does not move, that is, it does not rise or descend. Then, if it is detected that the position state is a lifting-up state, the motion state of the power wheel is controlled to be a stopping state. In the stopping state, the power wheel is still in the retracting state, the power wheel is fully locked, and the power wheel keeps in the retracting state and does not move, that is, it does not rise or descend. In the stopping state, if it is detected that the position signal of the power wheel is at a high electrical level, that is, it is detected that the power wheel is in an extending state, the motion state of the power wheel may now be controlled to be a rising state, i.e., retracting the power wheel.

When it is detected that gear state is a non-neutral state and the position state is a pressing-down state, it means that it may be necessary to move the device. In this case, the motion state of the power wheel may be controlled to be a descending state, so as to extend the power wheel. When it is detected that descending of the power wheel is completed, the position signal of the power wheel is set to be at a high electrical level, that is, when the position signal of the power wheel is at the high electrical level, it represents that the power wheel is extended, and when the position signal of the power wheel is at a low electrical level, it represents that the power wheel is retracted.

When it is detected that the gear state is a non-neutral state, the position state is a pressing-down state, and the position signal is at the high electrical level, it means that the power wheel has been extended, but the moving direction is not given. In this case, the motion state of the power wheel may therefore be controlled to be a lower-position brake state, that is, the power wheel may move universally, but it does not move and waits for a moving instruction.

Subsequently, if it is detected that the gear state is an advance gear, it means that an advance instruction is received, in which case the motion state of the power wheel is controlled to be an advance state, and the power wheel moves forwards. If it is detected that the gear state is a reverse gear, it means that a reverse instruction is received, in which case the motion state of the power wheel is controlled to be a reverse state, and the power wheel moves backwards.

In one implementation of the embodiment, the motion control board is further configured to: store and feed back a power wheel alarm message, if it is detected that the position signal of the power wheel is at a low electrical level after the motion state of the power wheel is controlled to be a descending state for a fifth preset duration; control the motion state of the power wheel to be a rising state, if it is detected that the motion state of the power wheel has not changed after the motion state of the power wheel is controlled to be a lower-position brake state for a sixth preset duration; set the position signal of the power wheel to be at the low electrical level when it is detected that rising of the power wheel is completed, and store and feed back a power wheel alarm message, if it is detected that the position signal is at a high electrical level after a seventh preset duration; and store and feed back the power wheel alarm message, if it is detected that there is an abnormal current in the power wheel.

In practical application, as shown in FIG. 7, after the motion state of the power wheel is controlled to be the descending state for the fifth preset duration, the power wheel should be extended successfully, in which case the position signal of the power wheel should be at the high electrical level. However, if it is detected that the position signal of the power wheel continues to be at the low electrical level, it means that the power wheel may be faulty and has not descended successfully, that is, the power wheel cannot be extended successfully, in which case the motion control board may control the power wheel to be in an alarm state, and may store and feed back the power wheel alarm message.

In addition, the lower-position brake state is a state of waiting for moving. If, after the motion state of the power wheel is controlled to be the lower-position brake state for the sixth preset duration, it is detected that such a motion state of the power wheel has not changed, it means that after the power wheel is extended, a moving instruction is not received within a period of time, which indicates that it may be not necessary to move the device, in which case the motion state of the power wheel may be controlled to be the rising state, i.e., retracting the power wheel. When it is detected that rising of the power wheel is completed, the position signal of the power wheel is set to be at the low electrical level. After the seventh preset duration, the power wheel should be retracted successfully, that is, the position signal of the power wheel should be at the low electrical level. If, after the seventh preset duration, it is detected that the position signal continues to be at the high electrical level, it means that the power wheel may be faulty and has not been not retracted successfully, in which case the motion control board may control the power wheel to be in an alarm state, and may store and feed back a power wheel alarm message.

Furthermore, if it is detected that there is an abnormal current in the power wheel, the motion control board may also control the power wheel to be in the alarm state, and may store and feed back the power wheel alarm message.

In one implementation of the embodiment, the power wheel is internally provided with a power motor and a lifting motor. The motion control board in an implementation is configured to determine whether there is an abnormal current in the power motor and the lifting motor; and stop supplying power to the power motor and the lifting motor when the current is abnormal, and store and feed back a power wheel alarm message.

In one implementation of the embodiment, the interactive module also includes an emergency stop button. The motion control board in an implementation is configured to control the motion state of the power wheel to be a lower-position brake state when it is detected that the emergency stop button is pressed down, and store and feed back an emergency stop alarm message.

The interactive module also includes the emergency stop button, which may be pressed down in case of an emergency to control the device to stop moving, thereby improving safety. Therefore, when it is detected by the motion control board that the emergency stop button is pressed down, it may control the motion state of the power wheel to be the lower-position brake state, i.e., stopping it from continuing to move, and may store and feed back the emergency stop alarm message.

Figure 8:
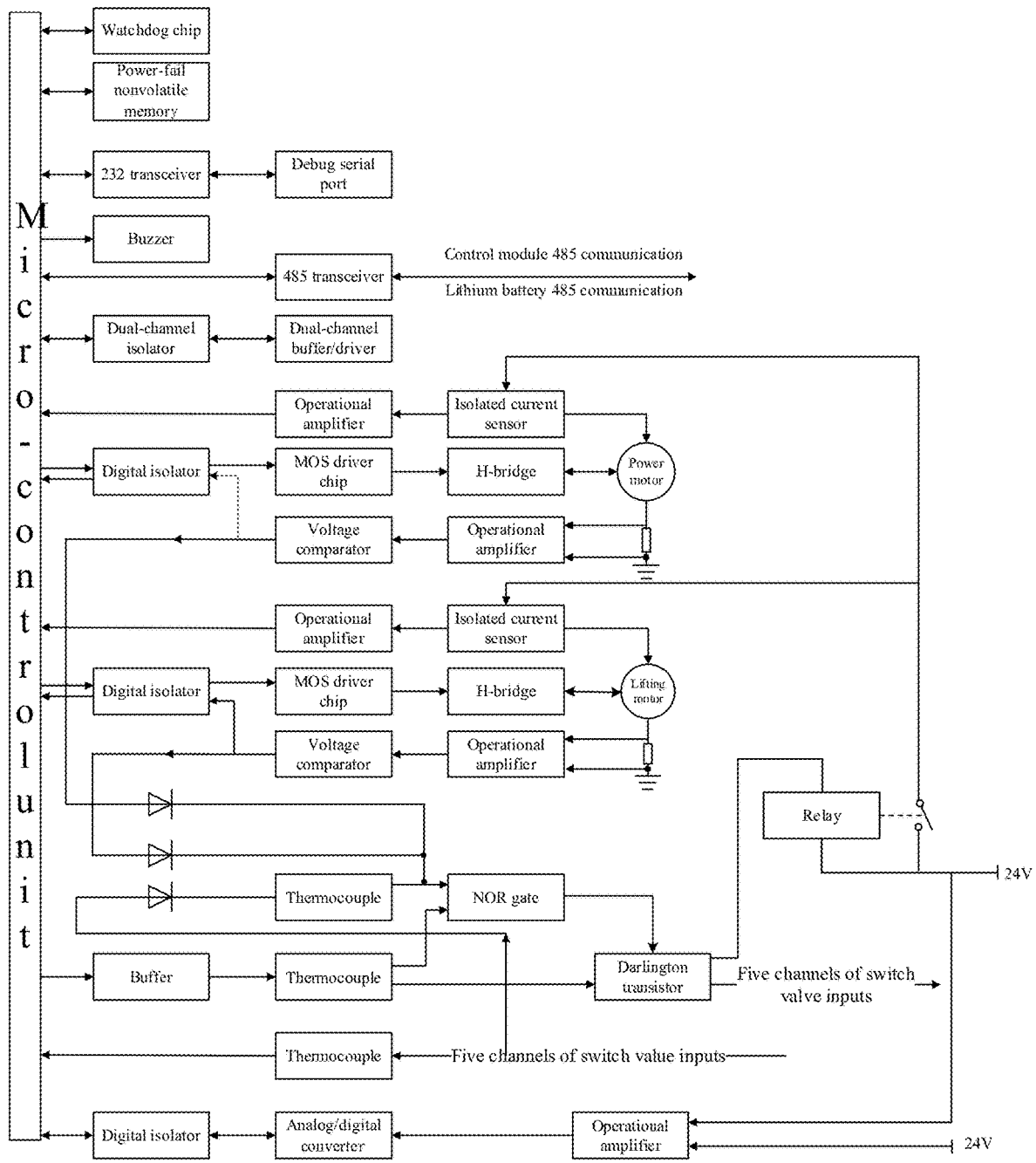
FIG. 8 is a schematic structural diagram of a motion control unit provided by an embodiment of the disclosure.

In an implementation, FIG. 8 is a schematic structural diagram of a motion control unit provided by an embodiment of the disclosure. As shown in FIG. 8, a watchdog chip is configured to prevent program fleet, and has an address recognition function to achieve uniqueness recognition of a plug board. A power-down nonvolatile memory is configured to achieve a parameter storage function; a RS-232 transceiver achieves the function of RS-232 communication of one channel, and may be connected with a debug serial port to debug the system. A RS-485 transceiver achieves the function of RS-485 communication of two channels, where one of the two channels communicates with the control module, and the other channel communicates with the battery. In addition, the motion control unit has a function of detecting a 24 V power supply, so as to confirm whether the power motor and the lifting motor are powered on using a 24 V power supply. The motion control unit has a structure composed of a voltage comparator and an isolated communication chip (i.e., an isolated current sensor), with two isolated channels for motor control (which are power motor control and lifting motor control respectively). Furthermore, the motion control unit also includes an H-bridge (one being the power motor, the other being the lifting motor) composed of the isolated communication chip (i.e., the isolated current sensor), an MOS driver chip and an MOS transistor. The motion control unit has a current feedback function, adopts a HALL chip for isolated detection on a current (i.e., an isolated current sensor) to adjust the torque, i.e., speed, by adjusting the current, and has functions of locked-rotor detection and protection. Once overcurrent occurs, the output of a power supply for motion control will be cut off (that is, the power supply of the power motor and the lifting motor will be cut off), while informing the control module.

In practical application, as shown in FIG. 8, once overcurrent occurs, the power motor and the lifting motor may stop from being powered for overcurrent protection, while informing the control module to display an alarm message by means of the display of the interactive module. In an implementation, it is shown upon actual measurement that the locked-rotor current of the power motor is greater than 25 A, and the locked-rotor current of the lifting motor is greater than 10 A. Current values of the two motor are converted into voltage signals of 0 to 1.5 V by means of an operational amplifier and then compared by means of a voltage comparator. If it exceeds 1.35 V, it is considered to exceed a normal value, and it may be judged that the motors are locked-rotor. In order to prevent signal interference, 52 signals are acquired each time, and values are taken. The maximum value and the minimum value are removed, and then the average of 50 values is taken. If it is judged that the motors are locked-rotor, or the emergency stop button is pressed down, a Darlington transistor signal may be given after passing through a NOR gate, relays are not pulled in, and the motors do not operate.

In one implementation of the embodiment, the motion control board is also configured to: acquire attribute parameters of the battery, and feed the attribute parameters back to the interactive module for display; determine whether the battery is abnormal according to the attribute parameters of the battery; and feed back a battery alarm message to the interactive module when the battery is abnormal.

The battery may supply power to the motion control unit. The motion control board needs to communicate with the battery, and thus the motion control board may also display the battery attribute parameters such as the battery remaining capacity, battery charging and discharging states and the battery cell situation in real time. Also, the motion control board may determine whether the battery is abnormal based on the acquired battery attribute parameters, and when the battery is abnormal, feed back the battery alarm message to the interactive module, so as to enable the operator to treat the situation of battery abnormality in time.

In an implementation, the total electric quantity of the battery may be divided into five segments which are respectively and separately controlled to indicate the electric quantity of the battery. For example, if the current electric quantity is 60%, only three segments of indicator lights will be illumined. If the battery is in a charging state, the charging effect will be dynamically displayed. When the system is normally started and the display normally performs display, if a charger of the battery is abnormal or the battery cell is abnormal (mainly in temperature), the display will report a corresponding fault, and an alarm message is fault content.

In practical application, the motion control board may have a storage function to store various key parameters in the motion process of the power wheel and an alarm message for query. For example, the motion control board may store the electric quantity information of the battery and parameters such as operation currents of the power motor and the lifting motor in the power wheel, and in the cases that there is an overcurrent in the power motor or the lifting motor, the lifting motor does not rise or descend in place, communication between the battery and the motion control board is abnormal, the emergency stop button is pressed down, etc., it will generate and store a corresponding alarm message.

In addition, the motion control unit may have eight channels of switching value input interfaces to achieve the detection function of motion grip, power wheel in-place switch and emergency stop button inputs. A total of eight channels may be devised during design, but there may be only five channels for practical use, and the other three channels are redundant, where three channels (advance, reverse and neutral) for the motion grip, one channel for the power wheel in-place switch and one channel for the emergency stop button are inclusive. The motion control unit may also have eight channels of switching value output interfaces to achieve control over the power wheel and the display function of the battery attribute parameters of the battery. A total of eight channels may be devised during design, but there may be only five channels for practical use, and the other three channels are redundant, where actual output control quantities are two channels of rising and descending of the lifting motor, two channels of advance and reverse of the power motor, one channel of battery attribute parameter control, i.e., five channels in total. Furthermore, the corresponding alarm message may also be generated in the cases that there is an overcurrent in the power motor or the lifting motor, the lifting motor does not rise or descend in place, communication between the battery and the motion control board is abnormal, the emergency stop button is pressed down, etc.

In the disclosure, the motion control unit is additionally arranged, such that the device may be moved easily and conveniently, and when there is an emergency, braking and emergency stop may be carried out to prevent collision of the device on a narrow slope, so as to facilitate operation and usage by the operator.

In one implementation of the embodiment, the interactive module 112 also includes a display, a function keyboard, an indicator light, a wireless communication unit and a start button. The display is configured to display an alarm message and/or a prompt message and control a surgical state. The function keyboard is configured to control the surgical state. The indicator light is configured to indicate the alarm message. The wireless communication network is configured to carry out wireless communication. The start button is configured to start the electrical control system for minimally invasive tumor therapies.

The wireless communication unit is additionally arranged in the interactive module, such that the operator may more conveniently carry out the surgery away from the device. The display and the indicator light may also display various alarm messages and prompt messages for human-machine interaction, such that the operator may learn the situation of the device in time to operate the device more conveniently.

Figure 9:
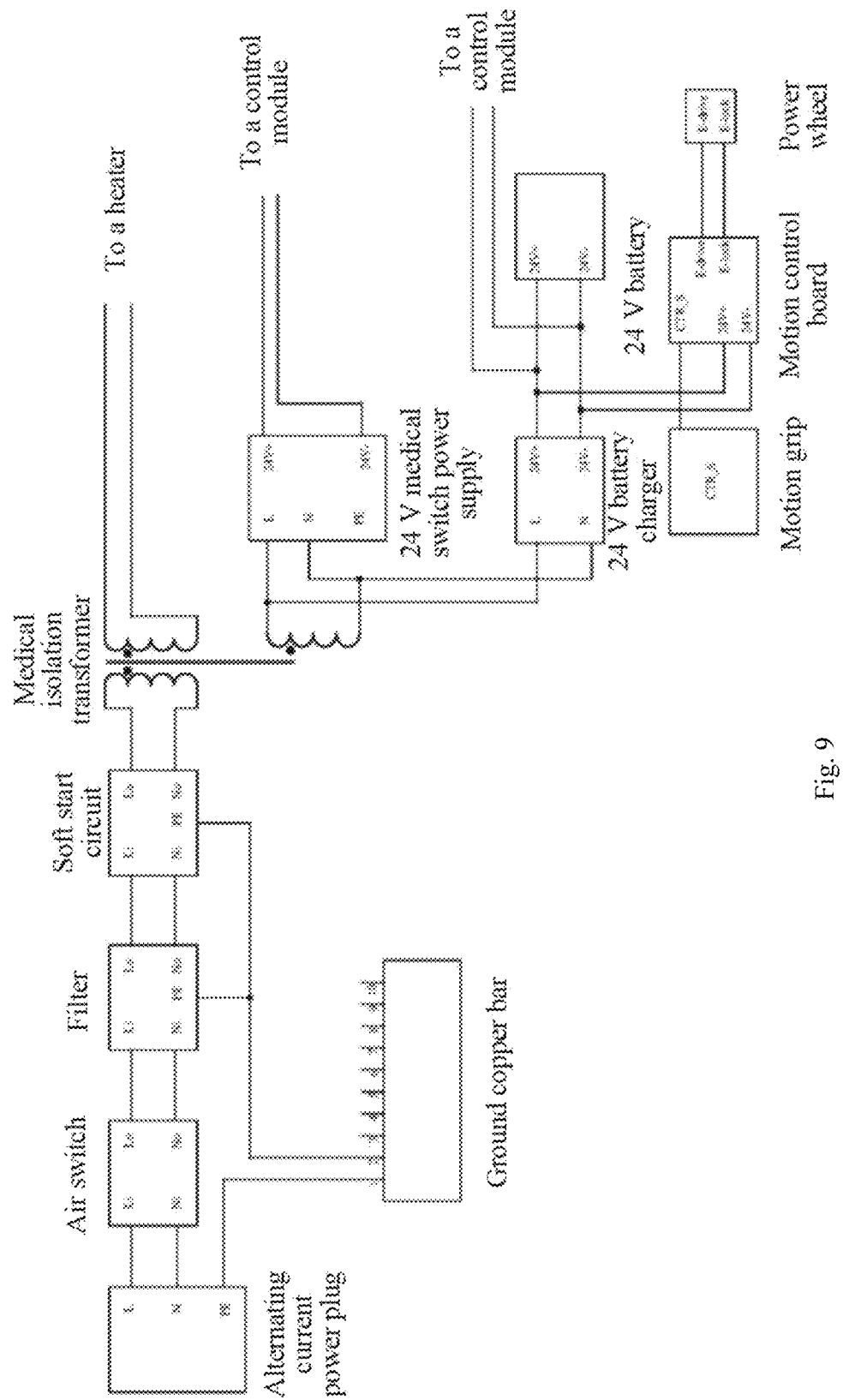
FIG. 9 is an electrical schematic diagram of a power box provided by an embodiment of the disclosure.

In one implementation of the embodiment, FIG. 9 is an electrical schematic diagram of a power box provided by an embodiment of the disclosure. As shown in FIG. 9, the power box 106 also includes an air switch, a soft start circuit and a medical isolation transformer.

The power box part has the main function of transforming into a power supply required by each subsystem from an incoming power line, and plays the role of isolation and protection, while being integrated with an industrial personal computer and a motion control system. In addition, as shown in FIG. 9, the incoming power line of the power box is an alternating current power plug. The power box also includes a filter. The alternating current power plug, the filter and the soft start circuit are each connected with a ground copper bar. The ground copper bar is configured for grounding, PE is grounding pins, L is a phase line (i.e., a live wire), and N is a neutral line (i.e., a neutral wire).

In practical application, as shown in FIG. 9, the device supplies power from a power supply of 220 V to the system by means of a power plug and a power line from the air switch (mainly playing the role of overload and short-circuit protection) to the filter (mainly playing the role of filtering out interference signals other than the specific frequency) to the soft start circuit (mainly playing the role of reducing the peak current of the isolation transformer at the power-on moment) and to the primary of the medical isolation transformer (mainly playing the role of electrical isolation of the primary side and the secondary side to ensure personal safety). The secondary of the isolation transformer is divided into two groups of power output, where one of the two groups supplies power to a 220 VAC heater (mainly playing the role of heating a heating working medium), and other one of the two groups supplies power to an AC-DC switching power supply (mainly playing the role of distributing an isolated power supply for the device) and a battery charger (mainly playing the role of charging the battery). The output 24 V1 of the switching power is used as a main power supply of the control system to supply power to the electrical system of the whole machine. The output 24 V2 of the battery is used as a standby power supply of the system to continue to supply power to the control system when there is an unexpected 220 VAC power failure.

The disclosed control module is mainly a lower computer control system composed of 11 circuit boards. This part has the main function of communicating with the industrial personal computer, performing operation of the operator, feeding back the current state of the system, and sending a prompt to the operator when the system is abnormal. In an implementation, the control module may feed the current state of the system back to the industrial personal computer, and the industrial personal computer displays specific content by means of the display, and sends a prompt message to the operator mainly in two ways that the prompt massage may pop up on a display interface in a dialog box form, or prompting may be carried out by means of a three-color LED light board.

In practical application, switching value inputs of the control module mainly include an on-off key, an emergency stop key, a liquid storage cup drawer limit switch, refrigeration tank perfusion port insertion detection, 24 V power supply indicators of a switching power supply, 5 V signals of powering on of the industrial personal computer (a 5 V voltage will be detected at a USB port after the industrial personal computer is powered on, and through such a voltage it would be known whether the industrial personal computer is powered on or not), and there are six channels in total.

Switching value outputs of the control module mainly include a phase separation valve, four refrigeration valves, a tank deflation valve, a pressurization valve, a liquid charging deflation valve and a liquid charging valve corresponding to a refrigeration working medium perfusion module, a liquid charging valve, a tank deflation valve, an alcohol input pump and four heating valves corresponding to a heating working medium perfusion module, as well as a three-color indicator light of a light strip, an on-off key indicator light, an external buzzer control, a power supply enable signal after starting the system, fans (19 V) and an industrial personal computer power supply (19 V). Therefore, the switching value output signals that need to be controlled are 22 channels of 24 V signals and 3 channels of 19 V signals. 24 V control includes the phase separation valve, the four refrigeration valves, the tank deflation valve, the pressurization valve, the liquid charging deflation valve and the liquid charging valve corresponding to the refrigeration working medium perfusion module, the alcohol input pump, the liquid charging valve, the tank deflation valve and the four heating valves corresponding to the heating working medium perfusion module, as well as the three-color indicator light of the light strip, the on-off key indicator light, the external buzzer control and the power supply enable signal after starting the system, and there are 22 channels in total. 19 V control includes two channels of fans and one channel of industrial personal computer control, and there are three channels in total.

The analog value input of the control module includes analog value signals of 4 to 20 mA, which are respectively a tank pressure sensor, a perfusion port pressure sensor and a tank liquid level meter included in the refrigeration working medium perfusion module, a tank liquid level meter and a tank pressure sensor included in the heating working medium perfusion module, and a liquid storage cup weighing sensor included in a working medium recovery module, and there are six channels of analog value input signals in total.

The control module also includes temperature acquisition signals. There are eight channels of thermocouple temperature acquisition of four working medium output ports and four working medium backflow ports. The control module also includes heating control signals, i.e., one channel of heater on-off control signal, one channel of heating current detection signal, one channel of tank temperature sensor PT100 detection signal of a heating tank, and one channel of temperature detection signal of a temperature switch. When a heater works, there will be a heating current in the whole loop, and the magnitude of the current may be measured by means of a Hall sensor.

Therefore, ten plug boards need to be designed in the control module, which include a main control board, a temperature acquisition board, a current acquisition board, four high-power output boards, two power supply boards, a heating control board and a backboard. The main control board has its main functions of a) communicating with an upper computer serial port; b) communicating with other circuit boards (a CAN bus); c) achieving the insertion detection function of all the circuit boards; d) achieving input signal detection of the on-off key and control over the on-off key indicator light; and e) achieving insertion detection of the emergency stop key, the liquid storage cup drawer limit switch and the perfusion port of the refrigeration tank and input detection of industrial personal computer power-on signals.

The temperature acquisition board has the main functions of a) achieving temperature acquisition of 12 channels of thermocouples with the temperature detection range of minus 200° C. to 100° C. and the accuracy error of less than 3° C.; b) achieving temperature acquisition of two channels of on-board PT100, and using it as temperature compensation of the 12 channels of thermocouples; and c) communicating with the main control board (the CAN bus).

The current acquisition board has its main functions of a) acquiring 16 channels of analog current signals of 4 to 20 mA; and b) communicating with the main control board (the CAN bus).

The high-power output board has its main functions that a) eight channels of switching value outputs are achieved, where the current output capacity of each channel is at least 1 A, the high-power output board mainly playing the role of output control, 24 V control and 19 V control mentioned above being both achieved by the high-power output board; b) the output of each channel has state feedback of an executive component, which is displayed by means of an output state indicator light; and c) the high-power output board communicates with the main control board (the CAN bus).

The power supply board has its main functions of a) having a switching power supply 24 V input interface (24 V1, 20 A), and having a battery 24 V power supply input interface (24 V2, 20 A); b) automatically detecting the input state of the switching power supply 24 V1, and being automatically switched to the battery 24 V2 power supply to supply power to the system when the switching power supply is powered down; and c) being capable of outputting a 19 V voltage.

The heating control board has its main functions that a) on-off control over one channel of 220 VAC heater is achieved (redundant design needs to be made to prevent adhesion of relays); b) range detection of the heater current is achieved, and the maximum heating current is 10 A; c) heating tank temperature acquisition of one channel of PT100 is achieved, where the temperature detection range is 0° C. to 150° C., and the accuracy error is less than 3° C.; d) emergency stop switch protection and heating tank temperature switch protection are achieved, that is, the heater may be controlled to stop heating when after the external emergency stop switch is pressed down or the temperature switch inside the heating tank is disconnected; and e) the heating control board communicates with the main control board (the CAN bus). The backboard has its main functions that a) the backboard is a passive circuit board without components except connector terminals; and b) BIN interfaces on the backboard provide high/low electrical levels by means of various plug boards, and use each of the high/low electrical levels as an insertion detection signal of each plug board.

24 V1 is a switching power supply (24 V), and 24 V2 is a battery (24 V). After the system is started up, a main control board needs to output an enable signal (E_OUT0) to enable a battery to serve as a standby power supply of the system. After the system is shut down, the main control board needs to turn off the enable signal (E_OUT0) to make the battery no longer be the standby power supply of the system. S0 is an automatic switching circuit. When 24V1 is normal, 24V_O1=24V1. When 24V1 is powered down, 24V_O1=24V2. The S0 switching circuit is composed of four MOS transistors and a control logic circuit, where each MOS transistor has a working current of about 20 A, a power of 1 W and a temperature rise of 60° C., and heat dissipation treatment is required (by adding cooling fins). 24V_O1 serves as a 24V main power supply in the system to directly supply power to start button, emergency stop button and other switching value inputs. U1 is an isolated DC-DC power module, and its output 24Vd1 supplies power to the main control board.

The U1 is followed by a relay K1, the output of which supplies power to other circuits in a case. After the system is started up, the main control board needs to output an enable signal (E_OUT1) to enable other circuit boards to be powered on. After the system is shut down, the main control board needs to turn off the enable signal (E_OUT1) to make the other circuit boards to be powered down. Relay K3 is a main power switch for all peripherals within the system.

Relay K4 is a power switch for all switch valves within the system and an alcohol input pump. 24V_O3 following K3 serves as a power supply for peripherals such as an alarm buzzer and a strip light (which still works after an emergency stop button is pressed down). 24V_O2 following K4 serves as a power supply for peripherals such as various switch valves and the alcohol input pump (which needs to be powered off after the emergency stop button is pressed down). E_OUT3 and E_OUT4 of K3 and K4 are controlled by the main control board. U2 is an isolated DC-DC power module, and its output 24Ve supplies power to sensors of 4 to 20 mA such as a liquid level meter and a pressure sensor. U3 is a non-isolated DC-DC output adjustable switching power circuit, which outputs 19V_O to supply power to an industrial personal computer, a fan for a heat regenerator. U4 is a non-isolated DC-DC output adjustable switching power circuit, which outputs 21.5V_O to supply power to a power supply for a flow valve (which is used for adjusting the output flow of working medium). As above, the power supply control function of the control module is achieved by a first power supply board and a second power supply board. Refrigeration tanks and their related assemblies are apparatuses for automatic refrigeration working medium adding, pressurization and protection of the system.

The disclosure provides an electrical control system for minimally invasive tumor therapies. The system includes a control module, a perfusion module and a power box. The perfusion module includes a working medium storage tank, a tank liquid level meter, a tank pressure sensor, a tank deflation valve, a liquid charging valve and an external working medium container. The power box is configured to supply power to the control module and the perfusion module. The control module is configured to receive working medium parameters sent by the tank liquid level meter and the tank pressure sensor, and when the work medium parameters meet a perfusion condition, control the tank deflation valve and the liquid charging valve to open or close respectively so as to input working medium from the external working medium container into the working medium storage tank.

In the case where the control module and the perfusion module are arranged in the electrical control system for minimally invasive tumor therapies, the tank liquid level meter and the tank pressure sensor in the perfusion module may detect relevant working medium parameters of the working medium storage tank and send them to the control module. The control module may determine whether the working medium parameters meet the perfusion condition, and when they meet the perfusion condition, automatically control the tank deflation valve and the liquid charging valve to open or close respectively, such that working medium in the external working medium container may be automatically input into the working medium storage tank, thereby achieving automatic adding of the working medium, simplifying the process of adding the working medium, saving on labor and time costs, ensuring that the working medium may be automatically and accurately added, significantly improving the timeliness, accuracy and efficiency of adding the working medium.

In addition, the system also includes a motion control unit, such that a device may be moved easily and conveniently, and when there is an emergency, braking and emergency stop may be carried out to prevent collision of the device on a narrow slope, so as to facilitate operation and usage by an operator. Furthermore, an auxiliary temperature detection function is also increased, such that the operator may more conveniently observe temperature distribution around a tumor and its variation range, thereby ensuring that the high-temperature working medium and the low-temperature working medium may be accurately controlled so as to complete a safe and effective ablation therapy on lesion tissue and helping the operator to better manipulate his/her device to comprehensively kill cancer cells.

Figure 10:
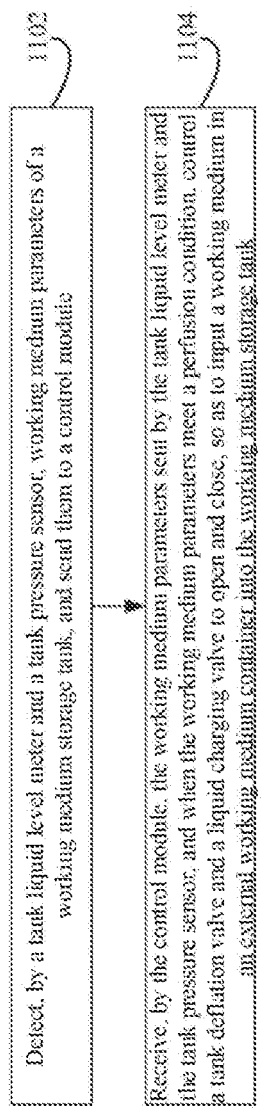
FIG. 10 is a processing flow chart of an electrical control method for minimally invasive tumor therapies provided by an embodiment of the disclosure.

FIG. 10 shows a processing flow chart of an electrical control method for minimally invasive tumor therapies provided by an embodiment of the disclosure. The method is applicable to the above electrical control system for minimally invasive tumor therapies, and may include the following steps 1102 to 1104.

At step 1102, the tank liquid level meter and the tank pressure sensor detect working medium parameters of the working medium storage tank, and send them to a control module.

The working medium parameter sent by the tank liquid level meter may be a liquid level of a working medium inside the working medium storage tank, and the working medium parameter sent by the tank pressure sensor may be a tank pressure intensity of the working medium storage tank.

At step 1104, the control module receives the working medium parameters sent by the tank liquid level meter and the tank pressure sensor, and when the working medium parameters meet a perfusion condition, controls a tank deflation valve and a liquid charging valve to open or close respectively, so as to input a working medium from an external working medium container into the working medium storage tank.

In one implementation of the embodiment, the step of controlling, when the working medium parameters meet a perfusion condition, a tank deflation valve and a liquid charging valve to open or close respectively so as to input a working medium in an external working medium container into the working medium storage tank may be specifically implemented by determining, when a received liquid level is lower than a first liquid level threshold value, whether a received tank pressure intensity is less than a first pressure intensity threshold value; opening, if the received tank pressure intensity is not less than the first pressure intensity threshold value, the tank deflation valve, so as to reduce an internal pressure intensity of the working medium storage tank; and continuing to determine whether the received tank pressure intensity is less than the first pressure intensity threshold value, until it is determined that the received tank pressure intensity is less than the first pressure intensity threshold value, keeping the tank deflation valve in an open state, and opening the liquid charging valve, so as to input the working medium from the external working medium container into the working medium storage tank.

The liquid charging valve is located on a conveying pipeline between the working medium storage tank and the external working medium container. The liquid charging valve is arranged close to the working medium storage tank. When the liquid charging valve is in an open state, the working medium storage tank is perfused with the working medium from the external working medium container via the conveying pipeline.

In one implementation of the embodiment, after keeping the tank deflation valve in an open state, and opening the liquid charging valve, the method also includes the step of closing the working medium output valve when opening the liquid charging valve.

In a possible implementation, the perfusion module is a refrigeration working medium perfusion module, in which case before the determining whether a received tank pressure intensity is less than a first pressure intensity threshold value, the method also includes the steps of detecting, when a received liquid level is lower than a first liquid level threshold value, whether the Dewar conveying pipeline is connected with the refrigeration tank body according to an insertion message sent by the refrigeration tank perfusion port insertion detection unit; performing, when the Dewar conveying pipeline is connected with the refrigeration tank body, the operation step of determining whether a received tank pressure intensity is less than a first pressure intensity threshold value.

In one implementation of the embodiment, after keeping the tank deflation valve in an open state, and opening the liquid charging valve, the method also includes the step of opening the phase separation valve and closing the liquid charging deflation valve when opening the liquid charging valve.

In one implementation of the embodiment, after keeping the tank deflation valve in an open state, and opening the liquid charging valve, the method also includes the steps of determining, during a first preset duration after opening the liquid charging valve, whether a received liquid level is lower than a first liquid level threshold value; determining, if the received liquid level is lower than the first liquid level threshold value, whether the perfusion port pressure intensity is greater than a second pressure intensity threshold value; feeding back, if the perfusion port pressure intensity is not greater than the second pressure intensity threshold value, a prompt message for opening the Dewar vessel; continuing to determine, if the perfusion port pressure intensity is greater than the second pressure intensity threshold value, whether the received liquid level is lower than the first liquid level threshold value, until the received liquid level is not lower than the first liquid level threshold value.

In one implementation of the embodiment, after determining, during a first preset duration after opening the liquid charging valve, whether a received liquid level is lower than a first liquid level threshold value, the method also includes the steps of closing, when it is determined that the received liquid level is not lower than the first liquid level threshold value, the tank deflation valve, the liquid charging valve and the phase separation valve, and keeping the working medium output valve in a closed state and opening the liquid charging deflation valve; determining whether the perfusion port pressure intensity is less than a third pressure intensity threshold value; feed backing, if the perfusion port pressure intensity is less than the third pressure intensity threshold value, a prompt message for pulling out the Dewar conveying pipeline; and keeping, if the perfusion port pressure intensity is not less than the third pressure intensity threshold value, the respective open/close states of the tank deflation valve, the liquid charging valve, the working medium output valve, the phase separation valve and the liquid charging deflation valve unchanged, until the received perfusion port pressure intensity is less than the third pressure intensity threshold value.

Figure 11:
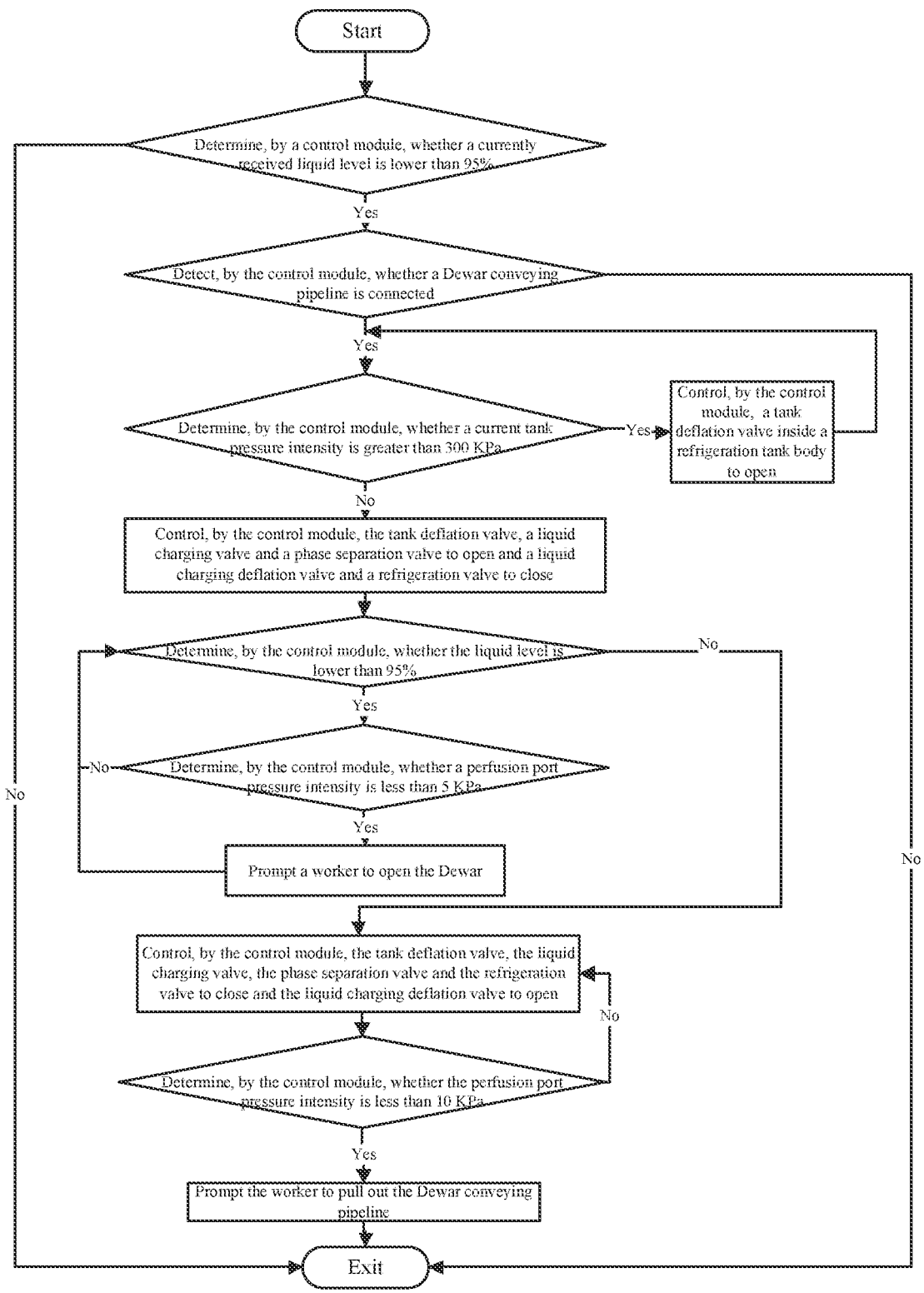
FIG. 11 is a processing flow chart of an automatic perfusion process of a refrigeration working medium provided by an embodiment of the disclosure.

In an implementation, FIG. 11 is a processing flow chart of an automatic perfusion process of a refrigeration working medium provided by an embodiment of the disclosure. As shown in FIG. 11, a tank liquid level meter detects a current liquid level inside a refrigeration tank body, and sends it to a control module. The control module determines whether the currently received liquid level is lower than 95%, and if the currently received liquid level is not lower than 95%, it exits. If the currently received liquid level is lower than 95%, an operation of automatically adding liquid nitrogen may be performed, in which case the control module detects whether a Dewar conveying pipeline is connected. If the Dewar conveying pipeline is not connected, it exits. If the Dewar conveying pipeline is connected, the control module determines whether a current tank pressure intensity is greater than 300 KPa. If the current tank pressure intensity is greater than 300 KPa, the control module controls a tank deflation valve inside a refrigeration tank body to open so as to perform a deflation action, and it returns to perform the operation step where the control module determines whether the current tank pressure intensity is greater than 300 KPa. If the current tank pressure intensity is not greater than 300 KPa, the control module controls the tank deflation valve, a liquid charging valve and a phase separation valve to open and a liquid charging deflation valve and a refrigeration valve to close, so as to perform an action of adding liquid nitrogen.

The control module keeps detecting the liquid level inside the refrigeration tank body, and determines whether the liquid level is lower than 95%. If the liquid level is lower than 95%, it determines whether a perfusion port pressure intensity is less than 5 kpa. If the perfusion port pressure intensity is less than 5 kpa, it proves that Dewar vessel is not opened, the control module sends a prompt message to an industrial personal computer so as to prompt an operator to open the Dewar vessel on a display. If the perfusion port pressure intensity is not less than 5 kpa, it returns to perform the operation step where the control module determines whether the liquid level is lower than 95% until the liquid level is not lower than 95%, in which case it is judged that the liquid level has been filled, and the control module controls the tank deflation valve, the liquid charging valve, the phase separation valve and the refrigeration valve to close and the liquid charging deflation valve to open. The control module determines whether the perfusion port pressure intensity is less than 10 KPa. If the perfusion port pressure intensity is less than 10 KPa, it is considered safe to pull out the Dewar conveying pipeline in this case, and the control module sends a message to the industrial personal computer so as to prompt the operator on the display to pull out the Dewar conveying pipeline for ending the flow of adding liquid nitrogen. If the perfusion port pressure intensity is not less than 10 KPa, it returns to perform the step where the control module controls the tank deflation valve, the liquid charging valve, the phase separation valve and the refrigeration valve to close and the liquid charging deflation valve to open (that is, keeping the respective open/close states of the tank deflation valve, the liquid charging valve, the phase separation valve, the refrigeration valve and the liquid charging deflation valve unchanged), until the perfusion port pressure intensity is less than 10 KPa.

In one implementation of the embodiment, the electrical control system for minimally invasive tumor therapies may also include a vacuum tank and an air compressor. The vacuum tank is provided with a vacuum tank pressure sensor P. A vacuum pumping pipeline is arranged between the vacuum tank and the air compressor. A vacuum pumping valve is provided on the vacuum pumping pipeline. A liquid conveying pipeline and a gas conveying pipeline are arranged between the refrigeration tank body and the vacuum tank. A vacuum tank liquid charging valve is provided on the liquid conveying pipeline. An auxiliary pressurization valve is provided on the gas conveying pipeline. After the refrigeration tank body is perfused with a refrigeration working medium, the control module may further control the refrigeration working medium inside the refrigeration tank body to be output to an ablation probe for a therapeutic surgery. That is, the electrical control method for the minimally invasive tumor therapies also includes the steps of determining, after controlling a pressurization valve to open, whether a tank body pressure intensity of the refrigeration tank body reaches a fourth pressure intensity threshold value within a second preset duration; controlling, if the fourth pressure intensity threshold value is not reached, the vacuum tank liquid charging valve to open, so as to press the refrigeration working medium inside the refrigeration tank body into the vacuum tank via the liquid conveying pipeline; determining whether a vacuum tank pressure intensity sent by the vacuum tank pressure sensor is greater than a fifth pressure intensity threshold value, controlling, if the vacuum tank pressure intensity is higher than the fifth pressure intensity threshold value, the vacuum tank liquid charging valve to close and the auxiliary pressurization valve to open, so as to increase a pressure intensity inside the refrigeration tank body; and determining whether a tank body pressure intensity inside the refrigeration tank body is greater than a sixth pressure intensity threshold value, and controlling, if the tank body pressure intensity is greater than the sixth pressure intensity threshold value, the auxiliary pressurization valve to close.

In one implementation of the embodiment, before opening the vacuum tank liquid charging valve to carry out auxiliary pressurization on the refrigeration tank body, it is necessary to detect whether a pressure intensity of the vacuum tank meets a condition, and before controlling the vacuum tank liquid charging valve to open, the method also includes the steps of: determining whether the vacuum tank pressure intensity is less than a seventh pressure intensity threshold value for a third preset duration; controlling, if the vacuum tank pressure intensity is not less than the seventh pressure intensity threshold value for the third preset duration, the vacuum pumping valve to open, and returning to perform the operation step of determining whether the vacuum tank pressure intensity is less than the seventh pressure intensity threshold value for the third preset duration; and controlling, if the vacuum tank pressure intensity is less than the seventh pressure intensity threshold value for the third preset duration, the vacuum pumping valve to close, and performing the operation step of controlling the vacuum tank liquid charging valve to open.

Figure 12:
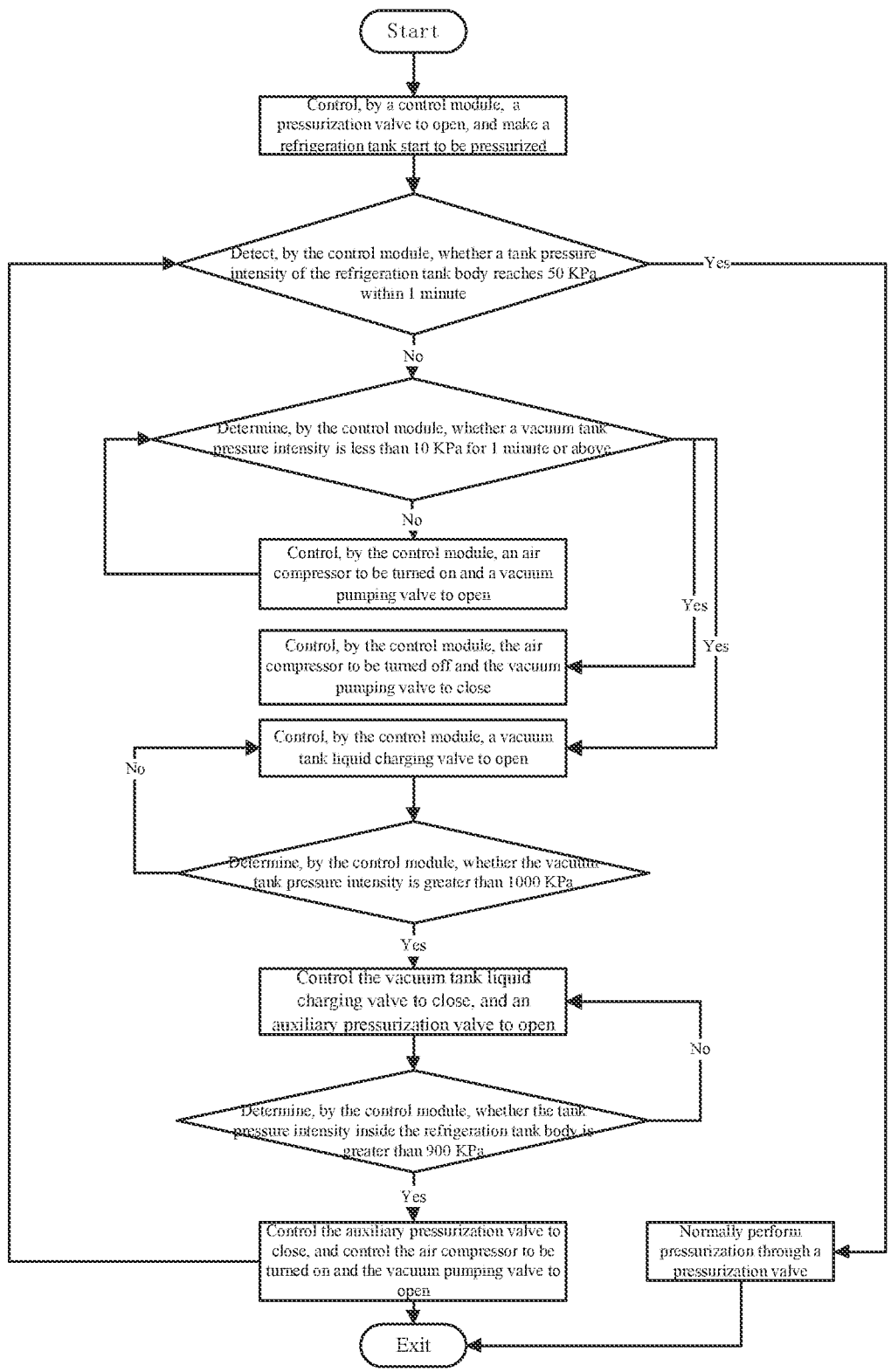
FIG. 12 is a processing flow chart of an auxiliary pressurization process provided by an embodiment of the disclosure.

In an implementation, FIG. 12 is a processing flow chart of an auxiliary pressurization process provided by an embodiment of the disclosure. As shown in FIG. 12, a control module controls a pressurization valve to open, and a refrigeration tank starts to be pressurized. The control module detects whether a tank pressure intensity of the refrigeration tank body reaches 50 KPa within 1 minute, and if the tank pressure intensity of the refrigeration tank body reaches 50 KPa within 1 minute, pressurization is normally performed through a pressurization valve. If the tank pressure intensity of the refrigeration tank body does not reach 50 KPa within 1 minute, the control module determines whether a vacuum tank pressure intensity is less than 10 KPa for 1 minute or above. If the vacuum tank pressure intensity is not less than 10 KPa for 1 minute or above, the control module controls an air compressor to be turned on and a vacuum pumping valve to open, and continues to determine whether the vacuum tank pressure intensity is less than 10 KPa for 1 minute or above, until it is determined that the vacuum tank pressure intensity is less than 10 KPa for 1 minute or above, and the control module controls the vacuum pumping valve to close and the air compressor to be turned off. If the vacuum tank pressure intensity is less than 10 KPa for 1 minute or above, the control module controls the vacuum tank liquid charging valve to open so as to press a refrigeration working medium inside the refrigeration tank body into the vacuum tank via a liquid conveying pipeline, and the refrigeration working medium is gasified into gas in the vacuum tank, which increases the vacuum tank pressure intensity. The control module determines whether the vacuum tank pressure intensity is greater than 1000 KPa. If the vacuum tank pressure intensity is not greater than 1000 KPa, it returns to perform the operation step where the control module controls a vacuum tank liquid charging valve to open (that is, keeping the vacuum tank liquid charging valve in an open state and continuing to monitor the vacuum tank pressure intensity). If the vacuum tank pressure intensity is greater than 1000 KPa, the control module controls the vacuum tank liquid charging valve to close and an auxiliary pressurization valve to open so as to increase a tank pressure intensity inside the refrigeration tank body. The control module determines whether the tank pressure intensity inside the refrigeration tank body is greater than 900 KPa. If the tank pressure intensity inside the refrigeration tank body is not greater than 900 KPa, it returns to perform the operation step of controlling the vacuum tank liquid charging valve to close and the auxiliary pressurization valve to open (that is, keeping the vacuum tank liquid charging valve in a close state and the auxiliary pressurization valve in an open state, and continuing to monitor the tank pressure intensity of the refrigeration tank body). If the tank pressure intensity inside the refrigeration tank body is greater than 900 KPa, the control module controls the auxiliary pressurization valve to close (and keep the vacuum tank liquid charging valve in a close state), and controls the air compressor to be turned on and the vacuum pumping valve to open.

In one possible implementation, the perfusion module may also be a heating working medium perfusion module, in which case after keeping the tank deflation valve in an open state and opening the liquid charging valve, the method also includes the steps of turning on, when the liquid charging valve is opened, the alcohol input pump, so as to input a heating working medium in the alcohol bottle into the heating tank body; determining whether a received liquid level has changed after a fourth preset duration; and feeding back, if the received liquid level has not changed, a prompt message for replacing an alcohol bottle; or continuing to determine, if the received liquid level has changed, whether the received liquid level is lower than the first liquid level threshold value, until the received liquid level is not lower than the first liquid level threshold value, and closing the tank deflation valve, the liquid charging valve and the alcohol input pump.

Figure 13:
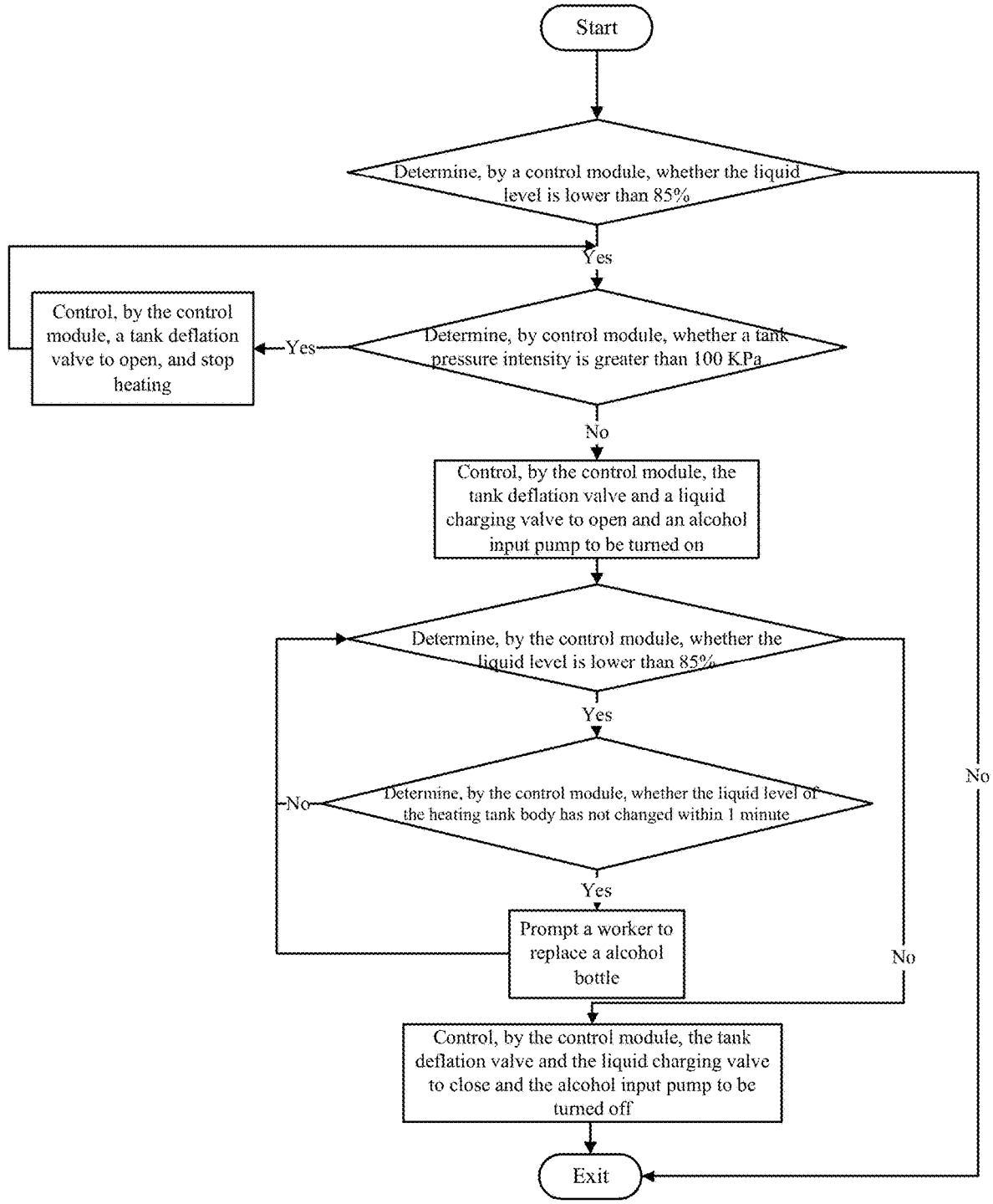
FIG. 13 is a processing flow chart of an automatic perfusion process of a heating working medium provided by an embodiment of the disclosure.

In an implementation, FIG. 13 is a processing flow chart of an automatic perfusion process of a heating working medium provided by an embodiment of the disclosure. As shown in FIG. 13, a tank liquid level meter detects a current liquid level inside a heating tank body, and sends it to a control module. The control module determines whether the liquid level is lower than 85%. If the liquid level is not lower than 85%, it exits. If the liquid level is lower than 85%, an action of filling alcohol may be automatically performed, in which case the control module determines whether a tank pressure intensity is greater than 100 KPa. If the tank pressure intensity is greater than 100 KPa, the control module controls a tank deflation valve to open, stops heating and performs a deflation action, and it returns to perform the step where the control module determines whether the tank pressure intensity is greater than 100 KPa. If the tank pressure intensity is not greater than 100 KPa, the control module controls the tank deflation valve and a liquid charging valve to open and an alcohol input pump to be turned on so as to perform an action of adding alcohol.

The control module determines whether the liquid level is lower than 85%. If the liquid level is lower than 85%, the control module determines whether the liquid level of the heating tank body has not changed within 1 minute. If the liquid level of the heating tank body has changed within 1 minute, it returns to perform the operation step where the control module determines whether the liquid level is lower than 85%. If the liquid level of the heating tank body has not changed within 1 minute, it proves that there is no liquid in an alcohol bottle, and the control module sends a prompt message to an industrial personal computer so as to prompt an operator to replace the alcohol bottle on a display, and returns to perform the operation step where the control module determines whether the liquid level is lower than 85%. If the liquid level is not lower than 85%, the control module controls the tank deflation valve and the liquid charging valve to close and the alcohol input pump to be turned off so as to end the action of adding alcohol.

In one implementation of the embodiment, when the perfusion module is the heating working medium perfusion module, the electrical control method for the minimally invasive tumor therapies may also include the steps of determining, when a received liquid level is higher than a second liquid level threshold valve, whether a heater is powered by a main power supply; determining, if the heater is powered by the main power supply, whether a received heating tank body temperature sent by a tank temperature sensor reaches a first temperature threshold value; and controlling, if the received heating tank body temperature does not reach the first temperature threshold value, the heater to start heating; or controlling, if the received heating tank body temperature reaches the first temperature threshold value, the heater to stop heating.

In one implementation of the embodiment, after controlling the heater to start heating, the method also includes the steps of determining, in the process of controlling the heater to perform heating, whether a received tank body pressure intensity exceeds an eighth pressure intensity threshold value; and opening, when the received tank body pressure intensity exceeds the eighth pressure intensity threshold value, the tank deflation valve, and continuing to determine whether the received tank body pressure intensity exceeds the eighth pressure intensity threshold value, until the received tank body pressure intensity does not exceed the eighth pressure intensity threshold value, and closing the tank deflation valve.

Figure 14A:
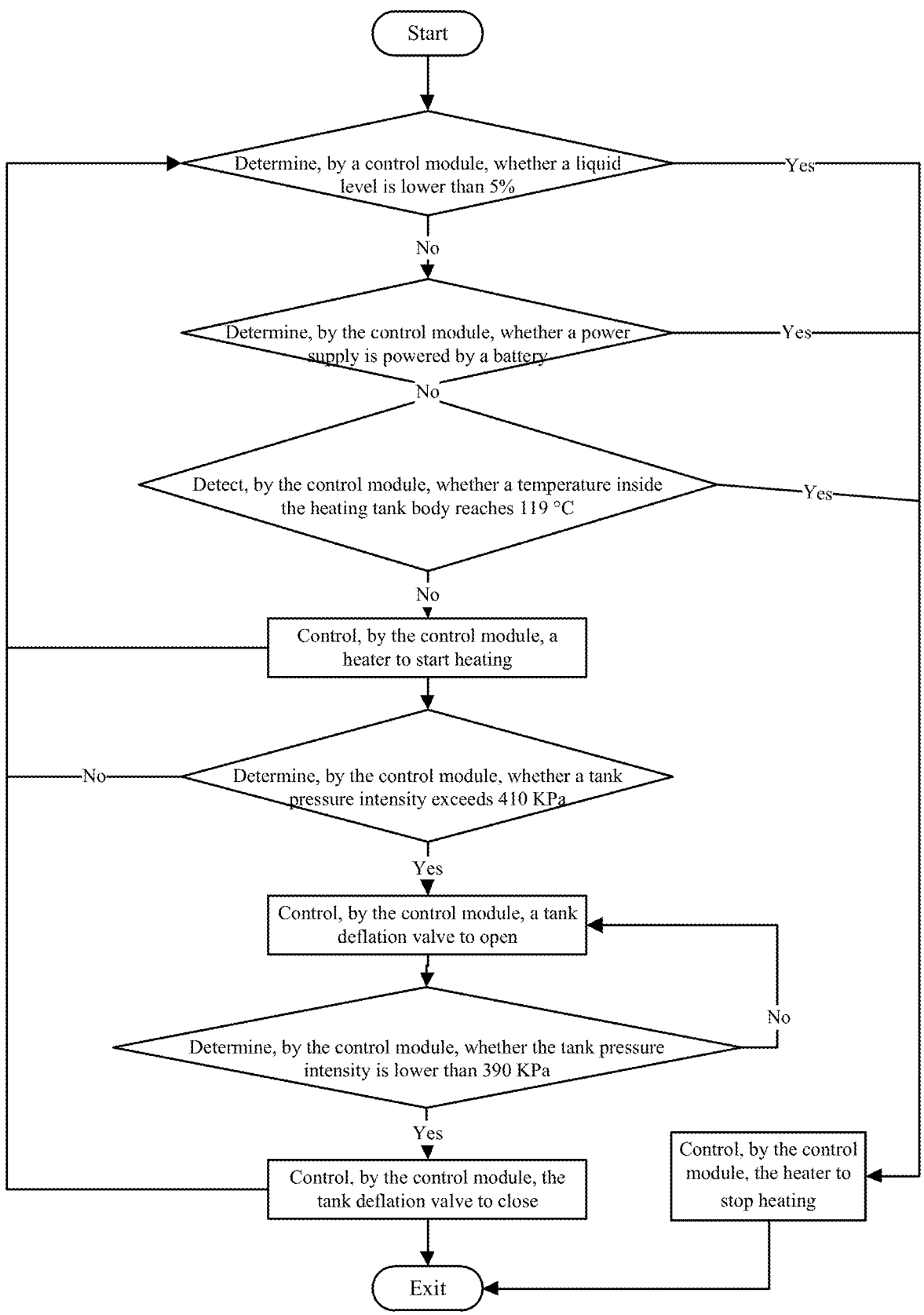
FIG. 14a is a processing flow chart of a heating process provided by an embodiment of the disclosure.

In an implementation, FIG. 14*a* is a processing flow chart of a heating process provided by an embodiment of the disclosure. As shown in FIG. 14*a*, a tank liquid level meter in a heating tank body detects a current liquid level inside the heating tank body, and sends it to a control module. The control module determines whether the liquid level is lower than 5%. If the liquid level is lower than 5%, the control module controls a heater to stop heating. If the liquid level is not lower than 5%, the control module determines whether a power supply is powered by a battery. If the power supply is powered by the battery, the control module controls the heater to stop heating. If the power supply is not powered by the battery, the control module detects whether a temperature inside the heating tank body reaches 119° C. If the temperature inside the heating tank body reaches 119° C., the control module controls the heater to stop heating. If the temperature inside the heating tank body does not reach 119° C., the control module controls the heater to start heating. Later, the liquid level inside the heating tank body will drop as the heating working medium is consumed during a surgery, and it is necessary to return to perform the operation step of heating after the operation step where the control module determines whether the liquid level is lower than 5%.

Meanwhile, the control module determines whether the tank pressure intensity exceeds 410 KPa. If the tank pressure intensity does not exceeds 410 KPa, it means that no deflation is required, and the heating process is continued, that is, it returns to perform the operation step of heating after the operation step where the control module determines whether the liquid level is lower than 5%. If the tank pressure intensity exceeds 410 KPa, the control module controls the tank deflation valve to open to reduce an internal pressure intensity of the heating tank body. The control module determines whether the tank pressure intensity is lower than 390 KPa. If the tank pressure intensity is lower than 390 KPa, the control module controls the tank deflation valve to close to stop deflating, and it returns to perform the operation step of heating after the operation step where the control module determines whether the liquid level is lower than 5%. If the tank pressure intensity is not lower than 390 KPa, it returns to perform the operation step where the control module controls the tank deflation valve to open, and deflation is continued.

In one implementation of the embodiment, after determining whether a received heating tank body temperature sent by the tank temperature sensor reaches a first temperature threshold value, the method also includes the steps of determining whether the received heating tank body temperature exceeds a second temperature threshold value; and controlling, if the received heating tank body temperature exceeds the second temperature threshold value, the temperature switch to be disconnected, and feeding back a temperature alarm message.

In one implementation of the embodiment, the valve box may also include a temperature feeler interface and a thermocouple acquisition board. In this case, the electrical control method for the minimally invasive tumor therapies may also include the steps that the temperature feeler interface may be connected with a temperature feeler, which may be internally provided with thermocouple temperature measurement points; and the thermocouple acquisition board is connected with the temperature feeler to acquire temperatures measured by the thermocouple temperature measurement points and send them to the control module.

In one implementation of the embodiment, the valve box may also include an ablation probe interface, an ablation probe inlet temperature sensor, an ablation probe backflow temperature sensor and a probe conveying pipe insertion detection switch. In this case, the electrical control method for the minimally invasive tumor therapies may also include the steps that the ablation probe interface is connected with a working medium conveying pipeline, which is connected with an ablation probe, and the working medium conveying pipeline and the ablation probe each include a working medium output pipeline and a working medium backflow pipeline; the probe conveying pipe insertion detection switch detects whether the working medium conveying pipeline is interfaced with the ablation probe interface, and feeds back, when it is detected the working medium conveying pipeline is not interfaced with the ablation probe interface, a prompt message for interfacing by means of the control module; the ablation probe inlet temperature sensor detects an output temperature of the working medium conveying pipeline, and sends it to the control module; and the ablation probe backflow temperature sensor detects and sends a backflow temperature of the working medium backflow pipeline to the control module.

In one implementation of the embodiment, the working medium output valve may be a proportioning valve, and the sizes of ice balls output from the ablation probe may be adjusted by adjusting the opening proportion of the proportioning valve. In the case of connecting two ablation probes, the sizes of the output ice balls are therefore controlled to avoid the ice balls output from the two ablation probes from being significantly different. That is, the electrical control method for the minimally invasive tumor therapies also includes the steps of determining, in the case of connecting two ablation probes, whether backflow temperatures of the two ablation probes fall within a first temperature interval simultaneously, and controlling, if the backflow temperatures of the two ablation probes fall within the first temperature interval simultaneously, the proportioning valves corresponding to the two ablation probes to open to a preset proportion; and determining, if the backflow temperatures of the two ablation probes do not fall within the first temperature interval simultaneously, whether the backflow temperatures of the two ablation probes fall within a second temperature interval simultaneously, and adjusting, if the backflow temperatures of the two ablation probes fall within the second temperature interval simultaneously, the proportioning valve corresponding a ablation probe with a lower backflow temperature in the two ablation probes according to a temperature difference between the backflow temperatures of the two ablation probes; or determining, if the backflow temperatures of the two ablation probes do not fall within the second temperature interval simultaneously, whether the backflow temperatures of the two ablation probes fall within a third temperature interval simultaneously, and adjusting, if the backflow temperatures of the two ablation probes fall within the third temperature interval simultaneously, the proportioning valve corresponding to the ablation probe with the lower backflow temperature in the two ablation probes according to the temperature difference between the backflow temperatures of the two ablation probes.

In one implementation of the embodiment, the step of adjusting the proportioning valve corresponding a ablation probe with a lower backflow temperature in the two ablation probes according to a temperature difference between the backflow temperatures of the two ablation probes may further be specifically implemented by determining whether the first temperature difference between the backflow temperatures of the two ablation probes is greater than or equal to a first difference threshold value; and controlling, if the first temperature difference between the backflow temperatures of the two ablation probes is greater than or equal to the first difference threshold value, the proportioning valve corresponding to one ablation probe with a lower backflow temperature in the two ablation probes to reduce its opening by a numerical value corresponding to the first temperature difference; or controlling, if the first temperature difference between the backflow temperatures of the two ablation probes is not greater than or equal to the first difference threshold value, the proportioning valve corresponding to the ablation probe with the lower backflow temperature in the two ablation probes to reduce its opening by a numerical value corresponding to the first difference threshold value.

Figure 14B:
FIG. 14b is a processing flow chart of an adjusting process of a proportioning valve provided by an embodiment of the disclosure.

In an implementation, FIG. 14b is a processing flow chart of an adjusting process of a proportioning valve provided by an embodiment of the disclosure. As shown in FIG. 14b, a control module determines whether the number of connected ablation probes is two. If the number of the connected ablation probes is not two, the control module controls proportioning valves corresponding to the ablation probes to open to 100%. If the number of the connected ablation probes is two, the control module determines whether backflow temperatures of the two ablation probes are simultaneously greater than minus 100° C. If the backflow temperatures of the two ablation probes are simultaneously greater than minus 100° C., the control module controls the proportioning valves corresponding to the ablation probes to open to 100%. If the backflow temperatures of the two ablation probes are not simultaneously greater than minus 100° C., the control module determines whether the backflow temperatures of the two ablation probes are simultaneously greater than or equal to minus 140° C. and less than or equal to minus 100° C. If the backflow temperatures of the two ablation probes are simultaneously greater than or equal to minus 140° C. and less than or equal to minus 100° C., the control module determines whether a first temperature difference between the backflow temperatures of the two ablation probes is greater than or equal to 20° C. If the first temperature difference between the backflow temperatures of the two ablation probes is greater than or equal to 20° C., the control module controls the proportioning valve corresponding to the ablation probe with the lower backflow temperature in the two ablation probes to reduce its opening by a numerical value corresponding to the first temperature difference. If the first temperature difference between the backflow temperatures of the two ablation probes is not greater than or equal to 20° C., the control module controls the proportioning valve corresponding to the ablation probe with the lower backflow temperature in the two ablation probes to reduce its opening by 20%.

If it is determined that the backflow temperatures of the two ablation probes are not simultaneously greater than or equal to minus 140° C. and less than or equal to minus 100° C., the control module determines whether the backflow temperatures of the two ablation probes are simultaneously greater than or equal to minus 196° C. and less than or equal to minus 140° C. If the backflow temperatures of the two ablation probes are not simultaneously greater than or equal to minus 196° C. and less than or equal to minus 140° C., it returns to continue to perform the step where the control module determines whether the backflow temperatures of the two ablation probes are simultaneously greater than minus 100° C. If the backflow temperatures of the two ablation probes are simultaneously greater than or equal to minus 196° C. and less than or equal to minus 140° C., the control module determines whether a second temperature difference between the backflow temperatures of the two ablation probes is greater than or equal to 30° C. If the second temperature difference between the backflow temperatures of the two ablation probes is greater than or equal to 30° C., the control module controls the proportioning valve corresponding to the ablation probe with the lower backflow temperature in the two ablation probes to reduce its opening by a numerical value corresponding to the second difference. If the second temperature difference between the backflow temperatures of the two ablation probes is not greater than or equal to 30° C., the control module controls the proportioning valve corresponding to the ablation probe with the lower backflow temperature in the two ablation probes to reduce its opening by 30%. After adjusting the proportioning valves, it may return to continue to perform the operation step where the control module determines whether the backflow temperatures of the two ablation probes are simultaneously greater than minus 100° C.

In one implementation of the embodiment, the electrical control system for minimally invasive tumor therapies also includes a working medium recovery module. The working medium recovery module includes a working medium backflow port, a heat regenerator and a working medium output port. A liquid storage cup is arranged below the working medium output port. A weighing sensor is arranged below the liquid storage cup. The working medium backflow port and the working medium output port are located at different ports of the heat regenerator, and working medium flowing back from a working medium backflow pipeline in an ablation probe enter the heat regenerator through the working medium backflow port, and are output from the working medium output port. In this case, the electrical control method for minimally invasive tumor therapies may also include the steps that the liquid storage cup stores liquid output from the working medium output port; the weighing sensor measures and feeds back the weight of stored liquid in the liquid storage cup to the control module; and the control module is configured to receive the weight of the stored liquid fed back by the weighing sensor, and feed back a stored liquid alarm message when the weight of the stored liquid is greater than a weight threshold value.

In one implementation of the embodiment, the working medium recovery module may also include a fan, which may be arranged close to the heat regenerator. In this case, the electrical control method for minimally invasive tumor therapies may also include the steps that a recovery temperature sensor measures the working medium recovery temperature of the working medium backflow port, and feeds it to the control module; and the control module receives the working medium recovery temperature, and controls the fan to start to work when the working medium recovery temperature is higher than a third temperature threshold value or lower than a fourth temperature threshold value.

In one implementation of the embodiment, the working medium recovery module may also include a liquid storage drawer and a limit switch. In this case, the electrical control method for minimally invasive tumor therapies may also include the steps that the liquid storage drawer arranges the liquid storage cup; and the limit switch detects whether placement of the liquid storage cup is completed, and when it is detected that the placement of the liquid storage cup is completed, feeds back a prompt of meeting surgical conditions depending upon the control module.

In one implementation of the embodiment, the electrical control system for minimally invasive tumor therapies may also include an interactive module. The interactive module may include a motion control handle and a motion grip. A power box may also include a battery and a motion control unit. The motion control unit includes a motion control board and a power wheel. In this case, the electrical control method for the minimally invasive tumor therapies may also include the steps that the battery supplies power to the motion control unit; and the motion control board detects the gear state of the motion grip and the position state of the motion control handle, and controls the motion state of the power wheel according to the gear state and the position state.

In one implementation of the embodiment, the controlling the motion state of the power wheel according to the gear state and the position state may be specifically implemented by controlling the motion state of the power wheel to be a neutral state when it is detected that the gear state is the neutral state; controlling the motion state of the power wheel to be a stopping state when it is detected that the position state is a lifting-up state, and in the stopping state, when it is detected that a position signal of the power wheel is at a high electrical level, controlling the motion state of the power wheel to be a rising state; controlling the motion state of the power wheel to be a descending state when it is detected that the gear state is a non-neutral state and the position state is a pressing-down state, and setting the position signal of the power wheel into a high electrical level when it is detected that descending of the power wheel is completed; and controlling the motion state of the power wheel to be a lower-position brake state when it is detected that the gear state is the non-neutral state, the position state is the pressing-down state, and the position signal is at the high electrical level, controlling the motion state of the power wheel to be an advance state if it is detected that the gear state is an advance state, and controlling the motion state of the power wheel to be a reverse state if it is detected that the gear state is an reverse state.

In one implementation of the embodiment, the controlling the motion state of the power wheel according to the gear state and the position state may also be specifically implemented by storing and feeding back, if it is detected that the position signal of the power wheel is at a low electrical level after the motion state of the power wheel is controlled to be a descending state for a fifth preset duration, a power wheel alarm message; controlling, if it is detected that the motion state of the power wheel has not changed after the motion state of the power wheel is controlled to be a lower-position brake state for a sixth preset duration, the motion state of the power wheel to be a rising state; setting the position signal of the power wheel to be at the low electrical level when it is detected that rising of the power wheel is completed, and storing and feeding back, if it is detected that the position signal is at a high electrical level after a seventh preset duration, a power wheel alarm message; and storing and feeding back, if it is detected that there is an abnormal current in the power wheel, the power wheel alarm message.

In one implementation of the embodiment, the detecting the gear state of the motion grip and the position state of the motion control handle may also be specifically implemented by determining whether there is an abnormal current in the power motor and the lifting motor; and stopping supplying power to the power motor and the lifting motor when the current is abnormal, and storing and feeding back a power wheel alarm message. In one implementation of the embodiment, after detecting the gear state of the motion grip and the position state of the motion control handle, the method may also include the step of controlling the motion state of the power wheel to be a lower-position brake state when it is detected that the emergency stop button is pressed down, and storing and feeding back an emergency stop alarm message.

In one implementation of the embodiment, the electrical control method for minimally invasive tumor therapies may also include the steps that the motion control board acquires attribute parameters of the battery, and feeds the attribute parameters back to the interactive module for display; determines whether the battery is abnormal according to the attribute parameters of the battery; and feeds back a battery alarm message to the interactive module when the battery is abnormal.

Figure 15:
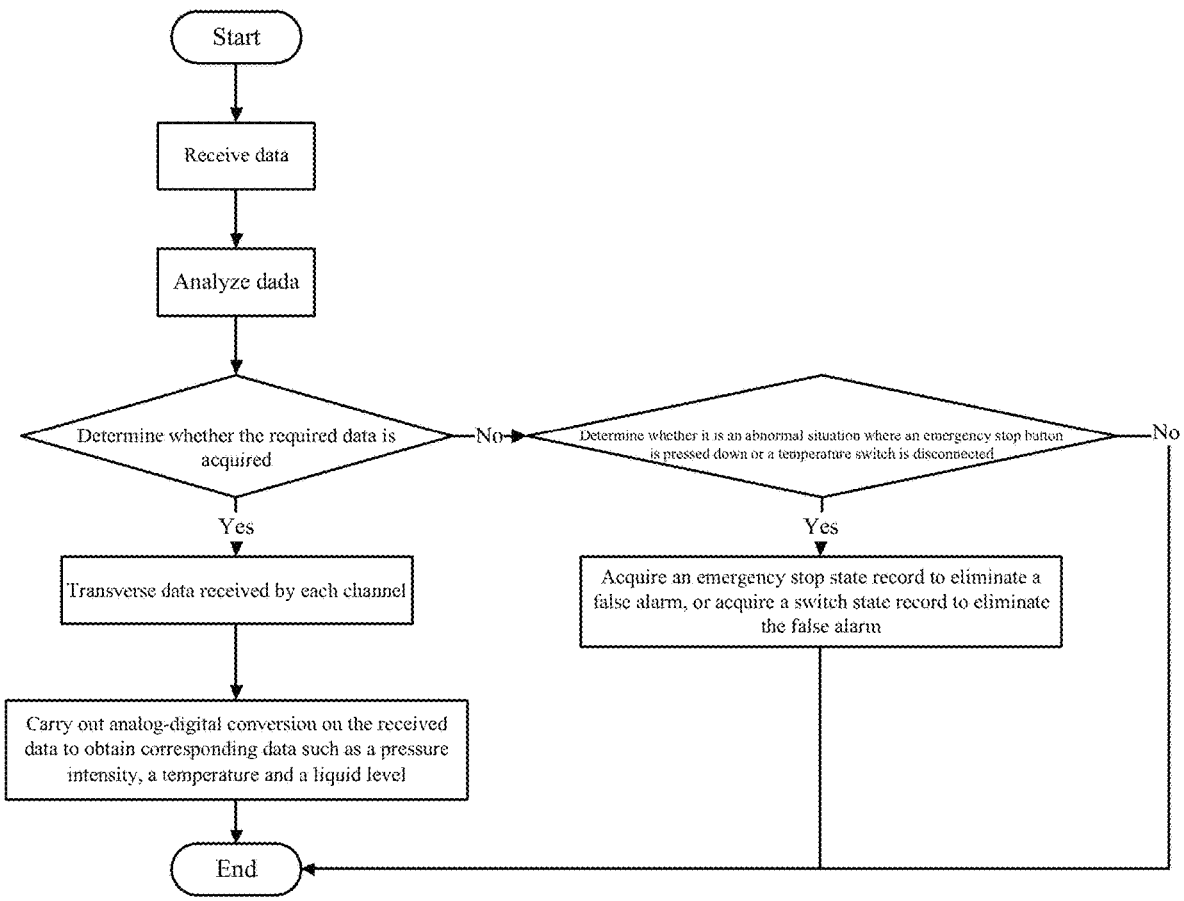
FIG. 15 is a processing flow chart of a data processing procedure of a control module provided by an embodiment of the disclosure.

In an implementation, FIG. 15 is a processing flow chart of a data processing procedure of a control module provided by an embodiment of the disclosure. As shown in FIG. 15, after receiving data (which may refer to data that is sent by any element in the electrical control system for minimally invasive tumor therapies to a control module), the control module analyzes the data to determine whether the required data is acquired. If no required data is acquired, the control module determines whether it is an abnormal situation where an emergency stop button is pressed down or a temperature switch is disconnected. If the required data is acquired, an emergency stop state record is acquired to eliminate a false alarm, or a switch state record is acquired to eliminate the false alarm. If the required data is acquired, it is possible to transverse data received by each channel (i.e., data sent by different elements) and carry out analog-digital conversion on the received data to obtain corresponding data such as a pressure intensity, a temperature and a liquid level.

By utilizing the electrical control method for minimally invasive tumor therapies provided in the disclosure, a tank liquid level meter and a tank pressure sensor in a perfusion module may detect relevant working medium parameters of a working medium storage tank, and send them to the control module. The control module may determine whether the working medium parameters meet a perfusion condition based on the working medium parameters, and when they meet the perfusion condition, automatically control the tank deflation valve and the liquid charging valve to open or close respectively, such that working medium in the external working medium container may be automatically input into the working medium storage tank, thereby achieving automatic adding of the working medium, simplifying the process of adding the working medium, saving on labor and time costs, ensuring that the working medium may be automatically and accurately added, significantly improving the timeliness, accuracy and efficiency of adding the working medium.

In addition, the system also includes a motion control unit, such that a device may be moved easily and conveniently, and when there is an emergency, braking and emergency stop may be carried out to prevent collision of the device on a narrow slope, so as to facilitate operation and usage by an operator. Furthermore, an auxiliary temperature detection function is also increased, such that the operator may more conveniently observe temperature distribution around a tumor and its variation range, thereby ensuring that the high-temperature working medium and the low-temperature working medium may be accurately controlled so as to complete a safe and effective ablation therapy on lesion tissue and helping the operator to better manipulate his/her device to comprehensively kill cancer cells.

The above description is a schematic solution of the electrical control method for the minimally invasive tumor therapies of the embodiment. The solution of the electrical control method for the minimally invasive tumor therapies is of the same concept as the solution of the above electrical control system for minimally invasive tumor therapies. All contents not described in detail in the solution of the electrical control method for the minimally invasive tumor therapies may refer to the description on the solution of the above electrical control system for minimally invasive tumor therapies.

Figure 16:
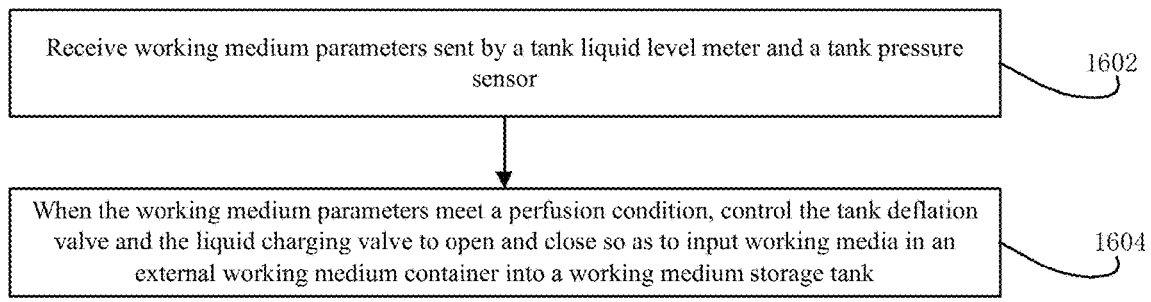
FIG. 16 is a processing flow chart of another electrical control method for minimally invasive tumor therapies provided by an embodiment of the disclosure.

FIG. 16 is a processing flow chart of another electrical control method for minimally invasive tumor therapies provided by an embodiment of the disclosure. The method is applicable to the control module of the mentioned electrical control system for minimally invasive tumor therapies, and in one implementation, the method may includes steps 1602 to 1604.

At step 1602, working medium parameters sent by a tank liquid level meter and a tank pressure sensor are received.

At step 1604, when the working medium parameters meet a perfusion condition, the tank deflation valve and the liquid charging valve are controlled to open or close respectively so as to input working medium from an external working medium container into a working medium storage tank.

In practical application, as for the process of adding the refrigeration working medium, the tank liquid level meter may detect and send a liquid level inside a current refrigeration tank body to the control module. If the liquid level is lower than 95%, an operation of adding the refrigeration working medium may be performed. Then, the control module detects whether a Dewar conveying pipeline is connected (the Dewar conveying pipeline connected to a Dewar vessel has a magnetic ring at its front end, the refrigeration working medium perfusion module has a magnetic ring detector inside it, after the Dewar conveying pipeline is connected in place, the detector detects the magnetic ring and generates a signal, in which case it proves that the Dewar conveying pipeline is normally connected with a device). If it is detected that the Dewar conveying pipeline is normally connected, the signal is transmitted to the control module, and the control module continues to detect a tank pressure intensity of the refrigeration tank body. If the tank pressure intensity is greater than 300 KPa, the control module controls the tank deflation valve of the refrigeration tank to open and perform a deflation action (to prevent an excessive pressure intensity and the resultant danger). If the tank pressure intensity is less than or equal to 300 kpa, the control module controls the tank deflation valve, the liquid charging valve and the phase separation valve of the refrigeration tank to open and a liquid charging deflation valve and a refrigeration valve to close so as to perform a liquid nitrogen adding action.

The control module keeps detecting the liquid level of the refrigeration tank body. If the liquid level is lower than 95%, the control module continues to detect a perfusion port pressure intensity of a refrigeration tank perfusion port. If the perfusion port pressure intensity is less than 5 KPa, it proves that the Dewar vessel is not opened, the control module sends a message to an industrial personal computer (IPC) so as to prompt an operator to open the Dewar vessel on a display. If the perfusion port pressure intensity is greater than or equal to 5 KPa, the liquid level of the refrigeration tank body is always detected, until the liquid level is greater than or equal to 95%, in which case it is judged that the liquid level has been filled, and the control module controls the tank deflation valve, the liquid charging valve, the phase separation valve and the refrigeration valve to close and the liquid charging deflation valve to open, and continues to detect the perfusion port pressure intensity. If the perfusion port pressure intensity is less than 10 KPa, it is considered safe to pull out the conveying pipe, the control module sends a message to the IPC so as to prompt the operator to pull out the conveying pipe on the display and end the liquid nitrogen adding process. If the perfusion port pressure intensity is greater than or equal to 10 KPa, the control module may control the refrigeration tank deflation valve, the liquid charging valve, the phase separation valve and the refrigeration valve to close and the liquid charging deflation valve to open, until the perfusion port pressure intensity is less than 10 KPa.

As for the process of adding the heating working medium, the tank liquid level meter may detect and send a liquid level inside a current heating tank body to the control module. If the liquid level is lower than 85%, a filling action may be performed. The control module detects the tank pressure intensity of the heating tank body. If the tank pressure intensity is greater than 100 KPa, the control module controls the tank deflation valve to open to stop heating and to perform a deflation action (to prevent an excessive pressure intensity and the resultant danger). If the tank pressure intensity is less than or equal to 100 KPa, the control module controls the tank deflation valve, the liquid charging valve and the alcohol input pump of the heating tank to open so as to perform an alcohol adding action. The control module keeps detecting the liquid level of the heating tank body. If the liquid level is lower than 85% and meanwhile the liquid level inside the heating tank body has not changed within 1 minute, it proves that there is no liquid in an alcohol bottle, and the control module may send a message to the IPC to remind the operator on the display that there is a need to replace the alcohol bottle. If the liquid level is higher than 85%, the control module may control the tank deflation valve of the heating tank, the liquid charging valve and the alcohol input pump to close so as to end the alcohol adding action.

In addition, the system also includes a motion control unit, such that a device may be moved easily and conveniently, and when there is an emergency, braking and emergency stop may be carried out to prevent collision of the device on a narrow slope, so as to facilitate operation and usage by an operator. Furthermore, an auxiliary temperature detection function is also increased, such that the operator may more conveniently observe temperature distribution around a tumor and its variation range, thereby helping the operator to better manipulate his/her device to comprehensively kill cancer cells.

By utilizing the electrical control method for the minimally invasive tumor therapies provide in the disclosure, the control module and the perfusion module are arranged in the electrical control system for minimally invasive tumor therapies. The tank liquid level meter and the tank pressure sensor in the perfusion module may detect relevant working medium parameters of the working medium storage tank and send them to the control module. The control module may determine whether the working medium parameters meet a perfusion condition based on the working medium parameters, and when they meet the perfusion condition, automatically control the tank deflation valve and the liquid charging valve to open or close respectively, such that working medium in the external working medium container may be automatically input into the working medium storage tank, thereby achieving automatic adding of the working medium, simplifying the process of adding the working medium, saving on labor and time costs, ensuring that the working medium may be automatically and accurately added, significantly improving the timeliness, accuracy and efficiency of adding the working medium, and ensuring that the high-temperature working medium and the low-temperature working medium may be subsequently accurately controlled so as to complete a safe and effective ablation therapy on lesion tissue.

The above description is a schematic solution of the electrical control method for the minimally invasive tumor therapies of the embodiment. The solution of the electrical control method for the minimally invasive tumor therapies is of the same concept as the solution of the above electrical control system for minimally invasive tumor therapies and the solution of the above electrical control method for the minimally invasive tumor therapies as shown in FIG. 10. All contents not described in detail in the solution of the electrical control method for the minimally invasive tumor therapies may refer to the description on the solution of the above electrical control system for minimally invasive tumor therapies and the solution of the above electrical control method for the minimally invasive tumor therapies as shown in FIG. 10.

Figure 17:
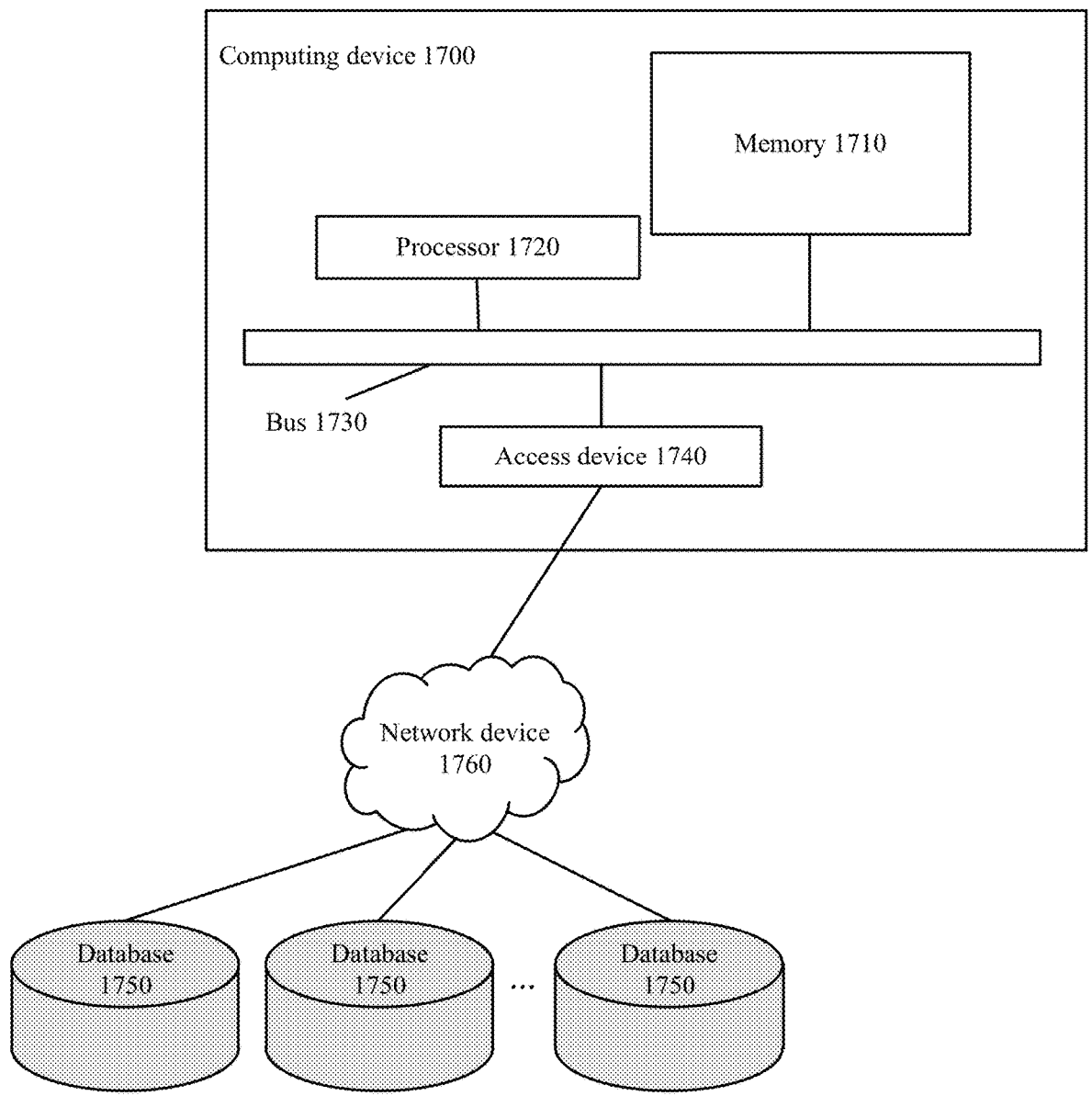
FIG. 17 is a structural block diagram of a computing device provided by an embodiment of the disclosure.

FIG. 17 is a structural block diagram of a computing device 1700 provided by an embodiment of the disclosure. Parts of the computing device 1700 include but are not limited to a memory 1710 and a processor 1720. The processor 1720 and the memory 1710 are connected through a bus 1730, and a database 1750 is configured to store data.

The computing device 1700 also includes an access device 1740, and the access device 1740 enables the computing device 1700 to communicate via one or more networks 1760. Examples of these networks include a public switched telephone network (PSTN), a local area network (LAN), a wide area network (WAN), a personal area network (PAN) or a combination of communication networks such as the Internet. The access device 1740 may include one or more of any type of interfaces (e.g., network interface card (NIC)), wired or wireless, such as an IEEE802.11 wireless local area network (WLAN) wireless interface, a world interoperability for microwave access (Wi-MAX) interface, an Ethernet interface, a universal serial bus (USB) interface, a cellular network interface, a Bluetooth interface, and a near field communication (NFC) interface.

In one embodiment of the disclosure, the above parts of the computing device 1700 and other parts not shown in FIG. 17 may also connected with each other, e.g., through the bus. It should be understood that the structural block diagram of the computing device 1700 as shown in FIG. 17 is for the exemplary purpose only and is not a limitation on the scope of the disclosure. Those skilled in the art may add or replace other parts as required.

The computing device 1700 may be any type of stationary or mobile computing device, and it includes a mobile computer or a mobile computing device (e.g., a tablet computer, a personal digital assistant, a laptop computer, a notebook computer and a netbook), a mobile phone (e.g., a smartphone), a wearable computing device (e.g., a smartwatch and smart glasses) or other types of mobile devices, or it includes a stationary computing device such as a desktop computer or a PC. The computing device 1700 may also be a mobile or static server.

The processor 1720 is configured to execute the following computer executable instruction, so as to implement the operation steps of the above electrical control method for minimally invasive tumor therapies.

The above is a schematic solution of a computing device of the embodiment. The solution of the computing device is of the same concept as the solution of the above electrical control system for minimally invasive tumor therapies. All contents not described in detail in the solution of the computing device may refer to the description on the solution of the above electrical control system for minimally invasive tumor therapies.

An embodiment of the disclosure also provides a computer readable storage medium, which stores a computer instruction, and the instruction is executed by a processor to implement the operation steps of the above electrical control method for the minimally invasive tumor therapies.

The above is a schematic solution of the computer readable storage medium of the embodiment. The solution of the storage medium is of the same concept as the solution of the above electrical control system for minimally invasive tumor therapies. All contents not described in detail in the solution of the storage medium may refer to the description on the solution of the above electrical control system for minimally invasive tumor therapies.

The above describes the specific embodiments of the disclosure. Other embodiments fall within the scope of the attached claims. In some cases, the actions or steps recorded in the claims may be performed in a different order than in the embodiments and still achieve the desired result. In addition, the processes depicted in the accompanying drawings do not necessarily require a specific or sequential order to be shown in order to achieve the desired result. In some implementations, multitasking and parallel processing are also possible or may be advantageous.

The computer instruction includes a computer program code, which may be in a source code form, an object code form, an executable file form, certain intermediate forms, etc. The computer readable storage medium may include any entity or device capable of carrying the computer program code, a recording medium, a USB flash disk, a mobile hard disk, a magnetic disk, a compact disc, a computer memory, read-only memory (ROM), a random access memory (RAM), an electric carrier signal, a telecommunications signal, a software distribution medium, etc. The contents contained in the computer readable medium may be increased or decreased as appropriate in accordance with the requirements of legislation and patent practice in the jurisdiction, and for example, in some jurisdictions, according to legislation and patent practice, the computer readable medium does not include the electric carrier signals and the telecommunications signal.

It should be noted that each of the foregoing method embodiments is described as a series of combinations of actions for simplicity of description, but those skilled in the art should be aware that the disclosure is not limited by the sequence of actions described, as certain steps may be performed in other sequences or simultaneously according to the disclosure. Secondly, those skilled in the art should also be aware that the actions and modules involved in the embodiments described in the disclosure are not all necessarily required by the disclosure.

In the above embodiments, the description of each embodiment has its own focus, and what is not described in detail in one embodiment may refer to the relevant descriptions of other embodiments.

The above disclosed embodiments are only used to help illustrate the disclosure. The above embodiments are not an exhaustive recitation of all the details and do not limit the invention to only the specific implementation described. Obviously, many modifications and variations may be made in accordance with the disclosure. These embodiments have been selected and specifically described in the disclosure to better explain the principles and practical applications of the disclosure so that the disclosure may be well understood and utilized by those skilled in the art to which they belong. The disclosure is limited only by the claims and their full scope and equivalents.

The invention claimed is:

1. An electrical control system for minimally invasive tumor therapies, wherein the system comprises a control module, a perfusion module and a power box, the perfusion module comprising a refrigeration working medium perfusion module and a heating working medium perfusion module, the refrigeration working medium perfusion module comprising a first working medium storage tank, a first tank liquid level meter, a first tank pressure sensor, a first tank deflation valve, a first liquid charging valve and a first external working medium container; and the heating working medium perfusion module comprising a second working medium storage tank, a second tank liquid level meter, a second tank pressure sensor, a second tank deflation valve, a second liquid charging valve, and a second external working medium container;

the power box being configured to supply power to the control module and the perfusion module;

the control module being configured to receive working medium parameters sent by the first tank liquid level meter of the refrigeration working medium perfusion module and the first tank pressure sensor of the refrigeration working medium perfusion module, and to control, when the working medium parameters meet a perfusion condition, the first tank deflation valve of the refrigeration working medium perfusion module and the first liquid charging valve of the refrigeration working medium perfusion module to open or close, so as to input a refrigeration working medium from the first external working medium container of the refrigeration working medium perfusion module into the first working medium storage tank of the refrigeration working medium perfusion module;

wherein the working medium parameter sent by the first tank liquid level meter of the refrigeration working medium perfusion module is a liquid level of a working medium inside the first working medium storage tank of the refrigeration working medium perfusion module, and the working medium parameter sent by the first tank pressure sensor of the refrigeration working medium perfusion module is a tank pressure intensity of the first working medium storage tank of the refrigeration working medium perfusion module;

the control module further being configured to receive working medium parameters sent by the second tank liquid level meter of the heating working medium perfusion module and the second tank pressure sensor of the heating working medium perfusion module, and to control, when the working medium parameters meet a perfusion condition, the second tank deflation valve of the heating working medium perfusion module and the second liquid charging valve of the heating working medium perfusion module to open or close, so as to input a heating working medium from the second external working medium container of the heating working medium perfusion module into the second working medium storage tank of the heating working medium perfusion module;

wherein the working medium parameter sent by the second tank liquid level meter of the heating working medium perfusion module is a liquid level of a working medium inside the second working medium storage tank of the heating working medium perfusion module, and the working medium parameter sent by the second tank pressure sensor of the heating working medium perfusion module is a tank pressure intensity of the second working medium storage tank of the heating working medium perfusion module; and the control module is further configured to:

determine, when a received liquid level of the first working medium storage tank of the refrigeration working medium perfusion module is lower than a first liquid level threshold value, whether a received tank pressure intensity of the first working medium storage tank of the refrigeration working medium perfusion module is less than a first pressure intensity threshold value; wherein the first liquid level threshold value is 95% or 90%, and the first pressure intensity threshold value is 300 KPa;

open, if the received tank pressure intensity of the first working medium storage tank of the refrigeration working medium perfusion module is not less than the first pressure intensity threshold value, the first tank deflation valve of the refrigeration working medium perfusion module, so as to reduce an internal pressure intensity of the first working medium storage tank of the refrigeration working medium perfusion module;

continue to determine whether the received tank pressure intensity of the first working medium storage tank of the refrigeration working medium perfusion module is less than the first pressure intensity threshold value; and open, if the received tank pressure intensity of the first working medium storage tank of the refrigeration working medium perfusion module is less than the first pressure intensity threshold value, the first liquid charging valve of the refrigeration working medium perfusion module, so as to input the refrigeration working medium from the first external working medium container of the refrigeration working medium perfusion module into the first working medium storage tank of the refrigeration working medium perfusion module.

2. The electrical control system for minimally invasive tumor therapies according to claim 1, wherein the system further comprises a valve box, in which a refrigeration valve is provided; and the control module is further configured to:
   close the refrigeration valve when opening the first liquid charging valve of the refrigeration working medium perfusion module.

3. The electrical control system for minimally invasive tumor therapies according to claim 2, wherein in the refrigeration working medium perfusion module, the first working medium storage tank being a refrigeration tank body, the first external working medium container being a Dewar vessel, the Dewar vessel being connected with the refrigeration tank body by means of a Dewar conveying pipeline; the refrigeration working medium perfusion module further comprises a refrigeration tank perfusion port insertion detection unit; and
   the control module is further configured to:
      detect, when the received liquid level of the first working medium storage tank of the refrigeration working medium perfusion module is lower than the first liquid level threshold value, whether the Dewar conveying pipeline is connected with the refrigeration tank body according to an insertion message sent by the refrigeration tank perfusion port insertion detection unit; and
      determine, when the Dewar conveying pipeline is connected with the refrigeration tank body, whether the received tank pressure intensity of the first working medium storage tank of the refrigeration working medium perfusion module is less than the first pressure intensity threshold value.

4. The electrical control system for minimally invasive tumor therapies according to claim 3, wherein the refrigeration working medium perfusion module further comprises a liquid charging deflation valve, the liquid charging deflation valve being located on the Dewar conveying pipeline and arranged close to the Dewar vessel; the valve box is further provided with a phase separation valve; and
   the control module is further configured to:
      open the phase separation valve and close the liquid charging deflation valve when opening the first liquid charging valve of the refrigeration working medium perfusion module.

5. The electrical control system for minimally invasive tumor therapies according to claim 4, wherein the refrigeration working medium perfusion module further comprises a perfusion port pressure sensor, which is arranged at a perfusion port of the Dewar vessel;
   the perfusion port pressure sensor is configured to detect and send a perfusion port pressure intensity of the refrigeration tank body to the control module; and
   the control module is further configured to:
   determine, during a first preset duration after opening the first liquid charging valve of the refrigeration working medium perfusion module, whether the received liquid level of the first working medium storage tank of the refrigeration working medium perfusion module is lower than the first liquid level threshold value, wherein the first preset duration is 2 minutes, 5 minutes, or 7 minutes;
   determine, if the received liquid level of the first working medium storage tank of the refrigeration working medium perfusion module is lower than the first liquid level threshold value, whether the perfusion port pressure intensity is greater than a second pressure intensity threshold value; and
   feed back, if the perfusion port pressure intensity is not greater than the second pressure intensity threshold value, a message for opening the Dewar vessel; or
   continue to determine, if the perfusion port pressure intensity is greater than the second pressure intensity threshold value, whether the received liquid level of the first working medium storage tank of the refrigeration working medium perfusion module is lower than the first liquid level threshold value, until the received liquid level of the first working medium storage tank of the refrigeration working medium perfusion module is not lower than the first liquid level threshold value, wherein the second pressure intensity threshold value is 5 KPa.

6. The electrical control system for minimally invasive tumor therapies according to claim 5, wherein the control module is further configured to:
   close, when it is determined that the received liquid level of the first working medium storage tank of the refrigeration working medium perfusion module is not lower than the first liquid level threshold value, the first tank deflation valve of the refrigeration working medium perfusion module, the first liquid charging valve of the refrigeration working medium perfusion module and the phase separation valve, and open the liquid charging deflation valve;
   determine whether the perfusion port pressure intensity is less than a third pressure intensity threshold value, which is 10 KPa; and
   feed back, if the perfusion port pressure intensity is less than the third pressure intensity threshold value, a message that can safely separate the Dewar conveying pipeline from the refrigeration tank body; or
   keep, if the perfusion port pressure intensity is not less than the third pressure intensity threshold value, respective open/close states of the first tank deflation valve of the refrigeration working medium perfusion module, the first liquid charging valve of the refrigeration working medium perfusion module, the refrigeration valve, the phase separation valve, and the liquid charging deflation valve unchanged, until a received perfusion port pressure intensity is less than the third pressure intensity threshold value.

7. The electrical control system for minimally invasive tumor therapies according to claim 3, wherein the system further comprises a vacuum tank and an air compressor, which are used for rapidly pressurizing the refrigeration tank body, the vacuum tank being provided with a vacuum tank pressure sensor, a vacuum pumping pipeline being arranged between the vacuum tank and the air compressor, a vacuum pumping valve and a one-way valve being provided on the vacuum pumping pipeline; and a liquid conveying pipeline and a gas conveying pipeline are arranged between the refrigeration tank body and the vacuum tank, a vacuum tank liquid charging valve being provided on the liquid conveying pipeline, an auxiliary pressurization valve being provided on the gas conveying pipeline.

8. The electrical control system for minimally invasive tumor therapies according to claim 7, wherein the control module is further configured to:
   determine, whether a tank pressure intensity of the refrigeration tank body reaches a fourth pressure intensity threshold value within a second preset duration, wherein the second preset duration is 1 minute and the fourth pressure intensity threshold value is 50 KPa;
   control, if the tank pressure intensity of the refrigeration tank body does not reach the fourth pressure intensity threshold value, the vacuum tank liquid charging valve to open, so as to press a refrigeration working medium from the refrigeration tank body into the vacuum tank via the liquid conveying pipeline;

determine whether a vacuum tank pressure intensity sent by the vacuum tank pressure sensor is greater than a fifth pressure intensity threshold value, control, if the vacuum tank pressure intensity sent by the vacuum tank pressure sensor is greater than the fifth pressure intensity threshold value, the vacuum tank liquid charging valve to close, and open the auxiliary pressurization valve to increase a tank pressure intensity inside the refrigeration tank body, wherein the fifth pressure intensity threshold value is 1000 KPa; and determine whether a tank pressure intensity of the refrigeration tank body is greater than a sixth pressure intensity threshold value, and control, if the tank pressure intensity of the refrigeration tank body is greater than the sixth pressure intensity threshold value, the auxiliary pressurization valve to close, wherein the sixth pressure intensity threshold value is 900 KPa.

9. The electrical control system for minimally invasive tumor therapies according to claim 8, wherein the control module is further configured to:

determine whether the vacuum tank pressure intensity is less than a seventh pressure intensity threshold value for a third preset duration;

control, if the vacuum tank pressure intensity is not less than the seventh pressure intensity threshold value for the third preset duration, the air compressor and the vacuum pumping valve to open, and return to perform an operation step of determining whether the vacuum tank pressure intensity is less than a seventh pressure intensity threshold value for a third preset duration, wherein the third preset duration is 1 minute and the seventh pressure intensity threshold value is 10 KPa; and control, if the vacuum tank pressure intensity is less than the seventh pressure intensity threshold value for the third preset duration, the air compressor and the vacuum pumping valve to close, and perform the operation step of controlling the vacuum tank liquid charging valve to open.

10. The electrical control system for minimally invasive tumor therapies according to claim 2, wherein in the heating working medium perfusion module, the second working medium storage tank being a heating tank body, the second external working medium container being an alcohol bottle; the heating working medium perfusion module further comprises an alcohol input pump, the alcohol input pump being located on a conveying pipeline between the heating tank body and the alcohol bottle and arranged close to the alcohol bottle;

the control module is further configured to:

turn on, when the second liquid charging valve of the heating working medium perfusion module is opened, the alcohol input pump, so as to input the heating working medium from the alcohol bottle into the heating tank body;

determine whether a received liquid level of the second working medium storage tank of the heating working medium perfusion module has changed after a fourth preset duration, wherein the fourth preset duration is 2 minutes, 5 minutes, or 7 minutes; and feed back, if the received liquid level of the second working medium storage tank of the heating working medium perfusion module has not changed, a message for replacing the alcohol bottle; or continue to determine, if the received liquid level of the second working medium storage tank of the heating working medium perfusion module has changed, whether the received liquid level of the second working medium storage tank of the heating working medium perfusion module is lower than the first liquid level threshold value, until the received liquid level of the second working medium storage tank of the heating working medium perfusion module is not lower than the first liquid level threshold value, and close the second tank deflation valve of the heating working medium perfusion module, the second liquid charging valve of the heating working medium perfusion module and the alcohol input pump.

11. The electrical control system for minimally invasive tumor therapies according to claim 10, wherein the power box comprises a main power supply and a battery; the heating working medium perfusion module further comprises a heater and a tank temperature sensor, wherein the heater is used to heat the heating tank body; and the control module is further configured to:

determine, when the received liquid level of the second working medium storage tank of the heating working medium perfusion module is higher than a second liquid level threshold value, whether the heater is powered by the main power supply, wherein the second liquid level threshold value is 5% or 10%;

determine, if the heater is powered by the main power supply, whether a received heating tank body temperature sent by the tank temperature sensor reaches a first temperature threshold value, which is 119° C.; and control, if the received heating tank body temperature does not reach the first temperature threshold value, the heater to start heating; or control, if the received heating tank body temperature reaches the first temperature threshold value, the heater to stop heating.

12. The electrical control system for minimally invasive tumor therapies according to claim 11, wherein the control module is further configured to:

determine, in a process of controlling the heater to perform heating, whether a received tank body pressure intensity of the second working medium storage tank of the heating working medium perfusion module exceeds an eighth pressure intensity threshold value; and open, when the received tank body pressure intensity exceeds the eighth pressure intensity threshold value, the second tank deflation valve of the heating working medium perfusion module, and continue to determine whether the received tank body pressure intensity of the second working medium storage tank of the heating working medium perfusion module exceeds the eighth pressure intensity threshold value, until the received tank body pressure intensity of the second working medium storage tank of the heating working medium perfusion module does not exceed the eighth pressure intensity threshold value, and close the second tank deflation valve of the heating working medium perfusion module, wherein the eighth pressure intensity threshold value is 410 KPa.

* * * * *